US00RE41150E

(19) United States
(12) Reissued Patent
Ferraris et al.

(10) Patent Number: US RE41,150 E
(45) Date of Reissued Patent: Feb. 23, 2010

(54) COMPOUNDS AND THEIR USE

(75) Inventors: Dana V. Ferraris, Eidersburg, MD (US); Jia-He Li, Cockeysville, MD (US)

(73) Assignee: Eisai Corporation of North America, Woodcliff Lake, NJ (US)

(21) Appl. No.: 12/007,463

(22) Filed: Jan. 10, 2008

Related U.S. Patent Documents

Reissue of:
(64) Patent No.: 6,887,996
Issued: May 3, 2005
Appl. No.: 09/996,776
Filed: Nov. 30, 2001

U.S. Applications:
(
(60) Provisional application No. 60/250,132, filed on Dec. 1, 2000, and provisional application No. 60/310,274, filed on Aug. 7, 2001.

(51) Int. Cl.
*C07D 413/00* (2006.01)
*C07D 401/00* (2006.01)
*C07D 215/04* (2006.01)

(52) U.S. Cl. ..... 544/128; 544/361; 546/181
(58) Field of Classification Search ..... 544/128, 544/361; 546/181
See application file for complete search history.

(56) References Cited

U.S. PATENT DOCUMENTS 6,121,278 A * 9/2000 Jackson et al. ..... 514/292
6,201,020 B1 * 3/2001 Zhang et al. ..... 514/544
6,306,889 B1 * 10/2001 Li et al. ..... 514/410
6,346,536 B1 * 2/2002 Li et al. ..... 514/286
6,348,475 B1 * 2/2002 Zhang et al. ..... 514/309
6,380,193 B1 * 4/2002 Li et al. ..... 514/243
6,387,902 B1 * 5/2002 Zhang et al. ..... 514/249
6,395,749 B1 * 5/2002 Li et al. ..... 514/310
6,514,983 B1 * 2/2003 Li et al. ..... 514/285

FOREIGN PATENT DOCUMENTS

WO WO 99/11624 * 3/1999
WO WO 99/59975 * 11/1999
WO WO 00/42040 * 7/2000
WO WO 01/23390 A2 * 4/2001
WO WO 02/044183 A3 * 6/2002

OTHER PUBLICATIONS

By Itoh et al. (Chemical & Pharmaceutical Bulletin (1974), 22(6), 4131–2). Abstract.*

Ames et al. (Tetrahedron (1984), 40(10), 1919–25).*

Ames et al, Tetrahedron, vol. 40, No. 10, 1984, pp. 1919–1925.*

Park et al, J. Org. Chem, vol. 66, 2001, pp. 2197–2206.*

* cited by examiner

*Primary Examiner*—Bruck Kifle
(74) *Attorney, Agent, or Firm*—Connolly Bove Lodge & Hutz LLP

(57) ABSTRACT

This invention relates to compounds, pharmaceutical compositions, and methods of using the disclosed compounds for inhibiting PARP.

2 Claims, 2 Drawing Sheets

COMPOUNDS AND THEIR USE

Matter enclosed in heavy brackets [ ] appears in the original patent but forms no part of this reissue specification; matter printed in italics indicates the additions made by reissue.

This application claims benefit of U.S. Provisional Application No. 60/250,132, filed Dec. 1, 2000, and U.S. Provisional Application No. 60/310,274, filed Aug. 7, 2001, the entire contents of each of which is incorporated herein by reference.

The present invention relates to inhibitors of the nuclear enzyme poly(adenosine 5'-diphospho-ribose) polymerase ["poly(ADP-ribose) polymerase" or "PARP", which is also referred to as ADPRT (NAD:protein (ADP-ribosyl transferase polymersing)) and PARS (poly(ADP-ribose) synthetase) and provides compounds and compositions containing the disclosed compounds. Moreover, the present invention provides methods of using the disclosed PARP inhibitors to prevent and/or treat tissue damage resulting from cell damage or death due to necrosis or apoptosis; neural tissue damage resulting from, for example, ischemia and reperfusion injury, such as cerebral ischemic stroke, head trauma or spinal cord injury; neurological disorders and neurodegenerative diseases, such as, for example, Parkinson's or Alzheimer's diseases and multiple sclerosis; to prevent or treat vascular stroke; to treat or prevent cardiovascular disorders, such as, for example, myocardial infarction; to treat other conditions and/or disorders such as, for example, age-related muscular degeneration, AIDS and other immune senescence diseases, inflammation, arthritis, gout, atherosclerosis, cachexia, cancer, degenerative diseases of skeletal muscle involving replicative senescence, diabetes (such as diabetes mellitus), inflammatory bowel disorders (such as colitis and Crohn's disease), acute pancreatitis, mucositis, hemorrhagic shock, splanchnic artery occlusion shock, multiple organ failure (such as involving any of the kidney, liver, renal, pulmonary, retinal, pancreatic and/or skeletal muscle systems), acute autoimmune thyroiditis, muscular dystrophy, osteoarthritis, osteoporosis, chronic and acute pain (such as neuropathic pain), renal failure, retinal ischemia, septic shock (such as endotoxic shock), local and/or remote endothelial cell dysfunction (such are recognized by endo-dependent relaxant responses and up-regulation of adhesion molecules), inflammation and skin aging; to extend the lifespan and proliferative capacity of cells, such as, for example, as general mediators in the generation of oxidants, proinflammatory mediators and/or cytokines, and general mediators of leukocyte infiltration, calcium ion overload, phospholipid peroxidation, impaired nitric oxide metabolism and/or reduced ATP production; to alter gene expression of senescent cells; or to radiosensitize hypoxic tumor cells.

PARP (EC 2.4.2.30), also known as PARS (for poly (ADP-ribose) synthetase), or ADPRT (for NAD:protein (ADP-ribosyl) transferase (polymerising)) is a major nuclear protein of 116 kDa. It is mainly present in almost all eukaryotes. The enzyme synthesizes poly(ADP-ribose), a branched polymer that can consist of over 200 ADP-ribose units from NAD. The protein acceptors of poly(ADP-ribose) are directly or indirectly involved in maintaining DNA integrity. They include histones, topoisomerases, DNA and RNA polymerases, DNA ligases, and $Ca^{2+}$- and $Mg^{+}$-dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold. Among the many functions attributed to PARP is its major role in facilitating DNA repair by ADP-ribosylation and therefore coordinating a number of DNA repair proteins. As a result of PARP activation, NAD levels significantly decline. While many endogeneous and exogeneous agents have been shown to damage DNA and activate PARP, peroxynitrite, formed from a combination of nitric oxide (NO) and superoxide, appears to be a main perpetrator responsible for various reported disease conditions in vivo, e.g., during shock, stroke and inflammation.

Extensive PARP activation leads to severe depletion of NAD in cells suffering from massive DNA damage. The short life of poly(ADP-ribose) (half-life <1 min) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of NAD to ADP-ribose. In less than an hour, over-stimulation of PARP can cause a drop of NAD and ATP to less than 20% of the normal level. Such a scenario is especially detrimental during ischemia when deprivation of oxygen has already drastically compromised cellular energy output. Subsequent free radical production during reperfusion is assumed to be a major cause of tissue damage. Part of the ATP drop, which is typical in many organs during ischemia and reperfusion, could be linked to NAD depletion due to poly(ADP-ribose) turnover. Thus, PARP or PARG inhibition is expected to preserve the cellular energy level to potentiate the survival of ischaemic tissues after insult.

Poly(ADP-ribose) synthesis is also involved in the induced expression of a number of genes essential for inflammatory response. PARP inhibitors suppress production of inducible nitric oxide synthase (iNOS) in macrophages, P-type selection and intercellular adhesion molecule-1 (CAM-1) in endothelial cells. Such activity underlies the strong anti-inflammation effects exhibited by PARP inhibitors. PARP inhibition is able to reduce necrosis by preventing translocation and infiltration of neutrophils to the injured tissues (Zhang, J. "PARP inhibition: a novel approach to treat ischaemia/reperfusion and inflammation-related injuries", Chapter 10 in Emerging Drugs (1999) 4: 209–221 Ashley Publications Ltd. and references cited therein.)

PARP production is activated by damaged DNA fragments which, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are consumed for every molecule of NAD (the source of ADP-ribose and PARP substrate) regenerated, NAD is depleted by massive PARP activation and, in the efforts to re-synthesize NAD, ATP may also be depleted.

It has been reported that PARP activation plays a key role in both NMDA- and NO-induced neurotoxicity. This has been demonstrated in cortical cultures and in hippocampal slices wherein prevention of toxicity is directly correlated to PARP inhibition potency (Zhang et al., "Nitric Oxide Activation of Poly)ADP-Ribose) Synthetase in Neurotoxicity", Science, 263:687–89 (1994) and Wallis et al., "Neuroprotection Against Nitric Oxide Injury with Inhibitors of ADP-Ribosylation", NeuroReport, 5:3, 245–48 (1993)). The potential role of PARP inhibitors in treating neurodegenerative diseases and head trauma has thus been recognized even if the exact mechanism of action has not yet been elucidated (Endres et al., "Ischenic Brain Injury is Mediated by the Activation of Poly(ADP-Ribose)Polymerase", J. Cereb. Blood Flow Metabol., 17:1143–51 (1997) and Wallis et al., "Traumatic Neuroprotection with Inhibitors of Nitric Oxide and ADP-Ribosylation, Brain Res., 710:169–77 (1996)).

Similarly, it has been demonstrated that single injections of PARP inhibitors have reduced the infarct size caused by ischemia and reperfusion of the heart or skeletal muscle in rabbits. In these studies, a single injection of 3-aminobenzamide (10 mg/kg), either one minute before occlusion or one minute before reperfusion, caused similar reductions in infarct size in the heart (32–42%) while 1,5-dihydroxyisoquinoline (1 mg/kg), another PARP inhibitor, reduced infarct size by a comparable degree (38–48%). Thiemermann et al, "Inhibition of the Activity of Poly(ADP Ribose) Synthetase Reduces Ischemia-Reperfusion Injury in the Heart and Skeletal Muscle", Proc. Natl. Acad. Sci. USA, 94:679–83 (1997). These results make it reasonable to suspect that PARP inhibitors could salvage previously ischemic heart or skeletal muscle tissue.

PARP activation can also be used as a measure of damage following neurotoxic insults following over-exposure to any of glutamate (via NMDA receptor stimulation), reactive oxygen intermediates, amyloid β-protein, N-methyl-4-phenyl-1,2,3,6-tetrahydropyridine (PTP) or its active metabolite N-methyl-4-phenylpyridine ($MPP^+$), which participate in pathological conditions such as stroke, Alzheimer's disease and Parkinson's disease. Zhang et al., "Poly (ADP-Ribose) Synthetase Activation: An Early Indicator of Neurotoxic DNA Damage", J. Neurochem., 65:3, 1411–14 (1995). Other studies have continued to explore the role of PARP activation in cerebellar granule cells in vitro and in MPTP neurotoxicity. Cosi et al., "Poly(ADP-Ribose) Polymerase (PARP) Revisited. A New Role for an Old Enzyme: PARP Involvement in Neurodegeneration and PARP Inhibitors as Possible Neuroprotective Agents", Ann. N. Y. Acad. Sci., 825:366–79 (1997); and Cosi et al., "Poly(ADP-Ribose) Polymerase Inhibitors Protect Against MPTP-induced Depletions of Striatal Dopamine and Cortical Noradrenaline in C57B1/6 Mice", Brain Res., 729:264–69 (1996). Excessive neural exposure to glutamate, which serves as the predominate central nervous system neurotransmitter and acts upon the N-methyl-D-aspartate (NMDA) receptors and other subtype receptors, most often occurs as a result of stroke or other neurodegenerative processes. Oxygen deprived neurons release glutamate in great quantities during ischemic brain insult such as during a stroke or heart attack. This excess release of glutamate in turn causes over-stimulation (excitotoxicity) of N-methyl-D-aspartate (NMDA), AMPA, Kainate and MGR receptors, which open ion channels and permit uncontrolled ion flow (e.g., $Ca^{2+}$ and $Na^+$ into the cells and $K^+$ out of the cells) leading to overstimulation of the neurons. The overstimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Glutamate exposure and stimulation has also been implicated as a basis for compulsive disorders, particularly drug dependence. Evidence includes findings in many animal species, as well as in cerebral cortical cultures treated with glutamate or NMDA, that glutamate receptor antagonists (i.e., compuonds which block glutamate from binding to or activating its receptor) block neural damage following vascular stroke. Dawson et al., "Protection of the Brain from Ischemia", Cerebrovascular Disease, 319–25 (H. Hunt Batjer ed., 1997). Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of this theory, has been difficult. Moreover, many of the compositions that are effective in blocking the receptors are also toxic to animals. As such, there is presently no known effective treatment for glutamate abnormalities.

The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of NNOS in vitro. Dawson et al., "Nitric Oxide Mediates Glutamate Neurotoxicity in Primary Cortical Cultures", Proc. Natl. Acad. Sci. USA, 88:6368–71 (1991); and Dawson et al., "Mechanisms of Nitric Oxide-mediated Neurotoxicity in Primary Brain Cultures", J. Neurosci., 13:6, 2651–61 (1993), Dawson et al., "Resistance to Neurotoxicity in Cortical Cultures from Neuronal Nitric Oxide Synthase-Deficient Mice", J. Neurosci., 16:8, 2479–87 (1996), Iadecola, "Bright and Dark Sides of Nitric oxide in Ischemic Brain Injury", Trends Neurosci., 20:3, 132–39 (1997), Huang et al., "Effects of Cerebral Ischemia in Mice Deficient in Neuronal Nitric Oxide Synthase", Science, 265:1883–85 (1994), Beckman et al., "Pathological Implications of Nitric Oxide, Superoxide and Peroxynitrite Formation", Biochem. Soc. Trans., 21:330–34 (1993), and Szabó et al., "DNA Strand Breakage, Activation of Poly (ADP-Ribose) Synthetase, and Cellular Energy Depletion are Involved in the Cytotoxicity in Macrophages and Smooth Muscle Cells Exposed to Peroxynitrite", Proc. Natl. Acad. Sci. USA, 83:1753–58 (1996).

It is also known that PARP inhibitors, such as 3-amino benzamide, affect DNA repair generally in response, for example, to hydrogen peroxide or gamma-radiation. Cristovao et al., "Effect of a Poly(ADP-Ribose) Polymerase Inhibitor on DNA Breakage and Cytotoxicity Induced by Hydrogen Peroxide and γ-Radiation," Terato., Carcino., and Muta., 16:219–27 (1996). Specifically, Cristovao et al. observed a PARP-dependent recovery of DNA strand breaks in leukocytes treated with hydrogen peroxide.

PARP inhibitors have been reported to be effective in radiosensitizing hypoxic tumor cells and effective in preventing tumor cells from recovering from potentially lethal damage of DNA after radiation therapy, presumably by their ability to prevent DNA repair. U.S. Pat. Nos. 5,032,617, 5,215,738; and 5,041,653.

Evidence also exists that PARP inhibitors are useful for treating inflammatory bowel disorders, such as colitis. Salzman et al., "Role of Peroxynitrite and Poly(ADP-Ribose) Synthase Activation Experimental Colitis," Japanese J. Pharm., 75, Supp. 1:15 (1997). Specifically, Colitis was induced in rats by intralluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon. See also, Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", Br. J. Pharm., 117:619–32 (1996); and Szabó et al., "Mercaptoethylguanidine and Guanidine Inhibitors of Nitric Oxide Synthase React with Peroxynitrite and Protect Against Peroxynitrite-induced Oxidative Damage", J. Biol. Chem., 272:9030–36 (1997).

Evidence also exists that PARP inhibitors are useful for treating arthritis. Szabó et al., "Protective Effects of an Inhibitor of Poly(ADP-Ribose)Synthetase in Collagen-Induced Arthritis," Japanese J. Pharm., 75, Supp. 1:102 (1997); Szabó et al., "DNA Strand Breakage, Activation of Poly(ADP-Ribose)Synthetase, and Cellular Energy Depletion are Involved in the Cytotoxicity in Macrophages and Smooth Muscle Cells Exposed to Peroxynitrite," Proc. Natl. Acad. Sci. USA, 93:1753–58 (March 1996); and Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone (INH2BP)", Intl. J. Oncol., 8:239–52 (1996); and Hughes et al., "Induction of T Helper Cell Hyporesponsiveness in an Experimental Model of Autoimmunity by Using Nonmitogenic Anti-CD3 Monoclonal Antibody", J. Immuno., 153:3319–25 (1994).

Further, PARP inhibitors appear to be useful for treating diabetes. Heller et al., "Inactivation of the Poly(ADP-Ribose)Polymerase Gene Affects Oxygen Radical and Nitric Oxide Toxicity in Islet Cells," J. Biol. Chem., 270:19, 11176–80 (May 1995). Heller et al. used cells from mice with activated PARP genes and found that these mutant cells did not show $NAD^+$ depletion after exposure to DNA-damaging radicals. The mutant cells were also found to be more resistant to the toxicity of NO.

PARP inhibitors have been shown to be useful for treating endotoxic shock or septic shock. Zingarelli et al., "Protective Effects of Nicotinamide Against Nitric Oxide-Mediated Delayed Vascular Failure in Endotoxic Shock: Potential Involvement of PolyADP Ribosyl Synthetase," Shock, 5:258–64 (1996), suggests that inhibition of the DNA repair cycle triggered by poly(ADP ribose) synthetase has protective effects against vascular failure in endotoxic shock. Zingarelli et al. found that nicotinamide protects against delayed, NO-mediated vascular failure in endotoxic shock. Zingarelli et al. also found that the actions of nicotinamide may be related to inhibition of the NO-mediated activation of the energy-consuming DNA repair cycle, triggered by poly(ADP ribose) synthetase. Cuzzocrea, "Role of Peroxynitrite and Activation of Poly(ADP-Ribose) Synthetase in the Vascular Failure Induced by Zymosan-activated Plasma," Brit. J. Pharm., 122:493–503 (1997).

PARP inhibitors have been used to treat cancer. Suto et al., "Dihydroisoquinolinones: The Design and Synthesis of a New Series of Potent Inhibitors of Poly(ADP-Ribose) Polymerase", Anticancer Drug Des., 7:107–17 (1991). In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly(ADP-ribose) Polymerase, on Cultured Tumor Cells", Oncol. Res., 6:9, 399–403 (1994), discusses the inhibition of PARP activity, reduced proliferation of tumor cells, and a marked synergistic effect when tumor cells are co-treated with an alkylating drug.

Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs. Mao et al., Pain, 72:355–366 (1997).

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related muscular degeneration, immune senescence, AIDS, and other immune senescence diseases; and to alter gene expression of senescent cells. WO 98/27975.

Large numbers of known PARP inhibitors have been described in Banasik et al., "Specific Inhibitors of Poly (ADP-Ribose) Synthetase and Mono(ADP-Ribosyl)-Transferase", J. Biol. Chem., 267:3, 1569–75 (1992), and in Banasik et al., "Inhibitors and Activators of ADP-Ribosylation Reactions", Molec. Cell. Biochem., 138:185–97 (1994). However, effective use of these PARP inhibitors, in the ways discussed above, has been limited by the concurrent production of unwanted side-effects (Milan et al., "Inhibitors of Poly(Adenosine Diphosphate-Ribose) Synthesis: Effect on Other Metabolic Processor", Science, 223:589–91 (1984)).

In addition to the above, PARP inhibitors have been disclosed and described in the following international patent applications: WO 00/42040; WO 00/39070; WO 00/39104; WO 99/11623; WO 99/11628; WO 99/11622; WO 99/59975; WO 99/11644; WO 99/11945; WO 99/11649; and WO 99/59973.

A recent comprehensive review of the state of the art has been published by Li and Zhang in IDrugs 2001, 4(7): 804–812 (PharmaPress Ltd ISSN 1369-7056).

There continues to be a need for effective and potent PARP inhibitors which produce minimal side-effects. The present invention provides compounds, compositions for, and methods of, inhibiting PARP activity for treating and/or preventing cellular, tissue and/or organ damage resulting from cell damage or death due to, for example, necrosis or apoptosis. The compounds and compositions of the present invention are specifically useful in ameliorating, treating and/or preventing neural tissue or cell damage, including that following focal ischemia and reperfusion injury. Generally, inhibition of PARP activity spares the cell from energy loss, preventing irreversible depolarization of the neurons and, thus, provides neuroprotection. While not wishing to be bound by any mechanistic theory, the inhibition of PARP activity by use of the compounds, compositions and methods of the present invention is believed to protect cells, tissue and organs by protection against the ill-effects of reactive free radicals and nitric oxide. The present invention therefore also provides methods of treating and/or preventing cells, tissue and/or organs from reactive free radical and/or nitric oxide induced damage or injury.

SUMMARY OF THE INVENTION

The present invention provides compounds described herein, derivatives thereof and their uses to inhibit poly (ADP-ribose) polymerase ("PARP"), compositions containing these compounds and methods for making and using these PARP inhibitors to treat, prevent and/or ameliorate the effects of the conditions described herein.

The compounds of the present invention are broadly described by the following Formula I:

I

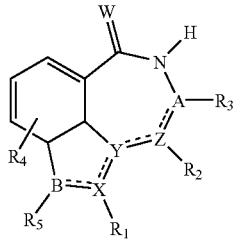

where

A is N, C, $CH_2$ or CH;

B is C, N, NH, S, SO or $SO_2$;

W is S or O;

X is C, CH, or N;

Y is carbon or N;

Z is C, $CH_2$, N, C═O;

preferably, provided that at least one of X, Y or Z is nitrogen;

$R_1$, $R_2$, $R_3$ and $R_5$, when present, are independently H, —OH, ═O or an optionally substituted alkyl, alkenyl, alkynyl, alkoxy, carboxy cycloalkyl, heterocycloalkyl, aryl, heteroaryl, halogen, amine, —$COR_8$, where $R_8$ is H, —OH an optionally substituted alkyl, alkenyl, alkynyl, alkoxy, carboxy cycloalkyl, heterocycloalkyl, aryl or heteroaryl, or —$OR_6$ or —$NR_6R_7$ where $R_6$ and $R_7$ are each independently hydrogen or an optionally substituted alkyl, alkenyl, alkynyl, cycloalkyl, heterocycloalkyl, aryl or heteroaryl; and when any of $R_1$, $R_2$, $R_3$ and $R_5$ may additionally be connected to the ring through a straight or branched $C_1$–$C_4$ alkyl which may additionally contain 1 or 2 double or triple bonds; and when any of A, X or Z is carbon, any of the attached $R_1$, $R_2$, and $R_3$ may additionally be independently selected from halogen, cyano or oxygen; and $R_4$ is, when present, 1–3 substituents which may be independently selected from hydrogen, halogen or alkyl.

In preferred embodiments, the present invention provides compounds, compositions and methods of making and using the following:

I-1

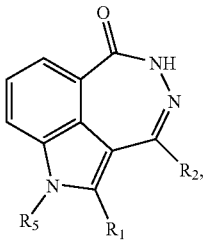

-continued

I-2

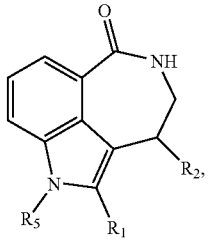

I-3a

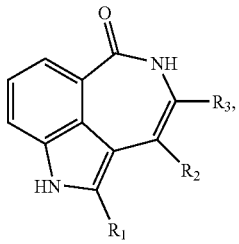

I-3b

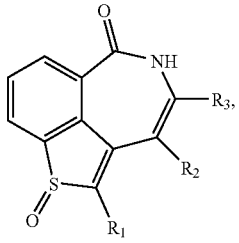

I-3c

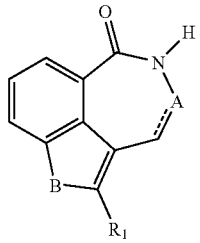

I-3d

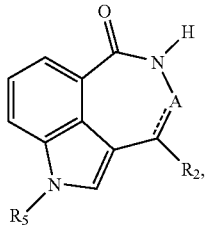

I-3e

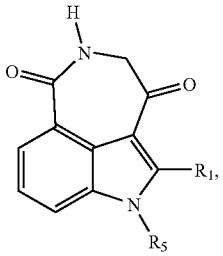

-continued

I-4

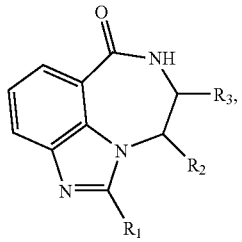

II-5

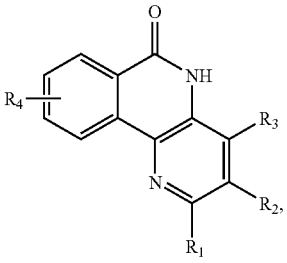

II-6

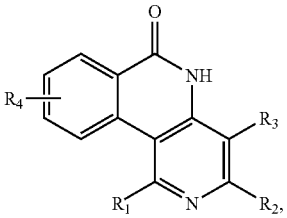

I-7a

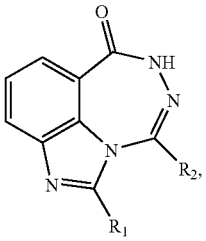

I-7b

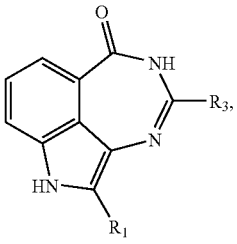

I-8

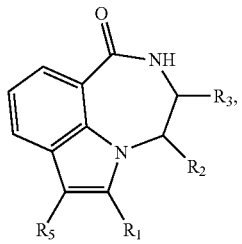

-continued

II-9

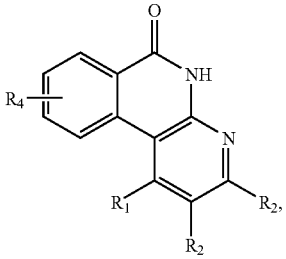

II-10

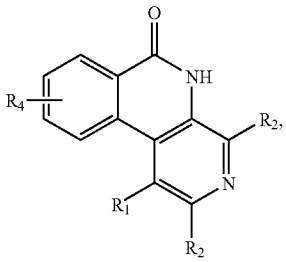

I-11

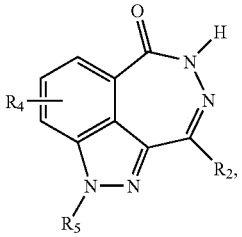

and

I-12

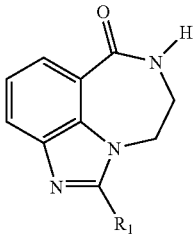

wherein $R_1$–$R_5$ are as described herein.

DETAILED DESCRIPTION

Figure 1:
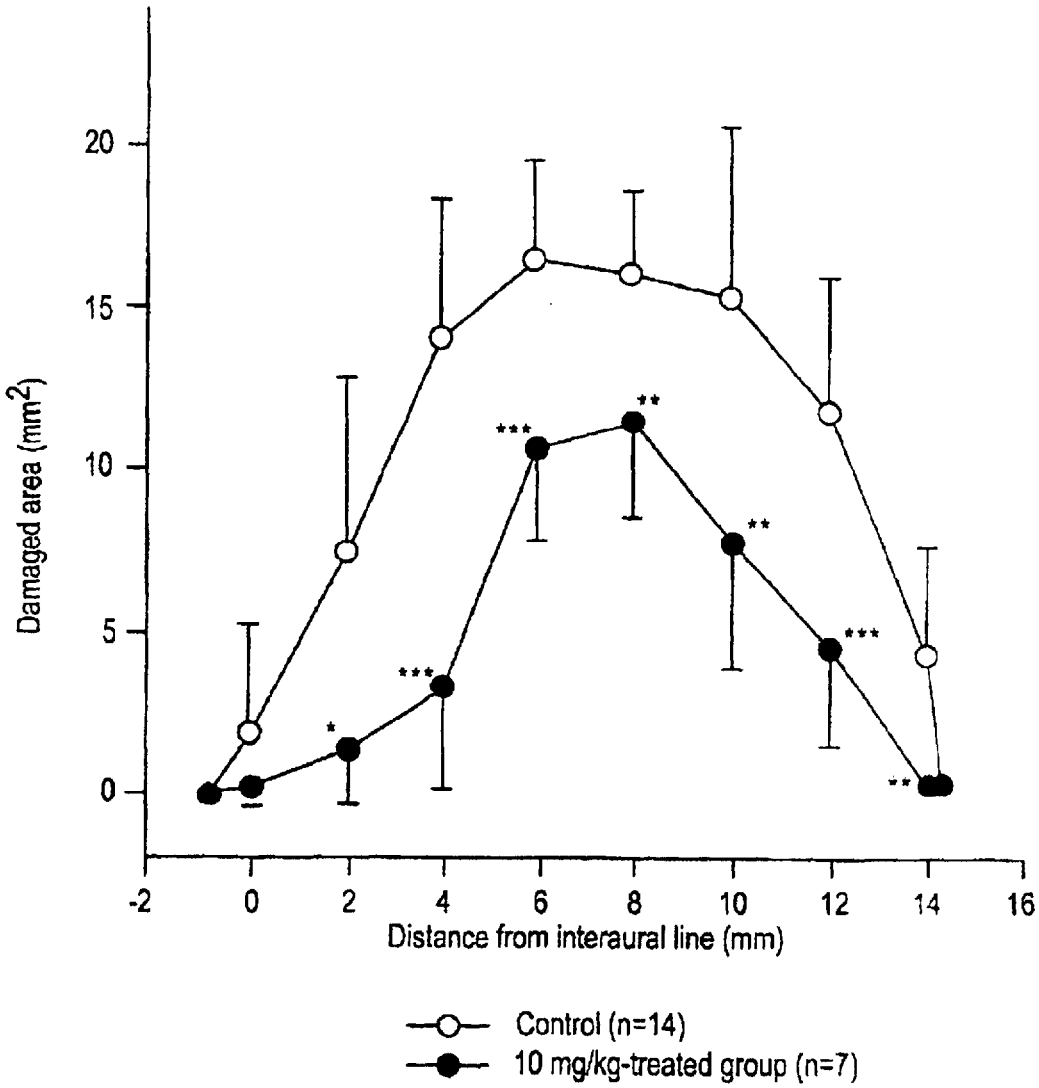
FIG. 1 shows the distribution of the cross-sectional infarct area at representative levels along the rostrocaudal axis, as measured from the interaural line in non-treated animals and in animals treated with 10 mg/kg of 3,4-dihydro-5-[4-(1-piperidinyl)-botoxyl]-1(2H)-isoquinolinone.

The present invention pertains to compounds, pharmaceutical compositions containing the same, methods of using the same, and process of making the same, including methods of making medicaments containing the compounds described herein for use in the described methods, wherein such compounds are useful as inhibitors of poly(ADP-ribose) polymerase (PARP). As such, they treat or prevent neural tissue damage resulting from cell damage or death due to necrosis or apoptosis, cerebral ischemia and reperfusion injury ore neurodegenerative diseases in an animal; they extend the lifespan and proliferative capacity of cells and thus can be used to treat or prevent diseases associated therewith; they alter gene expression of senescent cells; and they radiosensitize hypoxic tumor cells. Preferably, the compounds of the invention treat or prevent tissue damage resulting from cell damage or death due to necrosis or apoptosis, and/or effect neuronal activity, either mediated or not mediated by NMDA toxicity. These compounds are thought to interfere with more than the glutamate neurotoxicity and NO-mediated biological pathways. Further, the compounds of the invention can treat or prevent other tissue damage related to PARP activation. The present invention provides compounds which inhibit poly(ADP-ribose) polymerase ("PARP"), compositions containing these compounds and methods for using these PARP inhibitors to treat, prevent and/or ameliorate the effects of the conditions described herein.

In one embodiment, the present invention provides compounds of formula I:

I

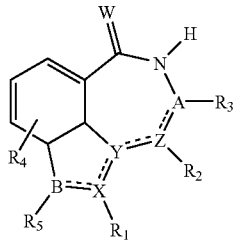

where

A is N, C, $CH_2$ or CH,

B is C, N, NH, S, SO or $SO_2$;

W is S or O;

X is C, CH, or N;

Y is carbon or N;

Z is C, $CH_2$, N, C═O;

preferably provided that at least one of X, Y or Z is nitrogen;

$R_1$, $R_2$, $R_3$ and $R_5$, when present, are independently H, —OH, ═O, or an optionally substituted alkyl, alkenyl, alkynyl, alkoxy, carboxy, cycloalkyl, heterocycloalkyl, aryl, heteroaryl, halogen, amine, —$COR_8$, where $R_8$ is H, —OH, an optionally substituted alkyl, alkenyl, alkoxy, carboxy, alkynyl, cycloalkyl, heterocycloalkyl, aryl or heteroaryl, or —$OR_6$ or —$NR_6R_7$ where $R_6$ and $R_7$ are each independently hydrogen or an optionally substituted alkyl, alkenyl, alkynyl, cycloalkyl, heterocycloalkyl, aryl or heteroaryl; and any of $R_1$, $R_2$, $R_3$ and $R_5$ may additionally be connected to the ring through a straight or branched $C_1$–$C_4$ alkyl which may additionally contain 1 or 2 double or triple bonds; and when any of A, X or Z is carbon, any of the attached $R_1$, $R_2$, and $R_3$ may additionally be independently selected from halogen, cyano or oxygen; and $R_4$ is, when present, 1–3 substituents which are independently selected from hydrogen, halogen or alkyl.

In an alternate embodiment, at least one of $R_1$, $R_2$, $R_3$ and $R_5$ is a solubilizing group which increases by 10 fold the solubility of the compound of formula I in water at 25° C. as compared to the compound of formula I in the absence of said solubilizing group and X, Y and Z may all be other than N or at least one of X, Y or Z may be N.

In yet another embodiment, the present invention provides a compound of the following formula:

II-5

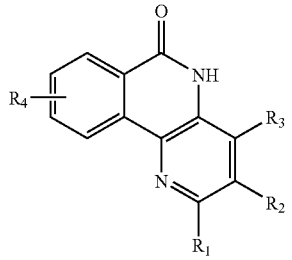

wherein $R_1$, $R_2$ and $R_3$ when present, are independently H, halogen, amino, hydroxy, halogen-substituted amino, —O-alkyl, —O-aryl, or an optionally substituted alkyl, alkenyl, alkynyl, alkoxy, carboxy, cycloalkyl, heterocycloalkyl, aryl, heteroaryl, —$COR_8$, where $R_8$ is H, —OH an optionally substituted alkyl, alkoxy, alkenyl, alkynyl, cycloalkyl, heterocycloalkyl, aryl or heteroaryl, or —$OR_6$ or —$NR_6R_7$ where $R_6$ and $R_7$ are each independently hydrogen or an optionally substituted alkyl, alkenyl, alkynyl, cycloalkyl, heterocycloalkyl, aryl or heteroaryl; and $R_4$ is, when present, independently selected from hydrogen, halogen, alkoxy or alkyl. In one embodiment, $R_4$ is halogen, such as fluorine and optionally only one $R_4$ is present on the ring.

In a further embodiment of the present invention, a compound of the following formula is provided:

II-6

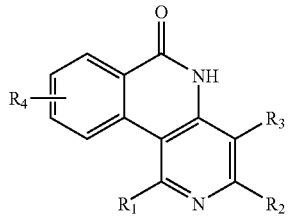

wherein $R_1$, $R_2$ and $R_3$, when present, are, independently, H, amino, hydroxy, halogen-substituted amino, —O-alkyl, —O-aryl, or an optionally substituted alkyl, alkenyl, alkyl, alkoxy, carboxy, cycloalkyl, heterocycloalkyl, aryl, heteroaryl, —$COR_8$, where $R_8$ is H, —OH, an optionally substituted alkyl, alkenyl, alkynyl, cycloalkyl, heterocycloalkyl, aryl or heteroaryl, or —$OR_6$ or —$NR_6R_7$ where $R_6$ and $R_7$ are each independently hydrogen or an optionally substituted alkyl, alkenyl, alkynyl, cycloalkyl, heterocycloalkyl, aryl or heteroaryl; and $R_4$ is, when present, is independently selected from hydrogen, halogen, alkoxy or alkyl. In one embodiment, $R_4$ is halogen, such as fluorine and optionally only one $R_4$ is present on the ring.

The invention further provides compositions, preferably pharmaceutical compositions, which contains a pharmaceutically acceptable carrier or diluent and at least one compound disclosed herein.

In preferred embodiments, the present invention provides compounds, compositions and methods of making and using the following:

I-1
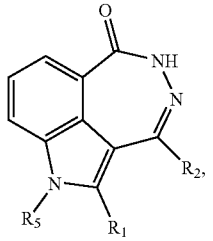
preferably, wherein $R_1$ is absent;
I-2
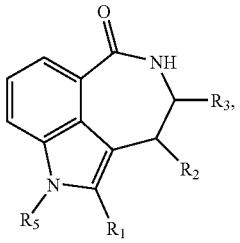
preferably wherein $R_3$ is absent, alternatively, preferably where $R_3$ is absent, $R_2$ is =O and/or $R_5$ is H;
I-3a
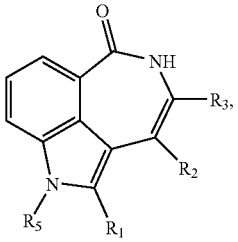
I-3b
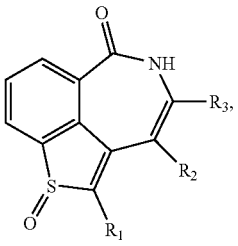
preferably wherein $R_3$ is absent
I-3c
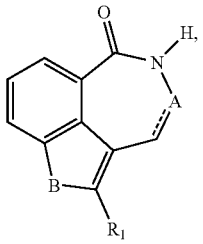
-continued
I-3d
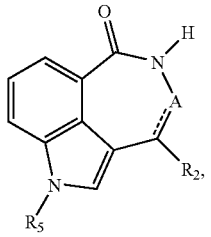
I-3e
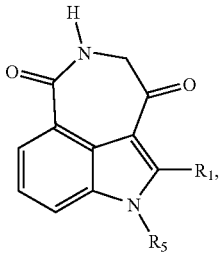
I-4
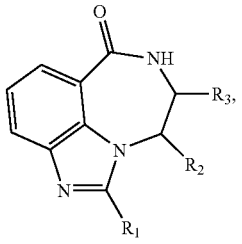
preferably wherein either or both of $R_2$ and $R_3$ is absent;
II-5
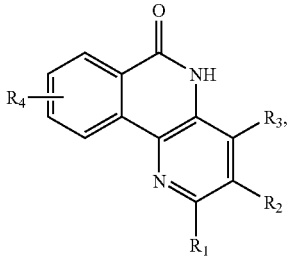
preferably wherein $R_4$ is absent;
II-6
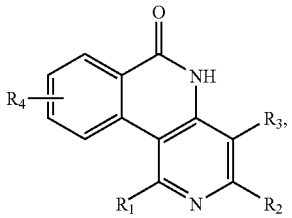

-continued

I-7a

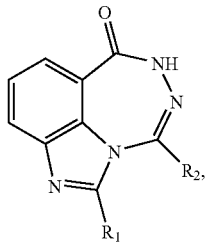

I-7b

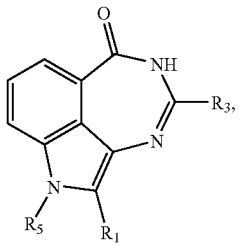

preferably wherein $R_3$ is absent;

I-8

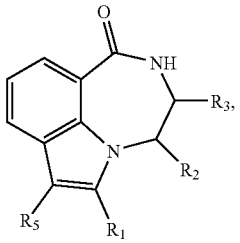

preferably wherein any one of $R_2$, $R_3$ and $R_5$ is absent; and,

II-9

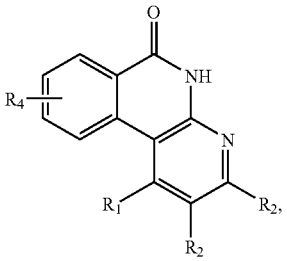

II-10

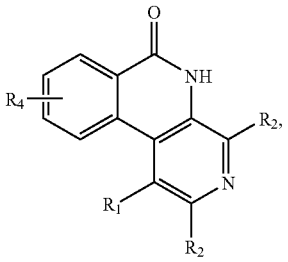

-continued

I-11

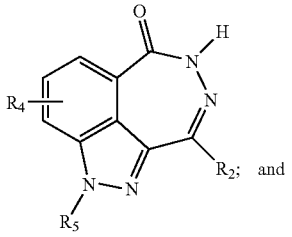

I-12

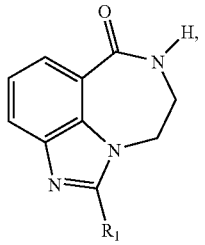

wherein $R_1$–$R_5$ are as described herein. Any of $R_1$, $R_2$, $R_3$, and/or $R_5$ may additionally be defined as any of $R_9C(O)OR_9$, $R_9C(O)OR_{10}$, $R_9OR_9N(R_9R_9)$, $R_9OR_9N(R_9(R_9R_{10}))$, $R_9OR_9$, $R_9OR_{10}$, $R_9R_{10}C(O)OR_9$, $R_{10}C(O)OR_{10}$, $R_9R_{10}OR_9N(R_9R_9)$, $R_9R_{10}OR_9N(R_9(R_9R_{10}))$, $R_9R_{10}OR_9$, $R_9R_{10}OR_{10}$, $R_9N(R_9R_9)R_9N(R_9R_9)$, $R_9N(R_9R_9)R_9N(R_9R_{10})$, $R_9N(R_9R_9)R_9N(R_{10}R_{10})$, wherein $R_9$, when present, may be individually selected from H, a bond, straight or branched alkyl ($C_1$–$C_6$) Or straight or branched alkenyl ($C_2$–$C_6$) and $R_{10}$ may be H, straight or branched alkyl ($C_1$–$C_6$) or straight or branched alkenyl ($C_1$–$C_6$) or an individually substituted or unsubstituted aryl, heteroaryl, cycloalkyl or heterocycloalkyl.

The present invention includes compounds of formula I-1 wherein when $R_2$ and $R_3$ are hydrogen, $R_1$ is not hydrogen or bromine or halogen. The present invention includes compounds of formula I-2 wherein $R_1$, $R_2$, $R_3$ and $R_5$ are not all hydrogen. The present invention includes compounds of formula I-2 wherein when $R_5$ and $R_3$ is hydrogen, $R_1$ is not halogen when $R_2$ is hydrogen, and $R_2$ is not phenyl when $R_1$ is hydrogen. The present invention includes compounds of formula I-4 wherein when $R_2$ and $R_3$ are hydrogen, $R_1$ is not methyl or ethyl. The present invention includes compounds of formula II-5, II-9 and II-10 wherein $R_1$, $R_2$ and $R_4$ are not all hydrogen. The present invention includes compounds of formula II-6 wherein $R_1$, $R_2$ and $R_4$ are not all hydrogen. The present invention includes compounds of formula I-8 wherein $R_1$, $R_2$, $R_3$ and $R_5$ are not all hydrogen.

Compositions containing these preferred and alternate embodiments and methods of making and using the same, as described herein, are also preferred.

Preferred compounds of the present invention include compounds of Formula I-1 wherein $R_1$ and $R_2$ are individually either absent or individually selected from halogen, alkoxy, carboxy, amine, an ester, an ether; straight or branched alkylamino, straight or branched alkylaminoalkylamino, alkoxy, aryloxy, optionally substituted cycloalkyl, heterocycloalkyl, aryl, heteroaryl, —$COR_8$, wherein $R_8$ is an optionally substituted alkyl, aryl or heteroaryl; straight or branched alkyl, alkenyl or alkynyl, straight or branched alkylaryl, optionally substituted aryl containing 1 or 2 fused aryl or aryl and cycloalkyl rings; and optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula I-1 by a straight or branched alkyl, alkenyl, or alkynyl. $R_5$ is optionally absent or H, straight or branched alkyl, carbonyl, alkoxy, caroxy, amine, alkenyl or alkynyl, an ester, an ether, optionally substituted aryl containing 1 or 2 fused aryl or aryl and cycloalkyl rings; optionally substituted cycloalkyl, heterocycloalkyl, aryl, heteroaryl, —$COR_8$, wherein $R_8$ is an optionally substituted alkyl, aryl or heteroaryl; an optionally substituted heteroaryl or heterocyclic rings containing 1, 2 or 3 heteroatoms and 1 or 2 fused rings, the heteroatoms being selected from O, S and N, wherein the aryl, cycloalkyl, heteroaryl or heterocycle described in the present disclosure may be optionally connected to the compound of formula I-1 or to each other by a straight or branched alkyl or a bond. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl, and straight or branched alkylheterocycle.

Preferred compounds of the present invention include compounds of Formula I-2 wherein $R_2$ is =O or —OH or alkoxy, such as methoxy, ethoxy, propoxy etc.; $R_1$ and $R_3$ are individually either absent or individually selected from halogen; straight or branched alkylamino, straight or branched alkylaminoalkylamino, alkoxy, aryloxy, straight or branched alkyl, straight or branched alkylaryl, optionally substituted aryl containing 1 or 2 fused aryl or aryl and cycloalkyl rings; and optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula I-2 by a straight or branched alkyl, alkenyl, or alkynyl; $R_5$ is optionally absent or H, straight or branched alkyl, carbonyl, optionally substituted aryl containing 1 or 2 fused aryl or aryl and cycloalkyl rings; an optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula I-2 by a straight or branched alkyl. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl, and straight or branched alkylheterocycle.

Preferred compounds of the present invention include compounds of Formulas I-3a and I-3b wherein $R_1$, $R_2$ and $R_3$ are individually either absent or individually selected from halogen; straight or branched alkylamino, straight or branched alkylaminoalkylamino, alkoxy, aryloxy, straight or branched alkyl, straight or branched alkylaryl, optionally substituted aryl containing 1 or 2 fused aryl or aryl and cycloalkyl rings; and optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula I-3a or I-3b by a straight or branched alkyl, alkenyl, or alkynyl, $R_5$ is optionally absent or H, straight or branched alkyl, carbonyl, optionally substituted aryl containing 1 or 2 fused aryl or aryl and cycloalkyl rings; an optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula I-3a or I-3b by a straight or branched alkyl. Optional substituents of the rings include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention include compounds of Formula I-3c wherein B is S, SO or $SO_2$; $R_1$ is optionally substituted alkyl, alkenyl, alkynyl, alkoxy, carboxy, cycloalkyl, heterocycloalkyl, aryl, heteroaryl, halogen, —$COR_8$, wherein $R_8$ is H, —OH, an optionally substituted alkyl, alkoxy, or —$OR_6$, wherein $R_6$ is hydrogen, or an optionally substituted alkyl; and A is N, C, CH or $CH_2$. A of Formula I-3c is preferably N or $CH_2$. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention included compounds of Formula I-3d wherein $R_1$, $R_2$ and $R_5$ are, independently, hydrogen, halogen, hydroxy, an optionally substituted alkyl, alkenyl, alkynyl, alkoxy, carboxy, an ester, an ether, cycloalkyl, heterocycloalkyl, aryl, or heteroaryl; —$COR_8$, where $R_8$ is H, —OH, an optionally substituted alkyl, alkoxy, or —$OR_6$ where $R_6$ is independently hydrogen or an optionally substituted alkyl; and A is C, CH or $CH_2$. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention included compounds of formula I-3e wherein $R_1$ and/or $R_5$ are, independently, halogen, H, OH, =O or an optionally substituted alkyl, alkenyl, alkenyl, alkynyl, cycloalkyl, heterocycloalkyl, aryl, heteroaryl, —$COR_8$, where $R_8$ is H, —OH, an optionally substituted alkyl, alkenyl, alkynyl, cycloalkyl, heterocycloalkyl, aryl or heteroaryl, or —$OR_6$ or —$NR_6R_7$ where $R_6$ and $R_7$ are each independently hydrogen or an optionally substituted alkyl, alkenyl, alkynyl, cycloalkyl, heterocycloalkyl, aryl or heteroaryl. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention include compounds of Formulas I-4 wherein $R_1$, $R_2$ and $R_3$ are individually either absent or individually selected from halogen; straight or branched alkylamino, straight or branched alkylaminoalkylamino, alkoxy, aryloxy, straight or branched alkyl, straight or branched alkylaryl, optionally substituted aryl containing 1 or 2 fused aryl or aryl and cycloalkyl rings; and optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula I-4 by a straight or branched alkyl, alkenyl, or alkynyl. Optional substituents as described herein include halogen, amino, carbonyl, hydroxyl, nitro, nitroso, straight or branched alkylamino, straight or branched alkylaminoalkylamino, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention include compounds of Formulas II-5, II-9, II-10 and II-6 wherein $R_1$ and $R_2$ are individually either absent or individually selected from halogen; straight or branched alkylamino, straight or branched alkylaminoalkylamino, alkoxy, aryloxy, straight or ranched alkyl, straight or branched alkylaryl, optionally substituted aryl containing 1 or 2 fused aryl or aryl and cycloalkyl rings; and optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula II-5, II-9, II-10 or II-6 by a straight or branched alkyl, alkenyl, or alkynyl. $R_4$ is as defined herein. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention include compounds of Formula I-7a and I-7b wherein $R_1$, $R_2$ and $R_3$ are individually either absent or individually selected from halogen; straight or branched alkylamino, straight or branched alkylaminoalkylamino, alkoxy, aryloxy, straight or branched alkyl, straight or branched alkylaryl, optionally substituted aryl containing 1 or 2 fused aryl or aryl and cycloalkyl rings; and optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compounds of formula I-7a and I-7b by a straight or branched alkyl, alkenyl, or alkynyl. $R_5$ is optionally absent or H, straight or branched alkyl, carbonyl, optionally substituted aryl containing 1 or 2 fused aryl or aryl and cycloalkyl rings; an optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compounds of formulas I-7a and I-7b by a straight or branched alkyl. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention include compounds of Formula I-8 wherein $R_1$, $R_2$ and $R_3$ are individually either absent or individually selected from halogen; straight or branched alkylamino, straight or branched alkylaminoalkylamino, alkoxy, aryloxy, straight or branched alkyl, straight or branched alkylaryl, optionally substituted aryl containing 1 or 2 fused aryl or aryl and cycloalkyl rings; and optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compound of formula I-8 by a straight or branched alkyl, alkenyl, or alkynyl. $R_5$ is optionally absent or H, straight or branched alkyl, carbonyl, optionally substituted aryl containing 1 to 2 fused aryl or aryl and cycloalkyl rings; an optionally substituted heteroaryl or heterocyclic rings containing 1, 2 or 3 heteroatoms and 1 or 2 fused rings, the heteroatoms being selected from O, S and N, wherein the aryl, heteroaryl or heterocycle may be optionally connected to the compounds of formula I-8 by a straight or branched alkyl. Optional substituents as described herein include halogen, amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention include compounds of formula I-11 wherein $R_2$ is halogen, amine, —$COR_8$ wherein $R_8$ is an optionally substituted alkyl, aryl or heteroaryl or an optionally substituted alkyl, alkenyl, alkynyl, alkoxy, carboxy, cycloalkyl, heterocycloalkyl, aryl or heteroaryl. Optional substituents as described herein include halogen amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferred compounds of the present invention include compounds of formula I-12 wherein $R_1$ is a halogen, amine, or an optionally substituted alkyl, alkenyl, alkynyl, alkoxy, carboxy, cycloalkoxy, heterocycloalkyl, aryl or heteroaryl. Optional substituents as described herein include halogen amino, carbonyl, hydroxyl, nitro, nitroso, straight or branched alkylamino, straight or branched alkylaminoalkylamino, straight or branched alkylthioalkylamino, straight or branched alkylthioalkylaryl, alkoxy, aryloxy, straight or branched alkyl, straight or branched alkylaryl, straight or branched alkylheteroaryl, aryl, heteroaryl, cycloalkyl, heterocycloalkyl and straight or branched alkylheterocycle.

Preferably, the compounds of the invention exhibit an $IC_{50}$ for inhibiting PARP in vitro, as measured by the methods described herein, of about 100 μM, or less, preferably less than about 50 μM, more preferably less than about 10 μM, or less than 1 μM, most preferably less than about 0.1 μM.

Specific embodiments of the present invention include the compounds shown below in the examples and Table III, and neutral and/or salt forms thereof, as well as enantiomer and racemic mixtures thereof, where appropriate.

Broadly, the compounds and compositions of the present invention can be used to treat or prevent cell damage or death due to necrosis or apoptosis, cerebral ischemia and reperfusion injury or neurodegenerative diseases in an animal, such as a human. The compounds and compositions of the present invention can be used to extend the lifespan and proliferative capacity of cells and thus can be used to treat or prevent diseases associated therewith; they alter gene expression of senescent cells; and they radiosensitize hypoxic tumor cells. Preferably, the compounds and compositions of the invention can be used to treat or prevent tissue damage resulting from cell damage or death due to necrosis or apoptosis, and/or effect neuronal activity, either mediated or not mediated by NMDA toxicity. The compounds of the present invention are not limited to being useful in treating glutamate mediated neurotoxicity and/or NO-mediated biological pathways. Further, the compounds of the invention can be used to treat or prevent other tissue damage related to PARP activation, as described herein.

The present invention provides compounds which inhibit the in vitro and/or in vivo polymerase activity of poly(ADP-ribose) polymerase (PARP), and compositions containing the disclosed compounds.

The present invention provides methods to inhibit, limit and/or control the in vitro and/or in vivo polymerase activity of poly(ADP-ribose) polymerase (PARP) in any of solutions, cells, tissues, organs or organ systems. In one embodiment, the present invention provides methods of limiting or inhibiting PARP activity in a mammal, such as a human, either locally or systemically.

The present invention provides methods to treat and/or prevent diseases, syndromes and/or conditions exacerbated by or involving the increased generation of PARP. These methods involve application or administration of the compounds of the present invention to cells, tissues, organs or organ systems of a person in need of such treatment or prevention.

In one embodiment, the present invention provides methods to treat and/or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse and these methods involve administration of the compounds and compositions of the present invention preferably prior to, or immediately subsequent to reperfusion, such that reperfusion injury is prevented, treated or reduced. The present invention also provides methods of preventing and/or treating vascular stroke, cardiovascular disorders.

In another embodiment the present invention provides in vitro or in vivo methods to extend or increase the lifespan and/or proliferation capacity of cells and thus also methods to treat and/or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related muscular degeneration, immune senescence, AIDS and other immune senescence diseases, and other diseases associated with cellular senescence and aging, as well as to alter the gene expression of senescent cells.

In a further embodiment, the present invention provides methods of treating or preventing or ameliorating the effect of cancer and/or to radiosensitize hypoxic tumor cells to render the tumor cells more susceptible to radiation therapy and thereby to prevent the tumor cells from recovering from potentially lethal damage of DNA after radiation therapy. A method of this embodiment is directed to specifically and preferentially radiosensitizing tumor cells rendering the tumor cells more susceptible to radiation therapy than non-tumor cells.

In yet another embodiment the present invention provides methods of preventing and/or treating vascular stroke, cardiovascular disorders; to treat other conditions and/or disorders such as age-related muscular degeneration, AIDS and other immune senescence diseases, inflammation, arthritis, gout, atherosclerosis, cachexia, cancer, degenerative diseases of skeletal muscle involving replicative senescence, diabetes, head trauma, spinal chord injury, immune senescence, gout, inflammation, inflammatory bowel disorders (such as colitis and Crohn's disease), acute pancreatitis, mucositis, hemorrhagic shock, splanchnic artery occlusion shock, multiple organ failure (such as involving any of the kidney, liver, renal, pulmonary, retinal, pancreatic and/or skeletal muscles systems), acute autoimmune thyroiditis, muscular dystrophy, osteoarthritis, osteoporosis, chronic and/or acute pain (such as neuropathic pain), renal failure, retinal ischemia, septic shock (such as endotoxic shock), local and/or remote endothelial cell dysfunction (such are recognized by endo-dependent relaxant responses and up-regulation of adhesion molecules), inflammation and skin aging.

The compounds of the present invention may be administered, for example, parenterally, to a person diagnosed with acute retinal ischemia or acute vascular stroke, either by intermittent or continuous intravenous administration, by either a single dose or a series of divided doses. Compounds of the invention may be used in combination or sequentially. The compound of the invention can be administered by intermittent or continuous administration via implantation of a biocompatible, biodegradable polymeric matrix delivery system containing a compound of formula I, I-1, I-2, I-3a, I-3b, I-3c, I-3d, I-3e, I-4, II-5, II-6, II-9, II-10, I-7a, I-7b, I-8, I-11 or I-12 or via a subdural pump inserted to administer the compound directly to the infarct area of the brain.

In a further embodiment, the present invention provides methods to extend the lifespan and proliferative capacity of cells, such as, for example, in using the compounds of the invention as general mediators in the generation of oxidants, proinflammatory mediators and/or cytokines, and/or general mediators of leukocyte infiltration, calcium ion overload, phospholipid peroxidation, impaired nitric oxide metabolism and/or reduced ATP production.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The compounds of the present invention can also be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related muscular degeneration, immune senescence, AIDS and other immune senescence diseases, and other diseases associated with cellular senescence and aging, as well as to alter the gene expression of senescent cells. These compounds can also be used to treat cancer and to radiosensitize hypoxic tumor cells to render the tumor cells more susceptible to radiation therapy and to prevent the tumor cells from recovering from potentially lethal damage of DNA after radiation therapy, presumably by their ability to prevent DNA repair. The compounds of the present invention can be used to prevent or treat vascular stroke; to treat or prevent cardiovascular disorders; to treat other conditions and/or disorders such as age-related muscular degeneration, AIDS and other immune senescence diseases, inflammation, arthritis, gout, atherosclerosis, cachexia, cancer, degenerative diseases of skeletal muscle involving replicative senescence diabetes, head trauma, immune senescence, gout, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging.

Preferably, the compounds of the invention act as PARP inhibitors to treat or prevent tissue damage resulting from cell death or damage due to necrosis or apoptosis; to treat or prevent neural tissue damage resulting from cerebral ischemia and reperfusion injury or neurodegenerative diseases in an animal; to extend and increase the lifespan and proliferative capacity of cells; to alter gene expression of senescent cells; and to radiosensitize tumor cells.

Another especially preferred embodiment of the invention is a pharmaceutical composition which comprises (i) a therapeutically effective amount of the compound of formula I, I-1, I-2, I-3a, I-3b, I-3c, I-3d, I-3e, I-4, II-5, II-6, II-9, II-10, I-7a, I-7b, I-8; I-11 or I-12 and (ii) a pharmaceutically acceptable carrier.

As used herein, "alkyl" means, unless stated otherwise, a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

Optional substituents of alkyl chains include mercapto, carboxy, hydroxy, or phenyl, benzyl, or phenylethyl, which may themselves be substituted by hydroxy, halo, methoxy, $C_1$–$C_6$ alkyl, amine and carboxy.

"Alkenyl" means, unless stated otherwise, a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy", means the group —OR where R is alkyl as herein defined. Preferably, R is a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless otherwise indicated.

"Amino" compounds include amine ($NH_2$) as well as substituted amino groups comprising alkyls of one through six carbons. Alkylamino compounds include secondary and tertiary amines substituted with alkyl groups of, for example, $C_1$–$C_6$alkyl. Alkylaminoalkyl and alkylaminoalkylamino are secondary and tertiary amino groups and alkyl chains with multiple amino groups within the alkyl chain.

"aryl" or "heteroaryl" means a moiety which is substituted or unsubstituted, especially a cyclic or fused cyclic ring and includes a mono-, bi-, or tricyclic, carbo- or heterocyclic ring(s), such as a 3, 4, 5, 6, 7 or 8 membered ring, wherein the ring is either unsubstituted or substituted in, for example, one to five position(s) with halo, haloalkyl, hydroxyl, nitro, trifluoromethyl, $C_1$–$C_6$ straight or branched chain alkyl, $C_2$–$C_6$ straight or branched chain alkenyl, $C_1$–$C_6$ alkoxy, —C(O)—O($C_1$–$C_6$ alkyl), carboxy, $C_2$–$C_6$ alkenyloxy, phenoxy, benzyloxy, amino, thiocarbonyl, ester, thioester, cyano, imino, alkylamino, aminoalkyl, sulfhydryl, thioalkyl, and sulfonyl; wherein the individual ring sizes are preferably 5–8 members; wherein the heterocyclic ring contains 1–4 heteroatom(s) selected from the group consisting of O, N, or S or their mixture; wherein aromatic or tertiary alkyl amines are optionally oxidized to a corresponding N-oxide. Heteroaryls may be attached to other rings or substituted through the heteroatom and/or carbon atom of the ring and aryls and heteroaryls may be multiply linked 2 and/or 3 together through, for example, alkyl or alkenyl (straight or branched, such as $C_1$ to $C_6$) chains, as opposed to, or in addition to being fused. Similarly, aryls and heteroaryls may be attached to the core compound through, for example, alkyl or alkenyl (straight or branched, such as $C_1$ to $C_6$) chains. Particularly preferred aryl or heteroaryl moieties include but are not limited to phenyl, benzyl, naphthyl, piperidino, pyrrolyl, pyrrolidinyl, pyridinyl, pyrimidinyl, purinyl, quinolinyl, isoquinolinyl, furyl, thiophenyl, imidazolyl, oxazolyl, thiazolyl, pyrazolyl, and thienyl.

"Phenyl" includes all possible isomeric phenyl radicals, optionally monosubstituted or multi-substituted with substituents selected from the group consisting of amino, carboxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, sulfonyl, hydroxy, halo, haloalkyl, $NR_2$ wherein $R_2$ is selected from the group consisting of hydrogen, ($C_1$–$C_6$)-straight or branched chain alkyl, ($C_3$–$C_6$) straight of branched chain alkenyl or alkynyl and 2, 3 or 4 fused phenyl rings.

Cycloalkyl optionally containing at least one heteroatom, to form a heterocyclic ring, includes saturated $C_2$–$C_8$ rings, preferably $C_5$ or $C_6$ rings, wherein at 1, 2, 3 or 4 heteroatoms selected from O, N or S may be optionally substituted for a carbon atom of the ring. Cycloalkyls optionally containing at least one heteroatom, as described above, may be substituted by or fused to at least one 5 or 6 membered aryl or heteroaryl and/or substituted by at least one of amino, $C_1$–$C_5$ straight or branched chain alkyl, $C_1$–$C_6$ alkanol, $C_1$–$C_6$ straight or branched chain alkylamino, $C_1$–$C_6$ alkoxy, or $C_1$–$C_6$ alkenyl, or benzyl, or phenyl or phenylethyl wherein the ring may be substituted as described above for substitutions of "Phenyl". Heterocycloalkyls may be attached to other rings or substituted through the heteroatom and/or carbon atom of the ring and cycloalkyls and heterocycloalkyls may be multiply linked 2 and/or 3 together through, for example, alkyl or alkenyl (straight or branched, such as $C_1$ to $C_6$) chains, as opposed to, or in addition to being fused. Similarly, cycloalkyls and heterocycloalkyls may be attached to the core compound through, for example, alkyl or alkenyl (straight or branched, such as $C_1$ to $C_6$) chains.

Preferred cycloalkyls containing at least one or two heteroatom include

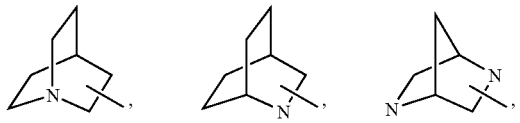

pyrrolidinyl, imidazolidinyl, pyrazolidinyl, piperidinyl, piperazinyl, morpholino and thiomorpholino.

The compounds of the present invention may possess one or more asymmetric center(s) and thus can be produced as mixtures (racemic and non-racemic) of stereoisomers, or as individual enantiomers or diastereomers. The individual stereoisomers may be obtained by using an optically active starting material, by resolving a racemic or non-racemic mixture of an intermediate at some appropriate stage of the synthesis, or by resolution of the compound of any of formulas formula I, I-1, I-2, I-3a, I-3b, I-3c, I-3d, I-4, II-5, II-6, II-9, II-10, I-7a, I-7b, I-8, I-11 or I-12. It is understood that the individual stereoisomers as well as mixtures (racemic and non-racemic) of stereoisomers are encompassed by the scope of the present invention.

The compounds of the invention are useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the invention. In practice, the use of these forms amounts to use of the neutral compound.

"Pharmaceutically acceptable salt", "hydrate", "ester" or "solvate" refers to a salt, hydrate, ester, or solvate of the inventive compounds which possess the desired pharmacological activity and which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane-propionate, digluconate, dodecylsulfate, ethanesulfonate, fumarate, glucoheptanoate, glycerophosphate, hemisulfate, heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxymethyl)aminoethane; and the like. See, for example, "Pharmaceutical Salts," J. Pharm. Sci., 66:1, 1–19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a PARP inhibitor of the present invention in an aqueous or an aqueous alcohol solution or other suitable solvent containing the appropriate acid or base, and isolating the salt by evaporating the solution. Alternatively, the free base of the PARP inhibitor of the present invention can be reacted with an acid, as well as reacting the PARP inhibitor having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objectives(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burger's Medicinal Chemistry and Drug Chemistry, Fifth Ed., Vol. 1, pp. 172–178, 949–982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since most drugs undergo metabolic transformation of some kind, the biochemical reactions that play a role in drug metabolism may be numerous and diverse. The main site of drug metabolism is the liver, although other tissues may also participate.

The term "neurodegenerative diseases" includes Alzheimer's disease, Parkinson's disease and Huntington's disease.

The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed as having a neurodegenerative disease or who are at risk of developing a neurodegenerative disease. The term also encompasses preventing further neurodegeneration in patients who are already suffering from or have symptoms of a neurodegenerative disease.

The term "treating" refers to:

(i) preventing a disease, disorder or condition from occurring in an animal that may be predisposed to the disease, disorder and/or condition, but has not yet been diagnosed as having it;

(ii) inhibiting the disease, disorder or condition, i.e., arresting its development; and (iii) relieving the disease, disorder or condition, i.e., causing regression of the disease, disorder and/or condition.

The term "neural tissue damage resulting from ischemia and reperfusion injury and neurodegenerative diseases" includes neurotoxicity, such as seen in vascular stroke and global and focal ischemia.

A feature characteristic of many of these transformations is that the metabolic products are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are each transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the Table II. Phase I (or functionalization) reactions generally consist of (1) oxidative and reductive reactions that alter and create new functional groups and (2) hydrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

Table II

Phase I Reactions (functionalization reactions):

(1) Oxidation via the hepatic microsomal P450 system:
Aliphatic oxidation
Aromatic hydroxylation
N-Dealkylation
O-Dealkylation
S-Dealkylation
Epoxidation
Oxidative deamination
Sulfoxide formation
Desulfuration
N-Oxidation and N-hydroxylation
Dehalogenation (2) Oxidation via nonmicrosomal mechanisms:
Alcohol and aldehyde oxidation
Purine oxidation
Oxidative deamination (monoamine oxidase and diamine oxidase)

(3) Reduction:
Azo and nitro reduction (4) Hydrolysis:
Ester and amide hydrolysis
Peptide bond hydrolysis
Epoxide hydration Phase II Reactions (conjugation reactions);

(1) Glucuronidation
(2) Acetylation
(3) Mercapturic acid formation
(4) Sulfate conjugation
(5) N-, O-, and S-methylation
(6) Trans-sulfuration The compounds of the present invention exhibit pharmacological activity and are, therefore, useful as pharmaceuticals. In particular, the compounds exhibit central nervous and cardiac vesicular system activity.

It is understood that tautomeric forms, when possible, are included in the invention.

Many of the PARP inhibitors of the present invention can be synthesized by known methods from starting materials that are known.

Typically, the PARP inhibitors used in the composition of the invention will have an $IC_{50}$ for inhibiting poly(ADP-ribose) polymerase in vitro of about 20 μM or less, preferably less than about 10 μM, more preferably less than about 1 μM or preferably less than about 0.1 μM most preferably less than about 0.01 μM.

The PARP inhibitor 3,4-dihydro-5-[4-(1-piperidinyl) butoxy]-1(2H)-isoquinolinone, for example, has been reported to inhibit PARP with an $IC_{50}$ of 40 nM by Suto et al., cited above.

Compounds of the present invention may be prepared as follows.

EXAMPLE 1

Compounds of the following general formula I-1 may be prepared, for example, by the following methods.

Scheme 1-1

I-1

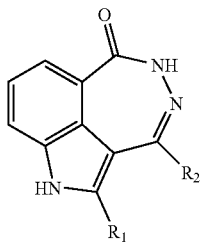

Scheme 1 below illustrates schematically the preparation of Example compounds 1 through 6.

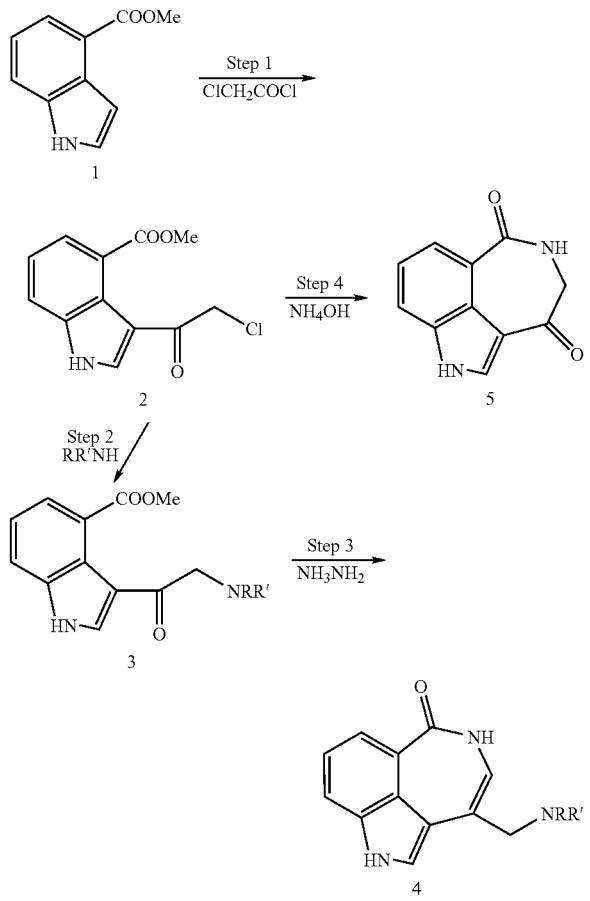

Step 1

Methyl indole-4-carboxylate 1 (7.2 g, 41.09 mmol, commercially available) was dissolved in dry $CH_2Cl_2$ (220 mL). To this stirred solution was added $ZnCl_2$ (11.53 g, 84.64 mmol). The mixture was cooled down to 0° C. and added slowly $CH_3MgBr$ (5.39 g, 45.19 mmol). It was stirred at 0° C. for 15 min. and at room rt. for 1 h. To this mixture was added chloro acetyl chloride and stirred for 2 h. $AlCl_3$ was then added and the mixture was run for an additional 18 h. The reaction mixture was cooled to 0° C. and washed with cold water (60 mL) and extracted with some additional $CH_2Cl_2$ (2×60 mL). The organic layer was washed with brine, dried over $MgSO_4$, and concentrated to dryness. The crude solid residues were triturated in ether to give a nice off-white solid 2 (5.1 g) which was used in the next step with no further purification. $^1H$ NMR (300 Hz, $d_6$-DMSO) 12.3 (s, 1H), 8.5 (m, 1H), 7.66 (m, 1H), 7.32 (m, 2H), 4.89 (s, 2H), 3.78 (s, 3H).

Step 2

To the suspension of the α-chloro ketone 2 (10 mmol) in ethanol (50 mL) was added $K_2CO_3$ (10 mmol) and a secondary amine (30 mmol). The mixture was heated to 40–70° C. with stirring for 1.5 h. The solution was cooled to rt. and the solvent was removed in vacuo. The mixture extracted with water and EtOAc. The organic layer was collected, washed with brine, dried over $MgSO_4$, and concentrated to dryness. The crude was purified by crystallization to give a desired product without further purification. For example, a morpholine derivative 3 was prepared in the following: To the suspension of the α-chloro ketone (2.50 g, 9.93 mmol) in ethanol (50 mL) was added $K_2CO_3$ (1.51 g, 10.92 mmol) and morpholine (2.59 g, 29.79 mmol). The mixture was heated with stirring to 70° C. for 1.5 h. The solution was cooled to rt. and concentrated by vacuum evaporator. The mixture was washed with water (30 mL) and extracted with EtOAc (3×50 mL). The organic layer was washed with brine, dried over $MgSO_4$, and concentrated to dryness. The crude product was triturated in ether to give a nice white solid (1.72 g). This material was used in the next step without any further purification. MS ES+=303, ES−=301. $^1H$ NMR (300 Hz, $d_6$-DMSO) 12.1 (bs, 1H), 8.48 (s, 1H), 7.63 (m, 1H), 7.28 (m, 2H), 3.75 (s, 3H), 3.58 (m, 6H), 3.38 (m, 4H).

Step 3

The final product 4 can be easily prepared by condensing of the compound 3 with hydrazine. For example, to the solution containing ethanol (8 mL) and hydrazine (8 mL) was added the keto morpholine 3. The solution was heated to 110° C. for 1 h. The solution was stripped down by vacuum evaporator. The oil was washed with water (25 mL) and extracted with EtOAc (3×30 mL). The organic layer was washed with brine, dried over $MgSO_4$, and concentrated to dryness. The crude product was purified by silica gel column chromatography by use of the eluents 5–10% MeOH/$CH_2Cl_2$. The product was further cleaned by trituration in ether to give a pure yellow solid 4 (0.41 g). $^1H$ NMR (300 Hz, $d_6$-DMSO) 11.84 (s, 1H), 10.22 (s, 1H), 7.87 (s, 1H), 7.54 (m, 2H), 7.19 (t, 1H, J=7.7 Hz), 3.57 (m, 4H), 3.34 (m, 2H), 2.44 (bs, 4H).

Example 1-1

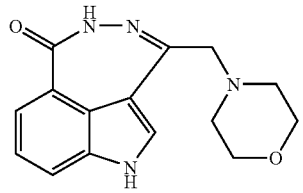

The compound was prepared as described in Scheme 1. $^1H$ NMR (400 Hz, $d_6$-DMSO) 11.84 (s, 1H), 10.22 (s, 1H), 7.87 (s, 1H), 7.54 (m, 2H), 7.19 (t, 1H, J=7.7 Hz), 3.57 (m, 4H), 3.34 (m, 2H), 2.44 (bs, 4H). Anal. ($C_{15}H_{16}N_4O_2$), C H N.

The HCl salt form: The cyclic morpholine (0.35 g, 1.23 mmol) was dissolved in THF (10 mL). To the solution was added slowly 4 M HCl in dioxane (1.41 mmol, 0.35 mL). The amine salt was crashed out of the solution which was collected by vacuum filtration. The solid material was quickly transferred to a storage vial due to its hygroscopic in nature. The product is a nice yellow solid (0.16 g). Mp.= 238–240° C. $^1H$ NMR (400 Hz, $d_6$-DMSO) 12.33 (s, 1H), 10.53 (s, 1H), 10.30 (s, 1H), 7.98 (d, 1H, J=2.9 Hz), 7.60 (m, 2H), 7.25 (t, 1H, J=7.8 Hz), 4.29 (s, 2H), 3.95 (s, 2H), 3.80 (bs, 2H), 3.56 (bs, 2H), 3.25 (bs, 2H). Anal. ($C_{15}H_{16}N_4O_2$, 1; HCl), C H N.

Example 2-1

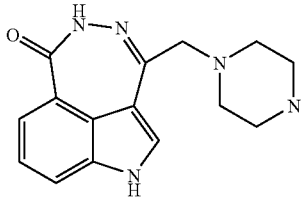

The compound was prepared as described in Scheme 1. Mp.=232–236° C. $^1$H NMR (400 Hz, $d_6$-DMSO) 11.88(s, 1H); 10.27(s, 1H); 7.91(s, 1H); 7.60–7.58(m, 2H); 7.23(t, 1H, J=7.84 Hz); 3.36(s, 2H); 2.56(s, 4H); 2.38(s, 4H); 2.20 (s, 3H); Anal. ($C_{16}H_{19}N_5O$), C H N.

Example 3-1

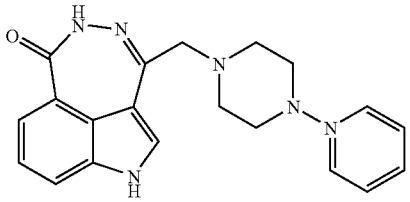

The compound was prepared as described in Scheme 1. Mp.=168–170° C. $^1$H NMR (400 Hz, $d_6$-DMSO) 11.85(s, 1H); 10.24(s, 1H); 8.10(d, 1H, J=4.7 Hz); 7.92(s, 1H); 7.55–7.49(m, 3H); 7.18(t, 1H, J=7.8 Hz); 6.81(d, 1H, J=8.6 Hz); 6.62(t, 1H, J=7.0 Hz); 3.37(s, 2H); 3.47(s, 4H); 2.56(s, 4H); Anal. ($C_{20}H_{20}N_6O$, $0.5H_2O$), C H N.

Example 4-1

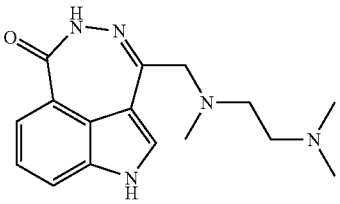

The compound was prepared as described in Scheme 1. Mp.=78–81° C. $^1$H NMR (400 Hz, $d_6$-DMSO) 10.93(s, 1H); 10.19(s, 1H); 8.00(s, 1H); 7.53(d, 2H); 7.17(t, 1H, J=7.8 Hz); 3.34(s, 4H); 2.39(s, 2H); 2.18(s, 3H); 2.14(s, 6H); Anal. ($C_{16}H_{21}N_5O$, 0.3; $H_2O$), C H N.

Example 5-1

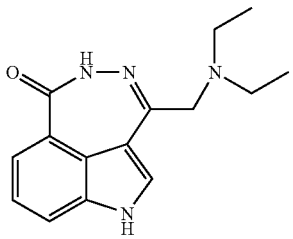

The compound was prepared as described in Scheme 1. Mp.=174–177° C. $^1$H NMR (400 Hz, $d_6$-DMSO) 11.78(s, 1H); 10.20(s, 1H); 7.85(s, 1H); 7.54(d, 2H); 7.16(t, 1H, J=7.8 Hz); 3.38(s, 2H); 2.52(m, 4H); 1.00(t, 6H, J=7.0 Hz); Anal. ($C_{15}H_{18}N_4O$, 0.5; $H_2O$), C H N.

Example 6-1

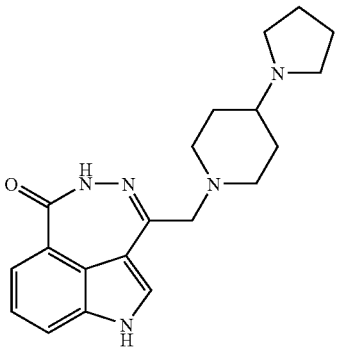

The compound was prepared as described in Scheme 1. Mp.=171–173° C. $^1$H NMR (400 Hz, $d_6$-DMSO) 11.81(s, 1H); 10.19(s, 1H); 7.87(s, 1H); 7.52(d, 2H); 7.17(t, 1H, J=7.8 Hz); 3.27(s, 2H); 2.89(d, 2H); 2.43(s, 4H); 2.00–21.89 (m, 3H); 1.79(d, 2H); 1.63(s, 4H); 1.33 (m, 2H); Anal. ($C_{20}H_{25}N_5O$, 0.6; $H_2O$), C H N.

EXAMPLE 2

Compounds of the following general formula I-2 may be synthesized, for example, as described above.

I-2

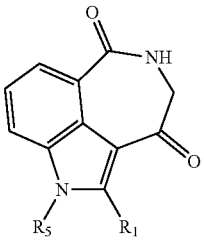

Example 1-2

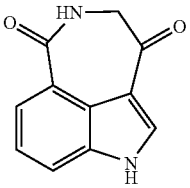

The compound was prepared as described in Step 4 of Scheme 1. A solution of the α-chloro ketone 2 (10 mmol) in concentrate ammonium hydroxide (5 mL) and 1,4 dioxane (15 mL) was heated at 70° C. for 3 hours with stirring. A white precipitate appeared and was collected by filtration to give a desired product 5 without further purification (40% yield. Mp.=300–305° C. $^1$H NMR (400 Hz, $d_6$-DMSO) 12.2 (s, 1H), 8.24 (s, 1H), 8.07 (bt, 1H), 7.92 (d, 1H, J=7.5 Hz), 7.76 (d, 1H, J=8.1 Hz), 7.38 (t, 1H, J=7.8 Hz), 3.93 (d, 2H); Anal. ($C_{11}H_8N_2O_2$), C H N.

Example 2-2

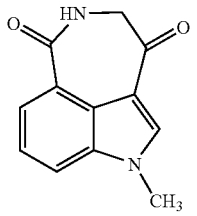

Similar to the procedure described in example 7, a solution of N-methyl α-chloro ketone (10 mmol) in concentrate ammonium hydroxide (5 mL) and 1,4 dioxane (15 mL) was heated at 70° C. for 3 hours with stirring. The solution was cooled to rt. and concentrated to 10 mL by vacuum evaporator. The mixture was partitioned between water (10 mL) and extracted with EtOAc (50 mL). The organic layer was collected and washed with brine, dried over $MgSO_4$, and concentrated to dryness. The crude product was purified by silica gel chromatography to give a white solid (60% yield). Mp.=215–217° C. $^1H$ NMR (400 Hz, $d_6$-DMSO) 8.27 (s, 1H), 8.07 (bt, 1H), 7.96 (d, 1H, J=7.5 Hz), 7.85 (m, 1H), 7.46 (t, 1H, J=7.9 Hz), 3.93 (m, 5H); Anal. ($C_{12}H_{10}N_2O_2$, 0.3; $C_4H_8O_2$), C H N.

EXAMPLE 3

Compounds of the following general formula I-3 may be synthesized, for example, as described below:

I-3a

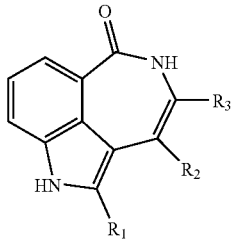

I-3b

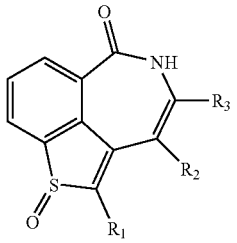

Scheme 1-3

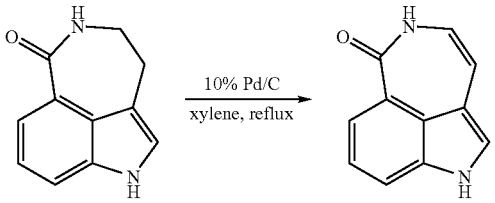

1 2

5,6-Dihydro-1H-azepino[5,4,3,-cd]indole-6-one (2). The suspension of 1[11] (450 mg, 2.42 mmol) in xylene (10 mL) was heated up to 90° C. and then Pd/C was added. The resulting mixture was refluxed for 3 hrs and then cooled to r.t. (room temperature). After the filtration, the filtrate was concentrated in vacuo to afford an orange solid. Purification of the solid via column chromatography (1% to 3% MeOH in $CH_2Cl_2$) afforded the product 2 as an orange solid (40 mg, 9%). Mp.>154° C. dec.; $^1H$ NMR ($CD_3OD$) d 7.69 (d, J=7.5 Hz, 1H), 7.48 (d, J=8.0 Hz, 1H), 7.16 (t, J=8.0 Hz, 1H), 7.09 (s, 1H), 5.77 (d, J=9.5 Hz, 1H), 5.53 (d, J=9.5 Hz, 1H); Anal. Calcd for $C_{11}H_8N_2O_1$.0.4; MeOH: C, 69.50; H, 4.91; N, 14.22. Found: C, 69.53; H, 4.58; N, 14.03. See, J. Med. Chem. 1990, 33, 633–641.

Scheme 2-3

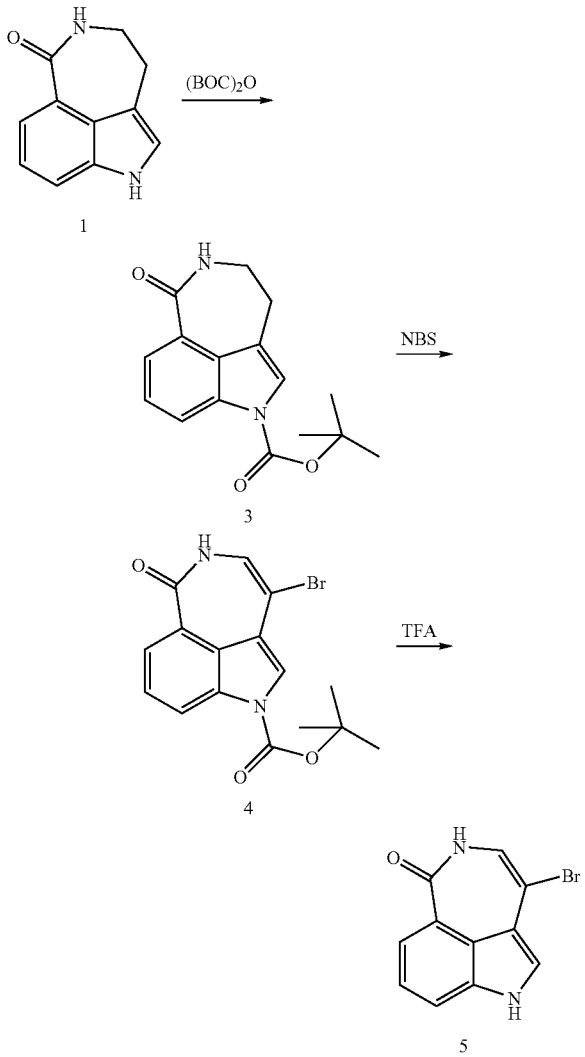

1 3 4 5

5,6-Dihydro-1-teterbutoxycarbamate-azepino[5,4,3,-cd] indole-6-one (3). To a suspension of 1 (340 mg, 1.83 mmol) in $CH_2CN$ (20 mL) was added $(BOC)_2O$ and DMAP under $N_2$ at r.t. The mixture was stirred continuously overnight. Solvent was removed. The residue was dissolved in EtOAc. The solution was washed with 1N HCl (2×15 mL) and brine, dried in $MgSO_4$ and filtered. The organic layer was concentrated in vacuo to afford a yellow solid. The purification of the solid via column chromatography (1% to 3% MeOH in $CH_2Cl_2$) gave 3 as a white solid (440 mg, 84%). Mp 167–168° C.; $^1H$ NMR ($CDCl_3$) d 8.33 (d, J=7.5 Hz, 1H), 8.08 (d, J=8.0 Hz, 1H), 8.02 (t, J=5.5, 6.0 Hz, 1H), 7.44 (s, 1H), 7.42 (t, J=8.0 Hz, 1H), 3.58 (q, J=6.0, 10, 5.5, 9.5 Hz, 2H), 3.01 (t, J=4.5, 4.0 Hz, 2H), 1.66 (s, 9H).

3-Bromo-5,6-dihydro-1-teterbutoxycarbamate-azepino[5,4,3,-cd]indole-6-one (4) To a solution of 3 (400 mg, 1.40 mmol) in $CCl_4$ (20 mL) was added NBS (261 mg, 1.47 mmol) and AIBN (20 mg) under $N_2$ at r.t. The resulting mixture was refluxed for 3 hrs. After cooled to r.t., the succinamide was filtered off, washed with $CCl_4$. The filtrate was concentrated in vacuo. The resulting residue was purified via column chromatography (20% to 50% EtOAc in hexanes) to afford 4 as a pale yellow solid(130 mg, 26%). $^1$H NMR ($CDCl_3$) d 8.24 (d, J=8.5 Hz, 1H), 7.99 (d, J=8.0 Hz, 1H), 7.45 (s, 1H), 7.31 (t, J=8.0 Hz, 1H), 6.11 (d, J=7.5 Hz, 1H), 1.61 (s, 9H).

3-Bromo-5,6-dihydro-1H-azepino[5,4,3,-cd]indole-6-one (5) To a solution of 4 (130 mg, 0.358 mmol) in $CH_2Cl_2$ (2 mL) was added TFA (2 mL) dropwise under $N_2$ at r.t. The resulting mixture was stirred continuously for 3 hrs. Solvent was removed. The residue was purified via column chromatography (0.5% to 2% MeOH in $CH_2Cl_2$) to afford an orange solid (10 mg, 10%). Mp 160–162° C. dec. $^1$H NMR ($CD_3OD$, 400 MHz) 7.57 (d, J=8.0 Hz, 1H), 7.35 (d, J=8.0 Hz, 1H), 7.06 (s, 1H), 7.05 (t, J=8.0 Hz, 1H), 5.80 (s, 1H); Anal: Calcd for $C_{11}H_7BrN_2O$.(0.12 EtOAc): C, 50.38; H, 2.93; N, 10.24. Found: C, 50; H, 3.01; N, 9.85.

EXAMPLE 4

Compounds of the following general formula I-4 may be synthesized, for example, as described below.

I-4

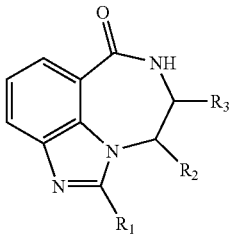

Scheme 1-4
General Synthesis of imidazo benzodiazepines;

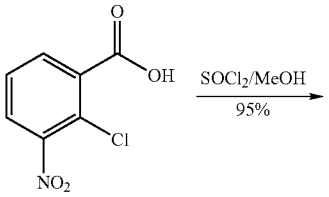

1

-continued

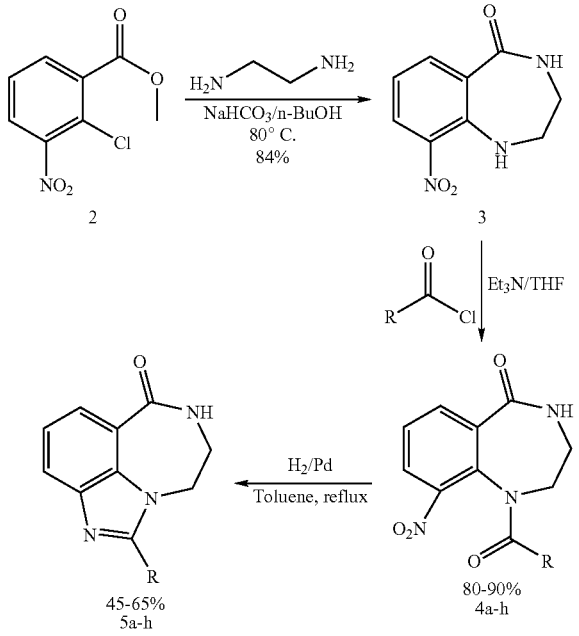

Synthesis of nitro amide 3. Ester 2 (1.0 g, 4.7 mmol), prepared according to literature,(Kukla, M. J.; Breslin, H. J.; Pawels, R.; Fedde, C. L.; Miranda, M.; Scott, M, K.; Sherrill, R. G.; Taeymaekers, A.; Van Gelder, J.; Andries, K.; Janssen, M. A. C.; De Clerq, E.; Jannsen, P. A. J., J. Med. Chem. 1991, 34, 746–751.) was dissolved in n-butanol (5 mL). Sodium carbonate (0.50 g, 4.7 mmol) was added to the solution followed by ethylene diamine (282 mg, 4.7 mmol). After several hours of heating at 80° C., an orange solid started to precipitate out of solution. The reaction was stopped after 16 h and the orange solid was filtered off and washed with water several times and recrystallized from EtOAc. The dry yield of the final orange crystals was 810 mg (84%). mp=187–190° C. (dec). $^1$H NMR ($d_6$-DMSO) δ 8.72 (t, 1H), 8.42 (t, 1H), 8.23 (d, 1H), 8.15 (d, 1H), 6.75 (t, 1H), 3.64 (m, 2H), 3.35 (m, 2H). Anal Calcd. for $C_9H_9N_3O_3$: C, 52.17; H, 4.38; N, 20.28 Found: C, 52.25; H, 4.59; N, 20.19.

General Procedure for the acylation of 3 (4a). A solution of compound 3 (460 mg, 2.22 mmol) was dissolved in THF (10 mL). Triethyl amine (340 μL, 2.44 mmol) was added to this solution followed by acetyl chloride (175 μL, 2.44 mmol). The solution was stirred overnight with gentle warming (50° C.). The reaction was quenched with water (10 mL) followed by extraction with EtOAc (3×10 mL). The combined organics were dried, concentrated and chromatographed on silica gel to yield compound 4a in 30% yield (160 mg). $^1$H NMR ($CDCl_3$) δ 8.13 (d, 1H), 8.06 (d, 1H), 7.72 (t, 1H), 6.96 (t, 1H), 4.97 (m, 2H), 3.36 (m, 2H), 2.25 (s, 3H). This material was used without further purification.

R=Phenyl (4b). $^1$H NMR ($CDCl_3$) δ 8.63 (bs, 1H), 8.40 (d, 1H), 8.06 (d, 1H), 7.60 (d, 2H), 7.52 (t, 1H), 7.42 (t, 2), 6.85 (t, 1H), 4.29 (m, 2H), 3.84 (m, 2H).

R=m-tolyl (4c). $^1$H NMR ($CDCl_3$) δ 8.65 (bs, 1H), 8.40 (d, 1H), 8.05 (d, 1H), 7.44 (s, 1H), 7.30 (m, 3H), 6.85 (t, 1H), 4.30 (m, 2H), 3.84 (m, 2H), 2.38 (s, 3H).

R=p-tolyl (4d). $^1$H NMR ($CDCl_3$) δ 8.64 (bs, 1H), 8.40 (d, 1H), 8.06 (d, 1H), 7.50 (d, 2H), 7.23 (d, 2H), 6.85 (t, 1H), 4.27 (m, 2H), 3.84 (m, 2H).

R=cinnamoyl (4e). $^1$H NMR ($CDCl_3$) δ 8.47 (bs, 1H), 8.40 (d, 1H), 8.15 (d, 1H), 7.85 (d, 1H), 7.63 (m, 3H), 7.40 (m, 3), 6.88 (t, 1H), 4.30 (m, 2H), 3.79 (m, 2H).

R=cyclohexyl (4f). $^1$H NMR ($CDCl_3$) δ 8.36 (d, 1H), 8.34 (s, 1H), 8.10 (d, 1H), 6.87 (t, 1H), 4.16 (m, 2H), 3.69 (m, 2H), 3.47 (m, 1H), 1.96 (m, 2H), 1.81 (m, 2H), 1.70 (m, 2H), 1.34 (m, 4H).

R=1-napthoyl (4g). $^1$H NMR ($CDCl_3$) δ 8.60 (bs, 1H), 8.36 (d, 1H), 8.04 (m, 1H), 7.91 (d, 1H), 7.85 (m, 2H), 7.50 (m, 2H), 7.44 (m, 2H), 6.77 (t, 1H), 4.45 (m, 2H), 3.93 (m, 2H).

R=2-napthoyl (4h). $^1$H NMR ($CDCl_3$) δ 8.69 (bs, 1H), 8.41 (d, 1H), 8.17 (s, 1H), 8.03 (d, 1H), 7.87 (m, 3H), 7.54 (m, 3H), 6.85 (t, 1H), 4.34 (m, 2H), 3.89 (m, 2H).

General Procedure for the cyclization of amides 4a–h (5a). The acetate 4a (100 mg, 0.40 mmol) was dissolved in a 1:1 mixture of EtOAc:MeOH (10 mL). This solution was degassed and added to a nitrogen containing Parr bomb with 10% Pd/C (25 mg). This solution was hydrogenated at 30 psi for 4 hours. The mixture was filtered through a plug of celite and concentrated. The crude material was dissolved in boiling toluene and refluxed for 12 h to induce cyclization. After cooling, the solution was concentrated and the product was recrystallized from EtOAc to yield 35 mg (44%) of the final product 5a. mp=>300° C. (dec). $^1$H NMR ($d_6$-DMSO) δ 8.35 (bt, 1H), 7.79 (d, 1H), 7.73 (d, 1H), 7.25 (t, 1H), 4.28 (m, 2H), 3.58 (m, 2H), 2.53 (s, 3H). Anal. Calcd. for $C_{11}H_{11}N_3O$: C, 62.84; H, 5.75; N, 19.99. Found: C, 62.43; H, 5.54; N, 19.43.

R=Phenyl (5b). mp=253–257° C.; $^1$H NMR ($d_6$-DMSO) δ 8.48 (bt, 1H), 7.89 (m, 4H), 7.59 (m, 3H), 7.37 (t, 1H), 4.47 (m, 2H), 3.54 (m, 2H). Anal. Calcd. for $C_{16}H_{13}N_3O$: C, 72.97; H, 4.98; N, 15.96. Found: C, 72.32; H, 5.06; N, 15.88.

R=m-tolyl (5c). mp=234–238° C.; $^1$H NMR ($d_6$-DMSO) δ 8.47 (bt, 1H), 7.89 (m, 2H), 7.70 (s, 1H), 7.65 (d, 1H), 7.47 (t, 1H), 7.36 (m, 2H), 4.47 (m, 2H), 3.54 (m, 2H), 2.43 (s, 3H). Anal. Calcd. for $C_{17}H_{15}N_3O$ (0.5 $H_2O$): C, 72.68; H, 5.53; N, 14.96. Found: C, 72.88; H, 5.58; N, 14.91.

R=p-tolyl (5d). mp=258–263° C.; $^1$H NMR ($d_6$-DMSO) δ 8.44 (t, 1H), 7.88 (m, 2H), 7.76 (d, 1H), 7.37 (m, 3H), 4.45 (m, 2H), 3.53 (m, 2H), 2.42 (s, 3H). Anal Calcd. for $C_{17}H_{15}N_3O$: C, 73.63; H, 5.45; N, 15.15. Found: C, 73.13; H, 5.49; N, 15.10.

R=phenylpropionyl (5e). mp=195–200° C.; $^1$H NMR ($d_6$-DMSO) δ 8.37 (t, 1H), 7.86 (t, 2H), 7.34 (m, 3H), 7.25 (m, 3H), 4.22 (m, 2H), 3.55 (m, 6H). Anal Calcd. for $C_{18}H_{17}N_3O$: C, 74.20; H, 5.88; N, 14.42. Found: C, 73.05; H, 6.04; N, 14.49.

R=cyclohexyl (5f). mp=263–266° C.; $^1$H NMR ($d_6$-DMSO) δ 8.35 (t, 1H), 7.77 (m, 2H), 7.25 (t, 1H), 4.35 (m, 2H), 3.57 (m, 2H), 2.94 (m, 1H), 1.94 (m, 2H), 1.81 (m, 2H), 1.71 (m, 1H), 1.58 (m, 2H), 1.41 (m, 1H), 1.29 (m, 1H). Anal Calcd. for $C_{16}H_{19}N_3O$: C, 70.18; H, 7.18; N, 15.34. Found: C, 70.73; H, 7.13; N, 15.22.

R=1-napthoyl (5g). mp=226–229° C.; $^1$H NMR ($d_6$-DMSO) δ 8.43 (t, 1H), 8.18 (d, 1H), 8.09 (d, 1H), 7.98 (m, 2H), 7.91 (d, 1H), 7.83 (d, 1H), 7.71 (t, 1H), 7.59 (m, 2H). 7.43 (t, 1H), 4.13 (m, 2H), 3.53 (m, 2H). Anal Calcd. for $C_{20}H_{15}N_3O$ (0.25 $H_2O$): C, 75.57; H, 4.92; N, 13.22. Found: C, 75.46; H, 4.87; N, 13.19.

R=2-napthoyl (5h). mp=261–265° C.; $^1$H NMR ($d_6$-DMSO) δ 8.52 (t, 1H), 8.47 (s, 1H), 8.11 (m, 2H), 8.03 (m, 2H), 7.95 (d, 1H), 7.91 (d, 1H), 7.65 (m, 1H), 7.40 (t, 1H), 4.59 (m, 2H), 3.57 (m, 2H). Anal Calcd. for $C_{20}H_{15}N_3O$ (1 $H_2O$): C, 72.49; H, 5.14; N, 12.68. Found: C, 72.23; H, 5.17; N, 12.65.

Scheme 2-4
General Synthesis of aminobenzodiazepine derivatives 5a-y

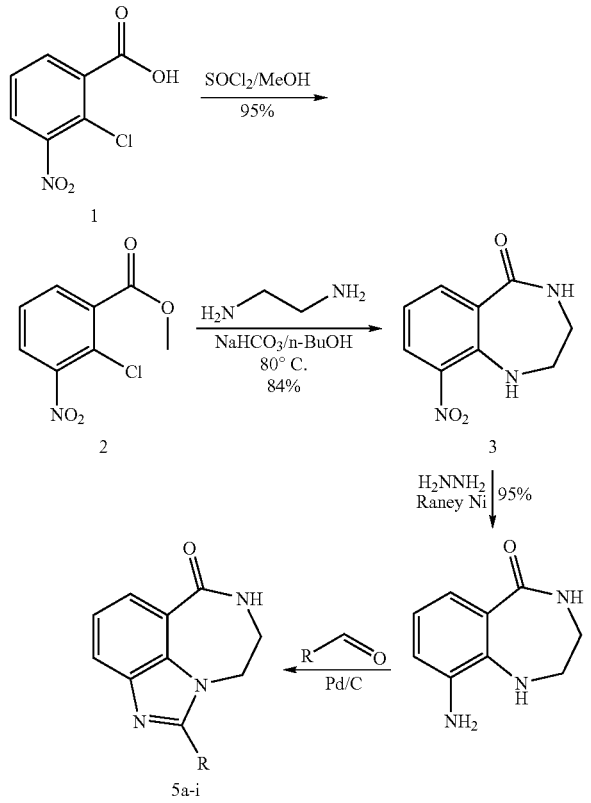

Synthesis of Aniline (4). Nitro amide 3 (1.8 g, 8.7 mmol) was dissolved in MeOH (125 mL) and heated to 40° C. Raney nickel (200 mg) was added to the solution followed by dropwise addition of hydrazine monohydrate (5 mL, xs). The reaction was heated to reflux for 30 minutes or until all of the starting material was gone then the mixture was filtered hot through a plug of celite to remove the residual nickel. The celite was washed with boiling MeOH (100 mL) and the filtrate was concentrated and dried in vacuo. The resulting air sensitive solid (1.45 g, 94%) was stored under nitrogen and an analytical sample could be obtained from trituration with diethyl ether. $^1$H NMR ($d_6$-DMSO) δ 7.91 (t, 1H), 7.03 (d, 1H), 6.69 (d, 1H), 6.47 (t, 1H), 4.97 (s, 2H), 4.64 (m, 2H), 3.20 (m, 2H).

General Procedure for synthesis of benzimidazoles 5a–ddd. The amine 4 (200 mg, 1.13 mmol), aldehyde (1.1 eq) and palladium on carbon (50 mg) were all mixed in MeOH (10 mL) and refluxed overnight. The reaction was filtered hot through a celite plug and the filtrate was concentrated in vacuo. The resulting solid was triturated with diethyl ether or EtOAc (5 mL) and filtered. Analytical samples of the final products could be obtained by recrystallization in EtOAc or EtOAc/MeOH.

R=H (5a). Yield=32%; mp=225–235° C. (dec); $^1$H NMR ($d_6$-DMSO) δ 8.45 (bt, 1H), 8.37 (s, 1H), 7.95 (m, 2H), 7.39 (t, 1H), 4.50 (m, 2H), 3.65 (m, 2H). Anal Calcd for $C_{10}H_9N_3O$ (0.75 $H_2O$) C, 59.84; H, 5.27; N, 20.94. Found: C, 59.69; H, 5.16; N, 20.73.

R=Benzyl (5b). Yield=52%; mp=224–227° C.; $^1$H NMR ($d_6$-DMSO) δ 8.53 (t, 1H), 8.02 (m, 2H), 7.47 9 m, 6H), 4.51 (m, 2H), 3.75 (m, 2H), 2.70 (m, 2H). Anal Calcd for $C_{17}H_{15}N_3O$ (0.25 $H_2O$) C, 72.45; H, 5.54; N, 14.91. Found: C, 72.89; H, 5.55; N, 14.86.

R=4-Fluorophenyl (5c). Yield=47%; mp=252–256° C.; $^1$H NMR ($d_6$-DMSO) δ 8.39 (t, 1H), 7.82 (m, 4H), 7.36 (t, 2H), 7.28 (t, 1H), 4.36 (m, 2H), 3.45 (m, 2H). Anal Calcd for $C_{16}H_{12}FN_3O$ (0.2 $H_2O$): C, 67.46; H, 4.39; N, 14.75. Found: C, 67.31; H, 4.27; N, 14.74.

R=3-Chlorophenyl (5d). Yield=50%; mp=265–267° C.; $^1$H NMR ($d_6$-DMSO) δ 8.47 (t, 1H), 7.87 (m, 4H), 7.63 (m, 2H), 7.38 (t, 1H), 4.48 (m, 2H), 3.35 (m, 2H). Anal Calcd for $C_{16}H_{12}ClN_3O$: C, 65.54; Cl, 11.91; H, 4.06; N, 14.11. Found: C, 64.30; Cl, 11.64; H, 4.13; N, 13.92.

R=4-Bromophenyl (5e). Yield=13%; mp=264–268° C.; $^1$H NMR ($d_6$-DMSO) δ 8.57 (t, 1H), 8.00 (m, 2H), 7.90 (m, 4H), 7.47 (t, 1H), 4.54 (m, 2H), 3.62 (m, 2H). Anal Calcd for $C_{16}H_{12}BrN_3O$: C, 55.00; H, 3.69; N, 12.03. Found: C, 55.42; H, 3.67; N, 11.97.

R=3,5-Difluorophenyl (5f). Yield=9%; mp=325–328° C.; $^1$H NMR ($d_6$-DMSO) δ 8.49 (s, 1H), 7.93 (t, 2H), 7.62 (d, 2H), 7.53 (m, 1H), 7.40 (m, 1H), 4.51 (m, 2H), 3.51 (m, 2H). Anal Calcd for $C_{16}H_{11}F_2N_3O$ (0.3 $H_2O$): C, 63.07; H, 3.84; N, 13.79. Found: C, 63.09; H, 3.86; N, 13.65.

R=2,4-dihydroxyphenyl (5g). Yield=61%; mp=325–330 (dec)° C.; $^1$H NMR ($d_6$-DMSO) δ 11.02 (s, 1H), 9.93 (s, 1H), 8.45 (t, 1H), 7.85 (t, 2H), 7.43 (d, 1H), 7.35 (t, 1H), 6.48 (s, 1H), 6.43 (d, 1H), 4.32 (m, 2H), 3.53 (m, 2H). Anal Calcd for $C_{10}H_9N_3O_2$ (0.5 $H_2O$): C, 63.15; H, 4.64; N, 13.81. Found: C, 63.02; H, 4.78; N, 13.55.

R=3,5-dihydroxyphenyl (5h). Yield=38%; mp=235–245° C.; $^1$H NMR ($d_6$-DMSO) δ 9.82 (s, 2H), 8.47 (t, 1H), 7.92 (m, 2H), 7.40 (t, 1H), 6.72 (s, 2H), 6.46 (s, 1H), 4.47 (m, 2H), 3.59 (m, 2H). Anal Calcd for $C_{10}H_9N_3O_2$ ($H_2O$): C, 61.34; H, 4.83; N, 13.41. Found: C, 61.56; H, 4.99; N, 13.36.

R=3,4,5-trihydroxyphenyl (5i). Yield=22%; mp=340–345° C.; $^1$H NMR ($d_6$-DMSO) δ 9.25 (s, 2H), 8.73 (s, 1H), 8.41 (t, 1H), 7.82 (t, 2H), 7.31 (t, 1H), 6.78 (s, 2H), 4.41 (m, 2H), 3.52 (m, 2H). Anal Calcd for $C_{10}H_9N_3O_2$ (0.5 $H_2O$): C, 60.00; H, 4.41; N, 13.12. Found: C, 59.92; H, 4.20; N, 12.92.

R=hydroxy (5j). Yield=65%; mp=255–259° C.; $^1$H NMR ($d_6$-DMSO) δ 8.24 (t, 1H), 7.57 (d, 1H), 7.27 (d, 1H), 6.78 (t, 1H), 4.50 (m, 2H), 3.24 (m, 2H). Anal Calcd for $C_{10}H_9N_3O_2$ (2 $H_2O$): C, 50.21; H, 5.48; N, 17.56. Found: C, 50.27; H, 5.60; N, 19.22.

R=4-carboxyphenyl (5k). Yield=32%; mp=300–320 (dec)° C.; $^1$H NMR ($d_6$-DMSO) δ 13.5 (bs, 1H), 8.66 (t, 1H), 8.23 (d, 2H), 8.10 (d, 2H), 8.06 (m, 2H), 7.57 (t, 1H), 4.58 (m, 2H), 3.64 (m, 2H). Anal Calcd for $C_{10}H_9N_3O_2$ (1.5 $H_2O$): C, 60.75; H, 4.71; N, 12.33. Found: C, 60.05; H, 4.86; N, 12.50.

R=3-N-methylindole (5l). Yield=64%; mp=270–275° C.; $^1$H NMR ($d_6$-DMSO) δ 8.52 (t, 1H), 8.43 (d, 1H), 8.14 (s, 1H), 7.94 (d, 1H), 7.86 (d, 1H), 7.65 (d, 1H), 7.38 (m, 2H), 7.31 (t, 1H), 4.62 (m, 2H), 4.00 (s, 3H), 3.65 (m, 2H). Anal Calcd for $C_{19}H_{16}N_4O$: C, 67.07; H, 5.63; N, 17.38. Found: C, 67.65; H, 5.64; N, 17.39.

R=3-methyl-3-phenylethyl (5m). Yield=35%; mp=163–167° C.; $^1$H NMR ($CDCl_3$) δ 8.04 (d, 1H), 7.93 (d, 1H), 7.36 (t, 1H), 7.23 (m, 4H), 7.11 (d, 1H), 6.91 (s, 1H), 3.90 (m, 1H), 3.60 (m, 1H), 3.42 (m, 1H), 3.01 (m, 1H)1.75 (m, 2H), 1.48 (d, 3H). Anal Calcd for $C_{19}H_{19}N_3O$ (0.5 EtOAc): C, 72.18; H, 6.63; N, 12.03. Found: C, 71.73; H, 6.84; N, 12.15.

R=trans-cyclopropylcarboxyethyl (5n). Yield=65%; mp=274–277° C.; $^1$H NMR ($d_6$-DMSO) δ 8.37 (t, 1H), 7.80 (d, 1H), 7.73 (d, 1H), 7.26 (t, 1H), 4.42 (m, 2H), 4.13 (q, 2H), 3.60 (m, 2H), 2.70 (m, 1H), 2.30 (m, 1H), 1.58 (m, 2H), 1.22 (t, 3H). Anal Calcd for $C_{16}H_{17}N_3O_3$ (0.25 $H_2O$): C, 63.25; H, 5.81; N, 13.83. Found: C, 63.52; H, 5.78; N, 13.61.

R=N,N-dimethylaminopropoxyphenol (5o). Yield=46%; mp=105–108° C.; $^1$H NMR ($CDCl_3$) δ 8.09 (d, 1H), 8.00 (d, 1H), 7.70 (d, 2H), 7.41 (t, 1H), 7.06 (d, 2H), 6.95 (t, 1H), 4.50 (m, 2H), 4.11 (t, 2H), 3.73 (m, 2H), 2.52 (t, 2H), 2.30 (s, 6H), 2.02 (m, 2H). Anal Calcd for $C_{21}H_{24}N_4O_2$ (1.5 $H_2O$): C, 64.43; H, 6.95; N, 14.31. Found: C, 64.74; H, 6.91; N, 14.07.

R=methoxymethyl (5p). mp=300–320° C.; $^1$H NMR ($d_6$-DMSO) δ 8.39 (t, 1H), 7.83 9d, 1H), 7.77 (d, 1H), 7.28 (t, 1H), 4.31 (m, 2H), 3.38 (s, 2H), 2.56 (s, 3H). Anal Calcd for $C_{12}H_{13}N_3O_2$: C, 63.19; H, 5.67; N, 18.19. Found: C, 62.33; H, 5.44; N, 18.86.

R=4-methoxycinnamoyl (5q). Yield=48%; mp=225–228° C.; $^1$H NMR ($d_6$-DMSO) δ 8.36 (t, 1H), 7.84 (m, 2H), 7.41–7.20 (m, 5H), 7.01 (d, 1H), 6.88 (t, 1H), 4.25 (m, 2H), 3.81 (s, 3H), 3.54 (m, 2H). Anal Calcd for $C_{19}H_{17}N_3O_2$ (0.5 $H_2O$): C, 69.12; H, 5.56; N, 12.62. Found: C, 70.00; H, 5.87; N, 12.73.

R=3-pyridyl (5r). Yield=54%; mp=276–279° C.; $^1$H NMR ($d_6$-DMSO) δ 9.06 (s, 1H), 8.77 (d, 1H), 8.49 (t, 1H), 8.29 (d, 1H), 7.95 (d, 1H), 7.91 (d, 1H), 7.64 (t, 1H), 7.39 (t, 1H), 4.49 (m, 2H), 3.56 (m, 2H). Anal Calcd for $C_{15}H_{12}N_4O$ (0.25 $H_2O$): C, 67.03; H, 4.69; N, 20.84. Found: C, 67.07; H, 4.70; N, 20.71.

R=o-Fluorophenyl (5s). Yield=51%. Mp=237–244° C.; $^1$H NMR ($d_6$-DMSO) δ 8.16 (m, 1H), 8.04 (m, 1H), 7.79 (t, 1H), 7.58 (m, 1H), 7.45 (t, 1H), 7.37 (t, 1H), 7.26 (t, 1H), 7.18 (t, 1H), 4.37 (m, 2H), 3.75 (m, 2H). Anal Calcd for $C_{16}H_{12}FN_3O$ (0.25 $H_2O$): C, 67.24; H, 4.41; N, 14.70. Found: C, 67.52; H, 4.46; N, 14.45.

R=2-quinolinyl (5t). Yield=66%. Mp=291–295° C.; $^1$H NMR ($d_6$-DMSO) δ 8.58 (d, 1H), 8.51 (t, 1H), 8.47 (d, 1H), 8.19 (d, 1H), 8.09 (d, 1H), 8.01 (d, 1H), 7.98 (d, 1H), 7.87 (t, 1H), 7.71 (t, 1H), 7.43 (t, 1H), 4.50 (m, 2H), 3.68 (m, 2H). Anal Calcd for $C_{19}H_{14}N_4O$: C, 72.60; H, 4.49; N, 17.82. Found: C, 72.47; H, 4.61; N, 17.70.

R=2-methyl-3-(4-methoxy)phenethyl (5u). Yield=78%. Mp=148–152° C.; $^1$H NMR ($CDCl_3$) δ 8.05 (d, 1H), 7.98 (d, 1H), 7.37 (t, 1H), 7.14 (t, 1H), 6.89 (d, 1H), 6.71 (d, 1H), 4.03 (m, 1H), 3.73 (s, 3H), 3.47 (m, 2H), 3.21 (m, 1H), 3.06 (m, 2H), 1.55 (d, 3H). Anal Calcd for $C_{20}H_{21}N_3O_2$ (0.2 $H_2O$): C, 70.86; H, 6.36; N, 12.39. Found: C, 70.84; H, 6.30; N, 12.57.

R=2-furyl (5v). Yield=75%. Mp=271–275° C.; $^1$H NMR ($d_6$-DMSO) δ 8.46 (t, 1H), 8.02 (s, 1H), 7.86 (d, 2H), 7.36 (t, 1H), 7.25 (d, 1H), 6.79 (d, 1H), 4.60 (m, 2H), 3.61 (m, 2H). Anal Calcd for $C_{14}H_{11}N_3O_2$ (0.6 $H_2O$): C, 63.68; H, 4.66; N, 15.91; Found: C, 63.76; H, 4.54; N, 15.93.

R=Benzyloxy (5w). Yield=85%. Mp=215–220° C.; $^1$H NMR ($d_6$-DMSO) δ 7.93 (m, 2H), 7.39 (m, 6H), 4.48 (s, 2H), 4.44 (m, 2H), 3.65 (m, 2H). Anal Calcd for $C_{18}H_{17}N_3O_2$ (1 $H_2O$) C, 66.45; H, 5.89; N, 12.91. Found: C, 66.70; H, 5.90; N, 12.81.

R=Phenylpropargyl (5x). Yield=75%. Mp=261–263° C.; $^1$H NMR ($d_6$-DMSO) δ 8.46 (t, 1H), 7.96 (d, 1H), 7.90 (d, 1H), 7.76 (d, 2H), 7.55 (m, 3H), 7.41 (t, 1H), 4.56 (m, 2H), 3.68 (m, 2H), Anal Calcd for $C_{18}H_{13}N_3O$ (0.3 $H_2O$) C, 73.86; H, 4.68 N, 14.35. Found: C, 73.92; H, 4.67; N, 14.27.

R=2-nitrofuryl (5y). Yield=65%. Mp=315–319° C.; $^1$H NMR ($d_6$-DMSO) δ 8.53 (t, 1H0, 7.96 (m, 3H), 7.57 (d, 1H), 7.45 (t, 1H), 4.69 (m, 2H), 3.65 (m, 2H). Anal Calcd for $C_{14}H_{10}N_4O_4$ (0.45 $H_2O$) C, 54.89; H, 3.59; N, 18.29. Found: C, 54.88; H, 3.49; N, 18.24.

R=2-methylacetoxyfuryl (5z). Yield=67%. Mp=261–263° C.; $^1$H NMR ($d_6$-DMSO) δ 8.48 (t, 1H), 7.88 (d, 2H), 7.38 (t, 1H), 7.23 (d, 1H), 6.84 (d, 1H), 5.18 (s, 2H), 4.59 (m, 2H), 3.61 (m, 2H), 2.09 (s, 3H). Anal Calcd for $C_{17}H_{15}N_3O_4$ (0.35 $H_2O$) C, 61.57; H, 4.77; N, 12.67. Found: C, 61.58; H, 4.58; N, 12.66.

R=cinammoyl (5aa). Yield=72%. Mp=300–305° C.; $^1$H NMR ($d_6$-DMSO) δ 8.40 (t, 1H), 7.85 (m, 5H), 7.35 (m, 5H), 4.58 (m, 2H), 3.64 (m, 2H). Anal Calcd for $C_{18}H_{15}N_3O$ (0.1 $H_2O$) C, 74.26; H, 5.26; N, 14.43. Found: C, 74.17; H, 5.36; N, 14.38.

R=β-phenylcinnamoyl (5bb). Yield=79%. Mp=210–215° C.; $^1$H NMR ($d_6$-DMSO) δ 8.34 (t, 1H), 7.86 (d, 1H), 7.78 (d, 1H), 7.38 (m, 4H), 714 (d, 2H), 7.10 (s, 1H), 4.20 (m, 2H), 3.40 (m, 2H). Anal Calcd for $C_{24}H_{19}N_3O$ C, 78.88; H, 5.24; N, 11.50. Found: C, 78.54; H, 5.25; N, 11.45.

R=3-Bromophenyl (5cc). Yield=57%. Mp=265–270° C.; $^1$H NMR ($d_6$-DMSO) δ 8.55 (t, 1H), 8.13 (s, 1H), 7.96 (m, 3H), 7.84 (d, 1H), 7.63 (t, 1H), 7.46 (t, 1H), 4.54 (m, 2H), 3.52 (m, 2H). Anal Calcd for $C_{16}H_{12}BrN_3O$ (0.5 $H_2O$) C, 54.72; H, 3.73; N, 11.96. Found: C, 55.36; H, 3.77; N, 11.83.

R=2-(p-chlorophenyl)furyl (5dd). Yield=64%. Mp=342–344° C.; $^1$H NMR ($d_6$-DMSO) δ 8.52 (t, 1H), 7.93 (m, 4H), 7.57 (d, 2H), 7.37 (m, 3H), 4.73 (m, 2H), 3.66 (m, 2H). Anal Calcd for $C_{20}H_{14}ClN_3O_2$ C, 66.03; H, 3.88; N, 11.55. Found: C, 65.73; H, 4.05; N, 11.44.

R=2(-m-chlorophenyl)furyl (5ee). Yield=63%. Mp=253–256° C.; $^1$H NMR ($d_6$-DMSO) δ 8.52 (t, 1H), 7.96 (s, 1H), 7.89 (m, 3H), 7.54 (t, 1H), 7.46 (m, 4H), 4.71 (m, 2H), 3.66 (m, 2H). Anal Calcd for $C_{20}H_{14}ClN_3O_2$ (0.1 $H_2O$) C, 65.70; H, 3.91; N, 11.49. Found: C, 65.61; H, 3.96; N, 11.33.

R=2-(o-chlorophenyl)furyl (5ff). Yield=70%. Mp=264–267° C.; $^1$H NMR ($d_6$-DMSO) δ 8.51 (t, 1H), 8.04 (d, 1H), 7.91 (t, 2H), 7.64 (d, 1H), 7.54 (t, 1H), 7.40 (m, 4H), 4.75 (m, 2H), 3.67 (m, 2H). Anal Calcd for $C_{20}H_{14}ClN_3O_2$ (0.2 $H_2O$) C, 65.38; H, 3.95; N, 11.44. Found: C, 65.20; H, 3.91; N, 11.45.

R=2-bromothiophenyl (5gg). Yield=53%. Mp=260–263° C.; $^1$H NMR ($d_6$-DMSO) δ 8.49 (t, 1H), 7.87 (m, 2H), 7.56 (d, 1H), 7.44 (d, 1H), 7.37 (t, 1H), 4.57 (m, 2H), 3.61 (m, 2H). Anal Calcd for $C_{14}H_{10}BrSN_3O$ C, 48.29; H, 2.89; N, 12.07. Found: C, 48.00; H, 2.99; N, 11.88.

R=$CH_2CH_2COOH$ (5hh). Yield=45%. Mp=298–304° C.; $^1$H NMR ($d_6$-DMSO) δ 12.28 (s, 1H), 8.36 (t, 1H), 7.80 (m, 2H), 7.26 (t, 1H), 4.32 (m, 2H), 3.57 (m, 2H), 3.07 (t, 2H), 2.83 (t, 2H). Anal Calcd for $C_{13}H_{13}N_3O_3$ C, 60.23; H, 5.05; N, 16.21. Found: C, 60.39; H, 5.21; N, 15.98.

R=3-carboxyphenyl (5ii). Yield=82%. Mp=300–320° C.; $^1$H NMR ($d_6$-DMSO) δ 13.28 (s, 1H), 8.48 (t, 1H), 8.41 (s, 1H), 8.11 (m, 2H), 7.90 (m, 2H), 7.72 (t, 1H), 7.37 (t, 1H), 4.47 (m, 2H), 3.54 (m, 2H), 3.54 (m, 2H). Anal Calcd for $C_{17}H_{13}N_3O_3$ (0.25 $H_2O$) C, 65.48; H, 4.36; N, 13.48. Found: C, 65.46; H, 4.51; N, 13.43.

R=p-carboxyethyldihydrocinnamoyl (5jj). Yield=82%; mp=230–233° C.; $^1$H NMR (DMSO-$d_6$) δ 8.34 (bt, 1H), 7.89 (d, 2H), 7.80 (m, 2H), 7.46 (d, 2H), 7.27 (t, 1H), 4.50 (m, 2H), 4.30 (q, 2H), 3.53 (m, 2H), 3.21 (m, 4H), 1.31 (t, 3H). MS (ES+=364.23). Anal Calcd. for $C_{21}H_{21}N_3O_3$ (0.25 $H_2O$): C, 68.56; H, 5.89; N, 11.42. Found: C, 68.30; H, 5.84; N, 11.52.

R=1-(t-butoxycarbonyl)amino-2-phenyl ethane (5kk). Yield=27%; mp=175–179° C.; $^1$H NMR (DMSO-$d_6$) δ 8.35 (bt, 1H), 7.85 (m, 2H), 7.58 (d, 1H), 7.31 (t, 1H), 7.23 (m, 5H), 5.09 (m, 1H), 4.14 (m, 2H), 3.45 (m, 2H), 1.29 (s, 9H). Anal Calcd. for $C_{23}H_{26}N_4O_3$ (0.5 $H_2O$): C, 66.49; H, 6.55; N, 13.48. Found: C, 66.33; H, 6.45; N, 13.55.

R=1-amino-2-phenyl ethane (5ll). This compound was made by deprotection of 5kk (500 mg, 2.82 mmol) with 10% TFA/DCM (5 mL). After stirring for 16h, the solvent was removed and the residue was triturated with HCl/diethyl ether (1.0M, 5 mL) and filtered. The crystals were washed several times with diethyl ether and dried to yield 405 mg (47%). Mp=155–160° C. (dec.); $^1$H NMR DMSO-$d_6$) δ 7.93 (d, 1H), 7.85 (d, 1H), 7.40 (t, 2H), 7.13 (m, 3H), 6.89 (d, 1H), 5.01 (m, 1H), 4.15 (m, 2H), 3.48 (m, 2H), 3.21 (t, 2H). Anal Calcd. for $C_{18}H_{18}N_4O$ HCl (2 $H_2O$): C, 51.64; H, 5.86; N, 13.02. Found: C, 52.09; H, 5.74; N, 12.94.

R=4-carboxymethylphenyl (5mm). Yield=85%; mp=260–265° C.; $^1$H NMR (DMSO-$d_6$) δ 8.51 (bt, 1H), 8.14 (d, 2H), 8.04 (d, 2H), 7.93 (m, 2H), 7.40 (t, 1H), 4.50 (m, 2H), 3.92 (s, 3H), 3.56 (m, 2H). MS (ES+=322.19). ° C. Anal Calcd. for $C_{23}H_{26}N_4O_3$(1.5 $H_2O$): C, 62.06; H, 5.21; N, 12.06. Found: C, 61.75; H, 5.08; N, 12.19.

R=4-hydroxymethylphenyl (5nn). This compound was made from ester 5 mm in a similar manner to alcohol 9. Yield=84%; mp=243–248° C.; $^1$H NMR (DMSO-$d_6$) δ 8.47 (t, 1H), 7.85 (m, 4H), 7.53 (d, 2H), 7.36 (t, 1H), 5.38 (t, 1H), 4.61 (m, 2H), 4.46 (m, 2H), 3.54 (m, 2H). Anal Calcd. for $C_{17}H_{15}N_3O_2$ (0.4 $H_2O$): C, 67.94; H, 5.30; N, 13.98. Found: C, 68.30; H, 5.27; N, 13.90.

R=4-chloromethylphenyl (5oo). This compound was made from alcohol 5nn in a similar manner to benzyl chloride 10. Yield=78%; $^1$H NMR (DMSO-$d_6$) δ 8.84 (t, 1H), 8.16 (m, 2H), 8.03 (d, 2H), 7.76 (m, 3H), 4.95 (s, 2H), 4.58 (m, 2H), 3.65 (m, 2H). MS (ES+=300.03).

R=2-N-methyl pyrrole (5pp). Yield=56%; mp=244–248° C.; $^1$H NMR (DMSO-$d_6$) δ 8.45 (t, 1H), 7.87 (d, 1H), 7.84 (d, 1H), 7.33 (t, 1H), 7.10 (dd, 1H), 6.67 (dd, 1H), 6.24 (dd, 1H), 4.46 (m, 2H), 3.94 (s, 3H). Anal Calcd. for $C_{15}H_{14}N_4O$: C, 67.65; H, 5.30; N, 21.04. Found: C, 67.59; H, 5.36; N, 21.14.

R=2-pyrrole (5qq). Yield=48%; mp=323–330° C.; $^1$H NMR (DMSO-$d_6$) δ 11.93 (s, 1H), 8.45 (t, 1H), 7.79 (t, 2H), 7.31 (t, 1H), 7.04 (s, 1H), 6.77 (s, 1H), 6.29 (m, 1H), 4.53 (m, 2H) 3.59 (m, 2H); MS (ES+=253.21). Anal. Calcd. for $C_{14}H_{12}N_4O$ (0.4 $H_2O$): C, 64.80; H, 4.97; N, 21.59. Found: C, 64.78; H, 4.82; N, 21.75.

R=2-imidazole (5rr). Yield=61%; mp=334–348° C.; $^1$H NMR (DMSO-$d_6$) δ 13.37 (s, 1H), 8.47 (t, 1H), 7.91 (t, 2H), 7.39 (m, 2H), 7.23 (s, 1H), 4.50 (m, 2H), 3.65 (m, 2H); MS (ES−=252.01). Anal Calcd. for $C_{13}H_{11}N_5O$ (0.15 $H_2O$): C, 61.00; H, 4.45; N, 27.36. Found: C, 60.95; H, 4.42; N, 27.44.

R=2-N-methylimidazole (5ss). Yield=78%; mp=206–210° C.; $^1$H NMR (DMSO-$d_6$) δ 8.46 (t, 1H), 7.95 (dd, 2H), 7.51 (s, 1H), 7.39 (t, 1H), 7.20 (s, 1H), 4.50 (m, 2H), 4.09 (s, 3H), 3.60 (m, 2H); MS (ES+=268.31). Anal Calcd. for $C_{14}H_{13}N_5O$: C, 62.91; H, 4.90; N, 26.20. Found: C, 62.79; H, 5.06; N, 25.91.

R=2-(5-nitrophenyl)furyl (5tt). Yield=86%; mp=290–296° C.; $^1$H NMR (DMSO-$d_6$) δ 8.62 (s, 1H), 8.52 (t, 1H), 8.33 (d, 1H), 8.21 (d, 1H), 7.93 (d, 1H), 7.90 (d, 1H), 7.80 (t, 1H), 7.61 (d, 1H), 7.45 (d, 1H), 7.39 (t, 1H), 4.73 (m, 2H), 3.66 (m, 2H); MS (ES+=375.23). Anal Calcd. for $C_{20}H_{14}N_4O_4$: C, 63.56; H, 3.84; N, 14.82. Found: C, 63.63; H, 3.80; N, 14.88.

R=2-(4,5-dimethyl)furyl (5uu). Yield=50%; mp=305–310° C.; $^1$H NMR (DMSO-$d_6$) δ 8.44 (t, 1H), 7.83 (d, 2H), 7.33 (t, 1H), 7.05 (s, 1H), 4.56 (m, 2H), 3.61 9d, 2H), 2.34 (s, 3H), 2.03 (s, 3H); MS (ES+=282.32). Anal Calcd. for $C_{16}H_{15}N_3O_2$ (0.2 $H_2O$): C, 64.45; H, 5.45; N, 14.75. Found: C, 67.50; H, 5.40; N, 14.90.

R=2-(5-carboxy)furyl (5vv). Yield=93%; mp=301–302° C.; $^1$H NMR (DMSO-$d_6$) δ 8.49 (t, 1H), 7.94 (d, 2H), 7.43 (m, 3H), 4.66 (m, 2H), 3.63 (m, 2H),. Anal Calcd. for $C_{15}H_{11}N_3O_4$ (1 $H_2O$): C, 57.14; H, 4.16; N, 13.33. Found: C, 57.08; H, 4.19; N, 13.31.

R=2-(5-N-methylpiperazinamido)furyl (5ww). This compound was made by coupling N-methylpiperazine with 5vv using EDC/DMAP as outlined in examples 7a–n. Yield=16%. Mp=261–265° C. $^1$H NMR (DMSO-$d_6$) δ 8.48,(t, 1H), 7.93 (d, 1H), 7.90 (d, 1H), 7.39 (t, 1H), 7.35 (d, 1H), 7.26 (d, 1H), 4.64 (m, 2H), 3.65 (m, 6H), 2.39 (t, 4H), 2.22 (s, 3H). MS (ES+=282.32). Anal Calcd. for $C_{20}H_{21}N_5O_3$ (0.6 $H_2O$): C, 61.56; H, 5.73; N, 17.95. Found: C, 61.52; H, 5.67; N, 18.01.

R=3-(5-nitro)thiophene (5xx). MS (ES+=315.21).

R=2-thiophene (5yy). MS (ES+=270.31).

R=2-(N-methyl)-5-formylpyrrole (5zz). This compound was prepared from the formylation of pyrrole 5pp (see J. Med. Chem. 1989, 32, 896). The isomers were separated by column chromatography (DCM→2%MeOH/DCM). Yield of 5zz=10%. Mp=241–247° C.; $^1$H NMR (DMSO-$d_6$) δ 9.73 (s, 1H), 8.50 (t, 1H), 7.97 (d, 1H), 7.94 (d, 1H), 7.41 (t, 1H), 7.23 (d, 1H), 6.87 (d, 1H), 4.46 (t, 2H), 4.15 (s, 3H), 3.58 (t, 2H). Anal Calcd. for $C_{16}H_{14}N_4O_2$ (0.3 $H_2O$): C, 64.12; H, 4.91; N, 18.69. Found: C, 64.29; H, 4.91; N, 18.65.

R=2-(N-methyl)-4-formylpyrrole (5aaa). Yield=5%; mp=228–230° C.; $^1$H NMR (DMSO-$d_6$) δ 9.76 (s, 1H), 8.48 (t, 1H), 8.00 (s, 1H), 7.90 (t, 2H), 7.37 (t, 1H), 7.12 (s, 1H) 4.49 (s, 2H), 3.99 (s, 3H), 3.57 (t, 2H). Anal Calcd. for $C_{16}H_{14}N_4O_2$: C, 65.30; H, 4.79; N, 19.04. Found: C, 65.32; H, 4.93; N, 19.01.

R=2-(5-amino)furyl (5bbb). This amine was made by the reduction of nitrofuryl 5y with Pd/C/$H_2$. MS (ES+=269.21).

R=$CH_2CH_2C(O)NCH_2CH_2$(m-$MeOC_6H_4$) (5ccc). Compounds 5ccc and 5ddd were made by standard EDC coupling conditions as stated previously for examples 7a–n. Yield=43%; mp=165–167° C.; $^1$H NMR (DMSO-$d_6$) δ 8.36 (s, 1H), 8.07 (s, 1H), 7.81 (d, 1H0, 7.75 (d, 1H), 7.26 (t, 1H), 7.15 (t, 1H), 6.76 (m, 3H), 4.31 (m, 2H), 3.72 (s, 3H), 3.58 (s, 2H), 3.27 (d, 2H), 3.06 (s, 2H), 2.67 (s, 4H). Anal Calcd. for $C_{22}H_{24}N_4O_3$ (0.5 $H_2O$): C, 65.82; H, 6.28 N, 13.96. Found: C, 65.80; H, 6.08; N, 13.95.

R=$CH_2CH_2C(O)NHCH_2CH_2$-piperazine (5ddd). Yield=16%; $^1$H NMR (DMSO-$d_6$) δ 8.35 (t, 1H), 7.87 (t, 1H), 7.80 (d, 1H), 7.74 (d, 1H), 7.25 (t, 1H), 4.32 (m, 2H), 3.56 (s, 2H), 3.12 (m, 4H), 2.67 (t, 2H), 2.25 (m, 6H), 1.42 (m, 6H). Anal Calcd. for $C_{20}H_{27}N_5O_2$: C, 65.02; H, 7.37; N, 18.96. Found: C, 65.00; H, 7.24; N, 19.10.

Scheme 3-4
Synthesis of imidazobenzodiazepine amines 6a-dd

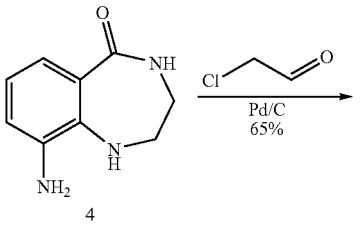

-continued

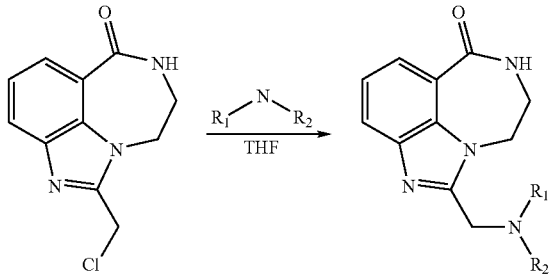

Synthesis of chloride 5n. Amine 4 (200 mg, 1.13 mmol), palladium on carbon (50 mg), were suspended in $CH_3CN$ (10 mL). A 50% solution of chloroacetaldehyde in water (215 μL, 1.31 mmol) was added to this mixture and the reaction was stirred for 3 h. The reaction mixture was coarse frit and concentrated. The crude filtrate was analyzed to be 95% 5n and was used in the amination step without further purification. Yield=69%, 173 mg; $^1$H NMR ($d_6$-DMSO) δ 8.43 (t, 1H), 7.92 (d, 1H), 7.87 (d, 1H), 7.35 (t, 1H), 5.08 (s, 2H), 4.41 (m, 2H), 3.63 (m, 2H).

General Procedure for amination of chloride 5n (6a, R=piperazine). The chloride 5n (150 mg, 0.64 mmol) was suspended in $CH_3CN$ (5 mL) and piperidine (108 mg, 1.3 mmol) was added followed by refluxing for 12 h. The solution was quenched with water (1 mL) followed by extraction with EtOAc (2×5 mL). The combined organics were dried with anhydrous sodium sulfate and the resulting residue was triturated with either diethyl ether or hexanes and dried to yield the crude products 6a–dd. The resulting solid (96 mg, 53%) was the desired amine 6a. $^1$H NMR ($d_6$-DMSO) δ 8.35 (t, 1H), 7.82 (d, 1H), 7.76 (d, 1H), 7.27 (t, 1H), 4.31 (m, 2H), 3.61 (m, 2H), 3.35 (s, 2H), 3.03 (s, 2H), 2.55 (s, 2H), 1.68 (m, 4H), 1.59 (m, 2H). MS(ES+=285.07).

Scheme 3-4a
Alternative Synthesis of imidazobenzodiazepine amines 6a-kk

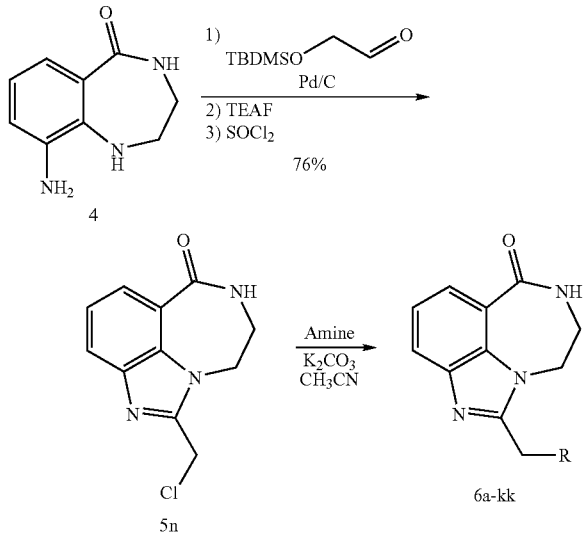

Alternative Synthesis of chloride 5n. The amine 4 (12.5 g, 70.6 mmol), palladium on carbon (500 mg) and t-butyldimethylsilyloxyacetaldehyde (15.0 g, 84.7 mmol) were suspended in 500 mL THF and refluxed overnight. The reaction was monitored by TLC (EtOAc) and after consumption of the amine (16 h), the palladium was filtered off and the filtrate was treated with tetrabutylammonium fluoride (75 mL, 1.0 M in THF). The solvent was removed and the resulting residue was triturated with 75 mL diethyl ether and 75 mL MeOH and filtered. The solid was dried and characterized as the intermediate alcohol (13.6 g, 89%, >95% purity). This compound was chlorinated without further purification. The alcohol was added portionwise to thionyl chloride (25 mL) and stirred overnight. The thionyl chloride was then removed in vacuo and the residue was triturated several times with diethyl ether. The crude solid was recrystallized from acetonitrile (12.2 g, 74% overall yield). $^1$H NMR (DMSO-$d_6$) δ 8.44 (t, 1H), 7.92 (d, 1H), 7.87 (d, 1H), 7.36 (t, 1H), 5.08 (s, 2H), 4.42 (m, 2H), 3.63 (m, 2H); MS (ES+=392.34). Anal Calcd. for $C_{11}H_{10}ClN_3O$: C, 56.06; H, 4.28; N, 17.83. Found: C, 56.06; H, 4.27; N, 17.83. The amines 6ee–kk were made from this compound.

6b, R=N-benzylmethylamine. $^1$H NMR ($d_6$-DMSO) δ 8.44 (t, 1H), 7.89 (m, 2H), 7.35 (m, 6H), 4.45 (m, 2H), 3.90 (s, 2H), 3.65 (m, 2H), 3.62 (s, 2H), 2.17 (s, 3H). MS (ES+=321.012).

6c, R=imidazole. MS (ES+=267.93).

6d, R=pyrrolidine. MS (ES+=270.97).

6e, R=tetrahydroquinoline. MS (ES+=322.98).

6f, R=N-methylaniline. MS (ES+=306.98).

6g, R=N-methylpiperazine. MS (ES+=300.02).

6h, R=N,N,N-trimethylethylenediamine. MS (ES+=302.03).

6i, R=N-methylcyclohexylamine. MS (ES+=313.04).

6j, R=N-Phenylpiperazine. MS (ES+=361.97).

6k, R=N,N-dibutylamine. MS (ES+=329.04).

6l, R=N,N,N-trimethylpropanediamine. MS (ES+=316.03).

6m, R=4-piperidone. MS (ES+=298.97).

6n, R=3-methylcarboxy-4-piperidone. MS (ES+=356.96).

6o, R=2-piperidine-methanol. MS (ES+=315.03).

6p, R=hexamethyleneimine. MS (ES+=299.05).

6q, R=morpholine. MS (ES+=287.02).

6r, R=N-benzylpiperazine. MS (ES+=377.05).

6s, R=heptamethyleneimine. MS (ES+=313.08).

6t, R=N,N-dipentylamine. MS (ES+=357.14).

6u, R=N,N-dihexylamine. MS (ES+=385.17).

6v, R=N,N-diisopropylamine. MS (ES+=301.10).

6w, R=N,N-diethylamine. MS (ES+=273.10).

6x, R=N-methyl-p-anisidine. MS (ES+=337.06).

6y, R=N-benzyl-[2.2.1]-diazabicycloheptane. MS (ES+=388.10).

6z, R=N,N-dipropylamine. MS (ES+=301.10).

6aa, R=N,N-dimethylamine. MS (ES+=245.02).

6bb, R=N,N-dibenzylamine. MS (ES+=397.09).

6cc, R=N-tertbutoxycarbonyl piperazine. MS (ES+=386.11).

6dd, R=piperonyl piperazine. MS (ES+=420.09).

R=N-benzyl-(N,N-dimethylaminoethyl)amine (6ee). $^1$H NMR ($CDCl_3$) δ 8.57 (bt, 1H), 8.05 (t, 2H), 7.50 (t, 1H), 7.39 (m, 5H), 5.12 (s, 2H), 4.50 (bs, 2H), 3.80 (bs, 2H), 3.60 (m, 4H), 3.36 (s, 6H), 3.10 (m, 2H). MS (ES+=377.99).

R=N-benzyl-N-phenethylamine (6ff). MS (ES+=410.98).

R=tetrahydroisoquinoline (6gg). MS (ES+=332.98).

R=4,5-dimethoxytetrahydroisoquinoline (6hh). MS (ES+=392.96).

R=L-prolyine O-tButylester (6ii). MS (ES+=371.01).

R=[2.2.1]diazabicycloheptane (6jj). MS (ES+=298.30).

R=(N-3-fluorophenyl)[2.2.1]diazabicycloheptane (6kk). $^1$H NMR (DMSO-$d_6$) δ 8.38 (bt, 1H), 7.79 (m, 2H), 7.25 (t, 1H), 7.15 (m, 1H), 6.48 (m, 3H), 4.45 (s, 2H), 4.50 (m, 2H), 3.95 (m, 2H), 3.70 (m, 2H), 3.45 (m, 2H), 2.76 (dd, 2H), 1.87 (dd, 2H). MS (ES+=392.34). Anal Calcd. for $C_{22}H_{22}FN_5O$ (0.75 $H_2O$): C, 65.25; H, 5.85; N, 17.29. Found: C, 65.63; H, 5.77; N, 16.88.

Scheme 4-4
General Synthesis of amides 7a-n.

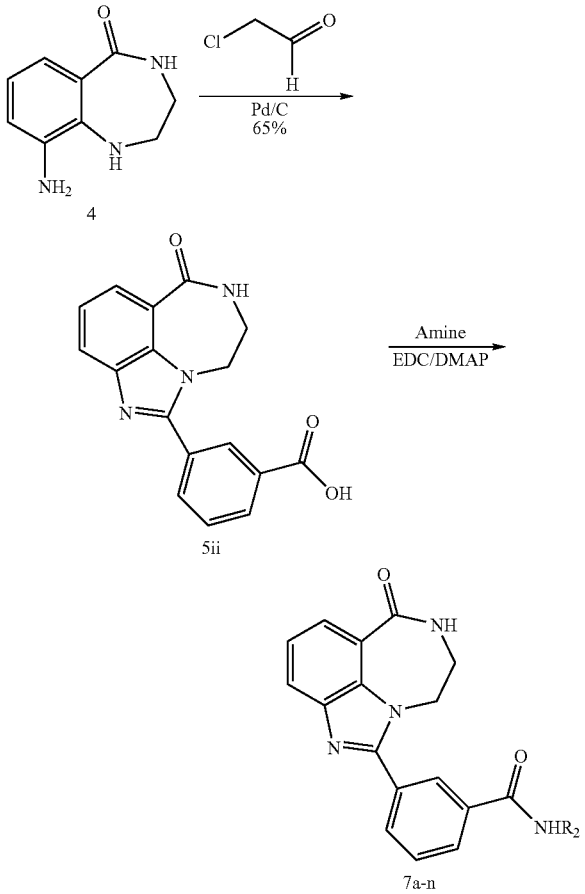

General procedure for the synthesis of amides 7a–n. Carboxylic acid (5ii) (80 mg, 0.26 mmol), EDC (94 mg, 0.52 mmol), DMAP (5 mg) and the requisite amine (0.52 mmol) were mixed together in a solution of DCM/NMP (10:1, 5 mL). The reaction were agitated overnight. Workup consisted of washing with water (3 mL) and drying the organic phase through a plug of sodium sulfate. The crude amides 7a–n were all isolated by concentrating the organic phase.

7a, N-(aminoethyl)-morpholine. MS (ES+=419.94).

7b, N-(aminoethyl)-pyrrolidine. MS (ES+=403.96).

7c, N-aminoethyl-piperidine. MS (ES+=417.98).

7d, N-methylpiperazine. MS (ES+=389.98).

7e, N-benzylpiperazine. MS (ES+=465.98).

7f, Piperonylpiperazine. MS (ES+=509.94).

7g, N-boc-piperazine. MS (ES+=475.98).

7h, N,N,N-trimethylpropanediamine. MS (ES+=406.02).

7i, 2-(aminoethyl)-N-methylpyrrolidine MS (ES+=418.01).

7j, N,N-diethylethylenediamine. MS (ES+=406.02).

7k, N,N-dimethylethylenediamine. MS (ES+=378.00).

7l, N,N-diethylpropanediamine. MS (ES+=420.04).

7m, N-benzyl-diaza[2.2.]bicycloheptane. MS (ES−=475.90).

7n, 3-carboxymethyl-4-piperidinone. MS (ES+=446.96).

Synthesis of Bicyclic Amines 8a–t.

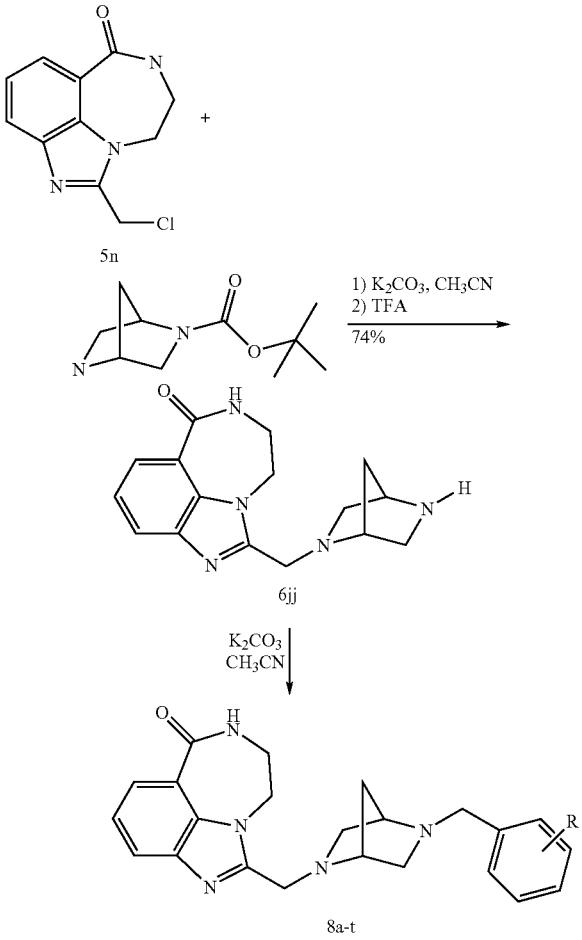

R=H (8a). $^1$H NMR (DMSO-$d_6$) δ 8.38 (bt, 1H), 7.85 (d, 1H), 7.80 (d, 1H), 7.32 (m, 6H), 4.50 (m, 2H), 4.00 (d, 1H), 3.92 (d, 1H), 3.70 (d, 1H), 3.65 (m, 3H), 3.25 (m, 2H), 2.81 (d, 1H), 2.59 (m, 3H), 1.67 (m, 2H). MS (ES+=377.99). Anal Calcd. for $C_{23}H_{25}N_5O$ (0.2 $H_2O$): C, 70.64; H, 6.40 N, 17.91. Found: C, 70.86; H, 6.55; N, 17.95.

R=2,5-dimethyl (8b). MS (ES+=416.35).

R=3-methoxy (8c). MS (ES+=418.33).

R=4-methoxy (8d). MS (ES+=418.33).

R=4-Oacetyl (8e). MS (ES+=446.33).

R=3,4-dimethyl (8f). MS (ES+=416.37).

R=3,4-dichloro (8g). MS (ES+=456.24).

R=4-t-butyl (8h). MS (ES+=444.41).

R=4-methyl (8i). MS (ES+=402.38).

R=4-fluoro (8j). MS (ES+=406.37).

R=3-chloro (8k). MS (ES+=422.65).

R=2-fluoro (8l). MS (ES+=406.30).

R=3-methyl (8m). MS (ES+=402.32).

R=2-methyl (8n). MS (ES+=402.35).

R=3-fluoro (8o). MS (ES+=406.33).

R=2-chloro (8p). MS (ES+=422.30).

R=4-trans-stilbene (8q). MS (ES+=489.62).

R=4-Obenzyl (8r). MS (ES+=494.36).

R=2-chloropiperonyl (8s). MS (ES+=466.30).

R=4-chloro (8t). MS (ES+=422.34).

Scheme 6-4
Synthesis of amines 11a-f.

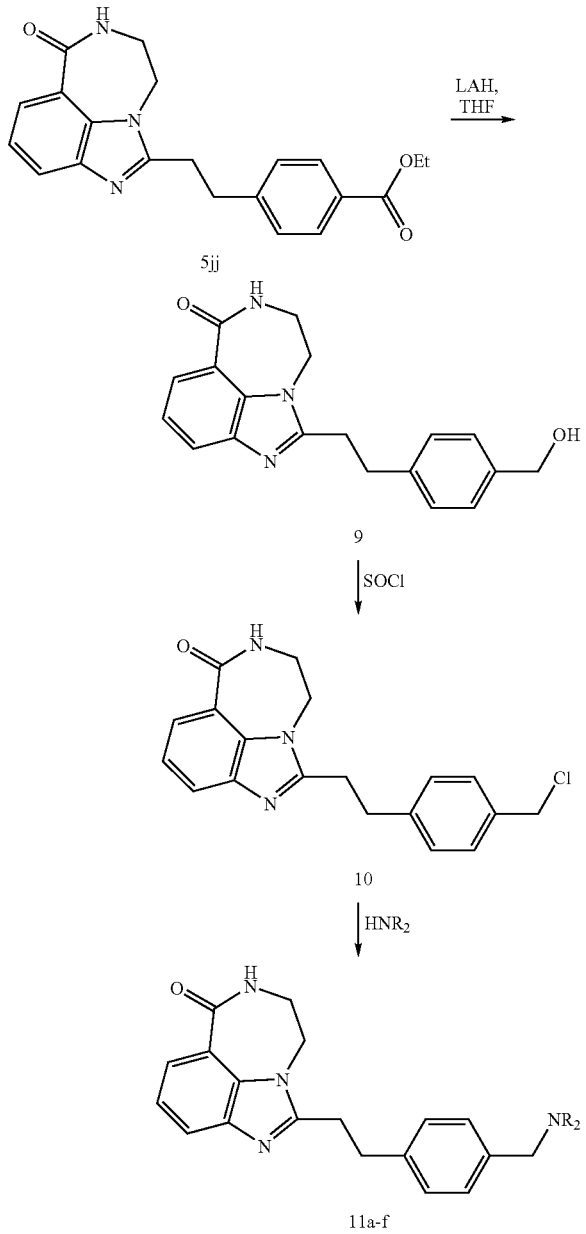

Alcohol 9. Ethyl ester 5jj (500 mg, 1.38 mmol) was suspended in THF (20 mL) and cooled to 0° C. Lithium aluminum hydride (100 mg, 2.74 mmol) was added portionwise over the next 30 min. The reaction mixture was stirred at room temperature overnight. The reaction was quenched with 10 mL EtOAc and washed with water (10 mL). The organic layer was partitioned and the aqueous layer was repeatedly extracted with EtOAc (4×10 mL). The combined organics were dried with $Na_2SO_4$ and concentrated in vacuo.

The resulting crude solid was triturated with diethyl ether (10 mL) and filtered. The resulting solid was characterized as the alcohol 9. Yield=400 mg (96%); $^1$H NMR (DMSO-$d_6$) δ 8.32 (bt, 1H), 7.78 (t, 2H), 7.25 (t, 1H), 7.22 (m, 4H), 5.11 (t, 1H), 4.45 (m, 2H), 4.44 (d, 2H), 3.49 (m, 2H), 3.12 (m, 2H), 3.08 (m, 2H); MS (ES+=322.40). Anal Calcd. for $C_{19}H_{19}N_5O_2$ (0.75 $H_2O$): C, 68.14; H, 6.08; N, 12.55. Found: C, 68.59; H, 6.08; N, 12.27.

Benzyl Chloride 10. The alcohol 9 (350 mg, 1.09 mmol) was added portionwise to a cooled (0° C.), stirred solution of thionyl chloride (3 mL). After 3 h of stirring, the thionyl chloride was removed in vacuo and the crude chloride was triturated with diethyl ether and filtered to yield 295 mg of the crude chloride (est. purity >95%). This material was aminated without further purification. $^1$H NMR (DMSO-$d_6$) δ 8.46 (bt, 1H), 7.88 (m, 2H), 7.35 (m, 4H), 4.74 (s, 2H), 4.30 (bs, 2H), 3.53 (bs, 2H), 3.27 (m, 2H), 3.17 (m, 2H); MS (ES+=340.30).

General procedure for amination of chloride 10. The chloride 10 (20 mg, 0.058 mmol) was dissolved in $CH_2CN$ (1 mL). Potassium carbonate was added to the mixture (16 mg, 0.12 mmol) followed by the requisite amine (0.12 mmol). The reactions were heated to 60° C. overnight. The reaction was then quenched with 1M HCl (1 mL) and extracted with EtOAc (2 mL). The aqueous layer was basified with $K_2CO_3$ and extracted with EtOAc (2×2 mL). The EtOAc was concentrated in vacuo and the crude amines were characterized by MS.

$NR_2$=Dimethylamine (11a). MS (ES+=349.35).

$NR_2$=Piperidine methanol (11b). MS (ES+=419.38).

$NR_2$=N-methylpiperazine (11c). MS (ES+=404.38).

$NR_2$=Tetrahydroisoquinoline (11d). MS (ES+=437.36).

$NR_2$=N,N,N-trimethylpropylenediamine (11e). MS (ES+=420.42).

$NR_2$=Pyrrolidine (11f). The HCl salt of 11f was prepared by suspending the free base in EtOAc and adding 1.1 eq HCl/$Et_2O$ and stirring for 1 h. Filtration of the resulting solid led to a hygroscopic solid. Yield=72%; $^1$H NMR ($CDCl_3$) δ 7.93 (d, 1H), 7.79 (d, 1H), 7.49 (t, 1H), 7.22 (d, 2H), 7.11 (d, 2H), 4.50 (m, 5H), 4.17 (s, 2H), 3.40 (m, 2H), 3.25 (m, 4H), 3.13 (m, 2H), 2.99 (m, 2H), 2.00 (m, 2H), 1.83 (m, 2H); MS (ES+=375.38). Anal Calcd. for $C_{23}H_{27}ClN_4O_1$ (4 $H_2O$): C, 57.19; H, 7.30; N, 11.60. Found: C, 56.93; H, 7.46; N, 11.74.

Scheme 7-4
Synthesis of amides 13a-k.

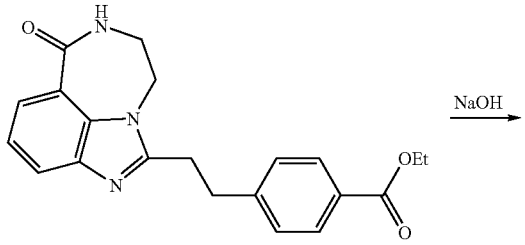

-continued

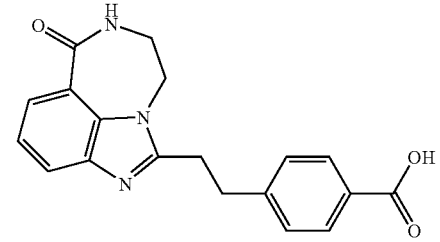

EDC, Diamines

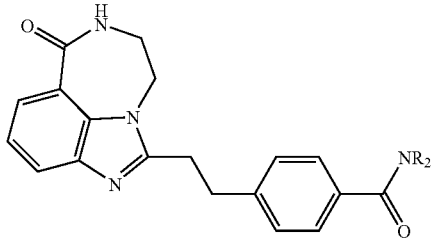

Carboxylic Acid 12. The ester 5jj (1.0 g, 2.75 mmol) was suspended in 1M NaOH and heated at 100° C. until dissolution occurred. The reaction mixture was cooled and acidified to pH 7 and the solid was filtered off. The solid was dried and characterized to be the desired material 12. Dry Yield=761 mg (82%); mp=300–320° C.; $^1$H NMR (DMSO-$d_6$) δ 12.86 (bs, 1M), 8.35 (bt, 1H), 7.87 (d, 2H), 7.81 (m, 2H), 7.43 (d, 2H), 7.28 (t, 1H), 4.27 (m, 2H), 3.53 (m, 2H), 3.21 (m, 4H). Anal Calcd. for $C_{19}H_{17}N_3O_3$ (3 $H_2O$): C, 58.76; H, 4.71; N, 10.82. Found: C, 58.74; H, 4.85; N, 10.81.

General procedure for the synthesis of amides 13a–k. The carboxylic acid 12 (20mg, 0.060 mmol) was suspended in DCM/NMP (1 mL, 4/1 mixture). The EDC (18 mg, 0.094 mmol), DMAP (catalytic amount) and requisite amine (1.2 eq) were added and the reactions were stirred overnight. The reaction was quenched with water (2 mL) and partitioned with DCM (2×2 mL). The combined organics were dried and concentrated to yield the crude amides. The amides were characterized by MS.

$NR_2$=N-benzyl-[2.2.1]diazabicycloheptane (13a). MS (ES+=506.26).

$NR_2$=N-benzyl piperazine (13b). MS (ES+=494.28).

$NR_2$=N-aminoethylpyrolidine (13c). MS (ES+=432.31).

$NR_2$=N-aminoethylpiperidine (13d). MS (ES+=446.31).

$NR_2$=4-carboxymethylpiperidine (13e). MS (ES+=461.29).

$NR_2$=N,N-diethylethylenediamine (13f). MS (ES+=434.33).

$NR_2$=N-methyl piperazine (13g). MS (ES+=418.31).

$NR_2$=3-carboxymethyl-4-oxopiperidine (13h). MS (ES+=475.27).

$NR_2$=N,N,N-trimethylethylenediamine (13i). MS (ES+=420.36).

$NR_2$=glycine t-butylester (13j). MS (ES+=447.29).

$NR_2$=glycine (13k). This compound was made by the deprotection of glycine t-butyl ester 13j (300 mg, 1.0 mmol) with 10% TFA in DCM. After stirring for 16 h, the solvent was removed and the residue taken up in 10% $Na_2CO_3$. Extraction of this basic mixture followed by acidification and reextraction with EtOAc (3×5 mL) led to a solution of the desired acid 13k. The EtOAc was removed in vacuo the crude solid was recrystallized from MeOH/EtOAc (75 mg, 20%). $^1$H NMR (DMSO-$d_6$) δ 12.75 (bs, 1H), 9.13 (bt, 1H), 8.51 (bt, 1H), 8.39 (s, 1H), 8.07 (m, 2H), 7.94 (m, 2H), 7.72 (t, 1H), 7.39 (t, 1H), 4.51 (m, 2H), 3.98 (m, 2H), 3.56 (m, 2H). Anal Calcd. for $C_{19}H_{16}N_4O_4$: C, 62.63; H, 4.43; N, 15.38. Found: C, 62.28; H, 4.49; N, 15.34.

Scheme 8-4
Synthesis of amides 14a-j.

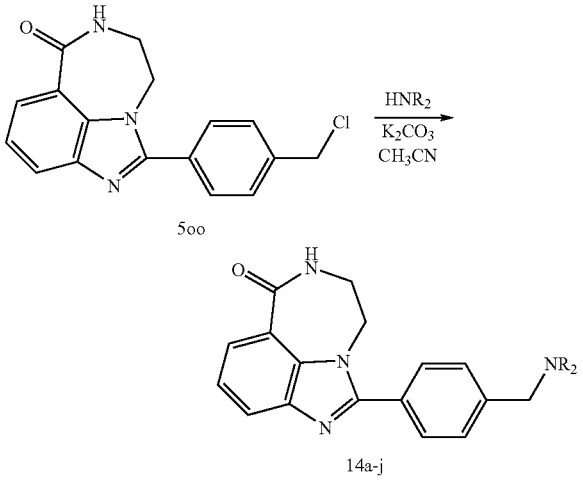

General procedure for the synthesis of amines 14a–j. The procedure followed to synthesize 14a–j was similar to the synthesis of amines 6a–kk.

$NR_2$=dimethylamine (14a). MS (ES+=321.26).

$NR_2$=pyrrolidine (14b). MS (ES+=347.27).

$NR_2$=4-carboxymethylpiperidine (14c). MS (ES+=419.26).

$NR_2$=N-methylglycine (14d). MS (ES+=367.21).

$NR_2$=tetrahydroisoquinoline (14e). MS (ES+=407.26).

$NR_2$=N-methyl-benzylamine (14f). MS (ES+=397.26).

$NR_2$=N,N,N-trimethylethylenediamine (14g). MS (ES+=378.33).

$NR_2$=N-methylpiperazine (14h). MS (ES+=376.32).

$NR_2$=2-piperidinemethanol (14i). MS (ES+=391.31).

$NR_2$=N-methylglycine t-butyl ester (14j). Yield=70%; mp=180–185° C.; $^1$H NMR (DMSO-$d_6$) δ 8.37 (t, 1H), 7.82 (m, 2H), 7.29 (t, 1H), 4.48 (m, 2H), 3.94 (s, 2H), 3.58 (m, 2H), 3.26 (s, 2H), 2.30 (s, 3H), 1.38 (s, 9H). Anal Calcd, for $C_{18}H_{24}N_4O_3$: C, 62.77; H, 7.02; N, 16.27. Found: C, 62.73; H, 7.05; N, 16.22.

EXAMPLE 5

Compounds of the following general formula II-5 may be synthesized, for example, by the following methods

II-5

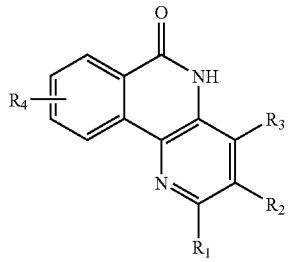

Scheme 1-5
General Scheme for synthesis of azaphenanthridone 4a-c.

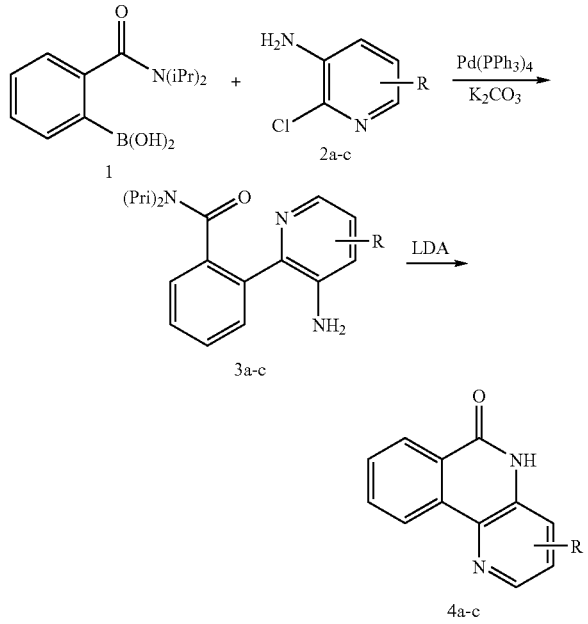

General procedure for the synthesis of amines 3a–c. The boronic acid 1 (2.0 g, 8.0 mmol) prepared according to Brimble, M. A.; Chan, S. H. Aust. J. Chem. 1998, 51, 235–242 was added to a solution of potassium carbonate (2.2 g in 8 mL $H_2O$) and 2-chloro-3-amino pyridine (0.94 g, 7.3 mmol) in 100 mL toluene/EtOH (8:1). This mixture was deoxygenated in vacuo and refilled with nitrogen. After stirring the mixture under nitrogen for 30 min, palladium tetrakistriphenylphosphine (250 mg) was added to the mixture. The solution was heated to 80° C. until complete conversion according to TLC (50/50 Hexanes/EtOAc). The reaction was then extracted with water and the toluene layer was dried and concentrated to yield a crude solid which was triturated with diethyl ether (10–20 mL) to yield 1.84 g (85%) of the desired amine 3a. $^1$H NMR ($CDCl_3$) δ 8.05 (d, 1H), 7.45 (m, 3H), 7.28 (d, 1H), 7.06 (m, 1H), 7.00 (d, 1H), 4.01 (s, 2H), 3.78 (m, 1H), 3.31 (m, 1H), 1.48 (d, 3H), 1.13 (d, 3H), 1.01 (d, 3H), 0.84 (d, 3H).

R=5-chloro amine 3b. Amide 3b was synthesized from 3-amino-2,5-dichloro-pyridine 2b (X=Cl, R=5-Cl) as stated above with the exception of purification by flash chromatography on the minimum amount of silica gel (10% EtOAc/Hexanes→50% EtOAc/Hexanes). Dry yield was 1.40 g (70%). $^1$H NMR ($CDCl_3$) δ 7.98 (s, 1H), 7.45 (m, 2H), 7.26 (m, 2H), 7.00 (d, 1H), 3.76 (m, 1H), 3.35 (m, 1H), 1.48 (d, 3H), 1.19 (d, 3H), 1.04 (d, 3H), 0.91 (d, 3H).

R=6-methoxy amine 3c. Amide 3c was synthesized from 3-amino-2-bromo-6-methoxypyridine 2c and boronic acid 1 as stated above. The dry yield was 74%. $^1$H NMR ($CDCl_3$) δ 7.43 (m, 3H, 7.27 (m, 1H), 7.08 (d, 1H), 6.61 (d, 1H), 3.83 (s, 3H), 3.70 (m, 1H), 3.30 (m, 1H), 1.49 (d, 3H), 1.15 (d, 3H), 0.99 (d, 3H), 0.75 (d, 3H).

4a

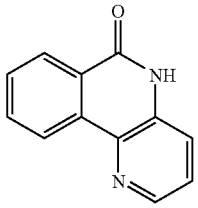

Azaphenanthridone 4a. The amide 3a (1.74 g, 5.8 mmol) was dissolved in dry tetrahydrofuran (25 mL) and cooled to −78° C. under nitrogen. Lithium diisopropylamide (2.0 M, 7.6 mL) was added to dropwise to the solution and this mixture was stirred for several hours and warmed to room temperature overnight. The reaction was quenched with water (50 mL) and extracted with 10% MeOH/DCM. The combined organics were dried and concentrated to yield the crude solid which was triturated with boiling diethyl ether to yield the pure material 4a 0.95 g (89%). Mp=300–320° C. (dec.); $^1$H NMR ($d_6$-DMSO) δ 11.78 (s, 1H), 8.77 (d, 1H), 8.55 (d, 1H), 8.32 (d, 1H), 7.93 (d, 1H), 7.74 (m, 2H), 7.54 (m, 1H). Anal Calcd. for $C_{12}H_{28}N_2O$: C, 73.46; H, 4.11; N, 14.28. Found: C, 72.80; H, 4.19; N, 14.06.

4b

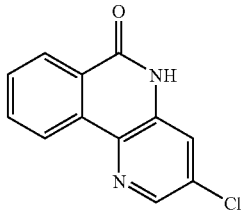

Chloroazaphenanthridone 4b. Chloride 4b was made in an analogous manner to compound 4a. Yield=74%; mp=295–300° C.; $^1$H NMR ($d_6$-DMSO) δ 11.80 (bs, 1H), 8.69 (d, 1H), 8.56 (s, 1H), 8.31 (d, 1H), 7.94 (t, 1H), 7.78 (m, 2H). Anal Calcd. for $C_{12}H_7ClN_2O$: C, 62.49; H, 3.60; N, 12.15. Found: C, 61.53; H, 3.21; N, 11.87.

4c

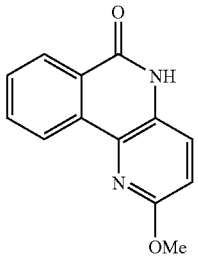

Methoxyazaphenanthridone 4c. Compound 4c was made from amide 3c in a similar manner to 4a. Yield 99%; mp=290–300° C.; $^1$H NMR ($d_6$-DMSO) δ 11.67 (bs, 1H), 8.69 (d, 1H), 8.30 (d, 1H), 7.93 (t, 1H), 7.72 (m, 2H), 7.03 (d, 1H), 4.01 (s, 3H). Anal Calcd. for $C_{13}H_{10}N_2O_2$: C, 69.02; H, 4.46; N, 12.38 Found: C, 67.89; H, 4.49; N, 12.08.

4d

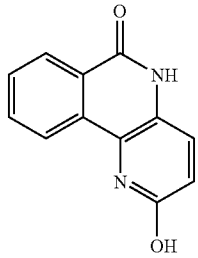

Hydroxyazaphenanthridone 4d. The methyl ether 4c (500 mg, 2.2 mmol) was dissolved in 10 mL HBr (48% in HOAc) in a sealed tube. The reaction was heated to 100° C. for 10 h. After cooling, the reaction was filtered and washed with acetic acid (3×10 mL) and dried in vacuo. The dry weight of the hydrobromide salt 4d was 421 mg, (90%). $^1$H NMR ($d_6$-DMSO) δ 11.61 (bs, 1H), 10.50 (bs, 1H), 8.62 (d, 1H), 8.30 (d, 1H), 7.89 (t, 1H), 7.71 (t, 1H), 7.65 (d, 1H), 6.81 (d, 1H). Anal Calcd. For $C_{12}H_9BrN_2O_2$: C, 49.17; H, 3.09; N, 9.56. Found: C, 48.75; H, 3.15; N, 9.36.

4e

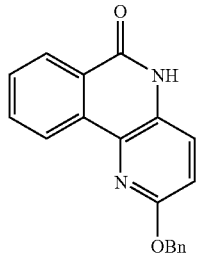

Benzyloxyazaphenanthridone 4e. The hydrobromide salt 4d (100 mg, 0.34 mmol) was dissolved in 3 mL DMF. Potassium carbonate (100 mg) and benzyl bromide (60 μL, 0.50 mmol) were added to the solution and the mixture was heated to 60° C. for 14 h. The solvent was removed in vacuo and the residue was washed with water (5 mL) and boiling MeOH (10 mL) and filtered. The solid 4e (47 mg, 46%) was pure while the filtrate contained a mixture of isomers. Mp=271–276° C. $^1$H NMR ($d_6$-DMSO) δ 11.68 (bs, 1H), 8.71 (d, 1H), 8.30 (d, 1H), 7.93 (t, 1H), 7.74 (m, 2H), 7.55 (d, 2H), 7.40 (t, 2H), 7.32 (t, 1H), 7.09 (d, 1H), 5.54 (s, 2H). Anal Calcd. for $C_{19}H_{14}N_2O_2(H_2O)$: C, 71.24; H, 5.03; N, 8.74. Found: C, 71.28; H, 4.83; N, 8.38.

Scheme 2-5
Synthesis of Aminoazaphenanthridone 4f.

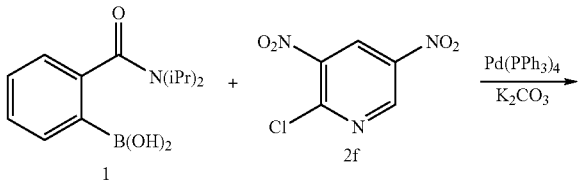

-continued

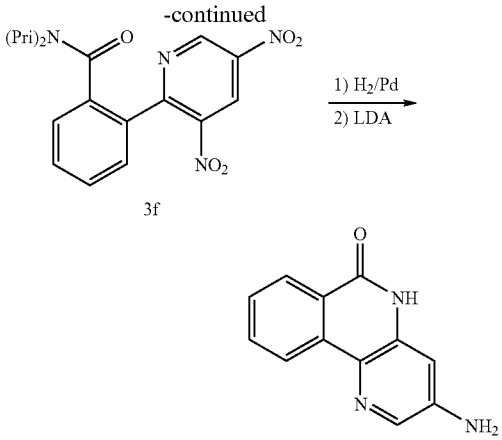

Dinitroamide 3f. The coupling of 2-chloro-3,5-dinitropyridine 2f with boronic acid 1 was accomplished as outlined in the procedure for 3a–c. $^1$H NMR ($CDCl_3$) δ 9.55 (s, 1H), 9.04 (s, 1H), 7.41 (m, 2H), 7.39 (t, 1H), 7.28 (d, 1H), 3.99 (m, 1H), 3.40 (m, 1H), 1.58 (bd, 3H), 1.50 (bd, 3H), 1.33 (bd, 3H), 1.20 (bd, 3H).

Aminoazaphenanthridone 4f. The dinitroamide 3f (700 mg, 1.88 mmol) was dissolved in 25 mL MeOH and added to a Parr flask under nitrogen with 100 mg of palladium on carbon. This mixture was reduced under an atmosphere of 30 psi of hydrogen for 2 h. The palladium was filtered off through a plug of celite and the filtrate was concentrated in vacuo and the crude diamine (550 mg, 94%) was used in the cyclization without any further purification. The diamine was redissolved in dry tetrahydrofuran and cyclized with LDA (3 eq) in a similar manner to amides 3a–c. Compound 4f was isolated in 56% yield (227 mg). Mp=>300° C. (dec.); $^1$H NMR ($d_6$-DMSO) δ 11.46 (bs, 1H), 8.49 (d, 1H), 8.17 (d, 1H), 7.95 (s, 1H), 7.77 (t, 1H), 6.79 (s, 1H), 5.92 (d, 2H). Anal Calcd. for $C_{12}H_9N_3O_2$: C, 62.87; H, 4.48; N, 18.33. Found: C, 62.18; H, 4.74; N, 18.17.

Scheme 3-5
Synthesis of chloroazaphenanthridone 4g.

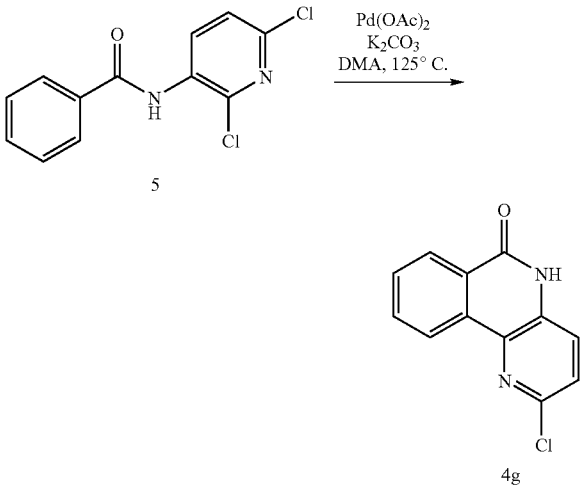

Chloroazaphenanthridone 4g. Amide 5 was prepared from commercial reagents, benzoyl chloride and 3-amino-2,6-dichloropyridine in DCM in high yield. The desired product 4g was prepared by dissolving amide 5 (4.45 g, 16.7 mmol) in DMA (35 mL) and adding sodium carbonate (1.8g, 16.7 mmol) and palladium acetate (400 mg, catalytic amt.). The reaction mixture was heated to 125° C. for several hours until the starting material was no longer present by TLC. The reaction was then cooled down to room temperature and concentrated in vacuo and the crude residue was suspended in boiling EtOAc (100 mL) and filtered through a plug of celite. The filtrate was concentrated and the solid that precipitated out was filtered off and determined to be compound 4g (520 mg, 13% yield). Mp=285–295 (dec.) ° C.; $^1$H NMR ($d_6$-DMSO) δ 11.92 (bs, 1H), 8.62 (d, 1H), 8.32 (d, 1H), 7.95 (t, 1H), 7.77 (m, 2H), 7.62 (d, 1H). Anal Calcd. for $C_{12}H_7ClN_2O$: C, 62.49; H, 3.06; N, 12.15. Found: C, 61.40; H, 3.19; N, 11.77.

Scheme 4-5
General Scheme for synthesis of azaphenanthridone amines 4h-x.

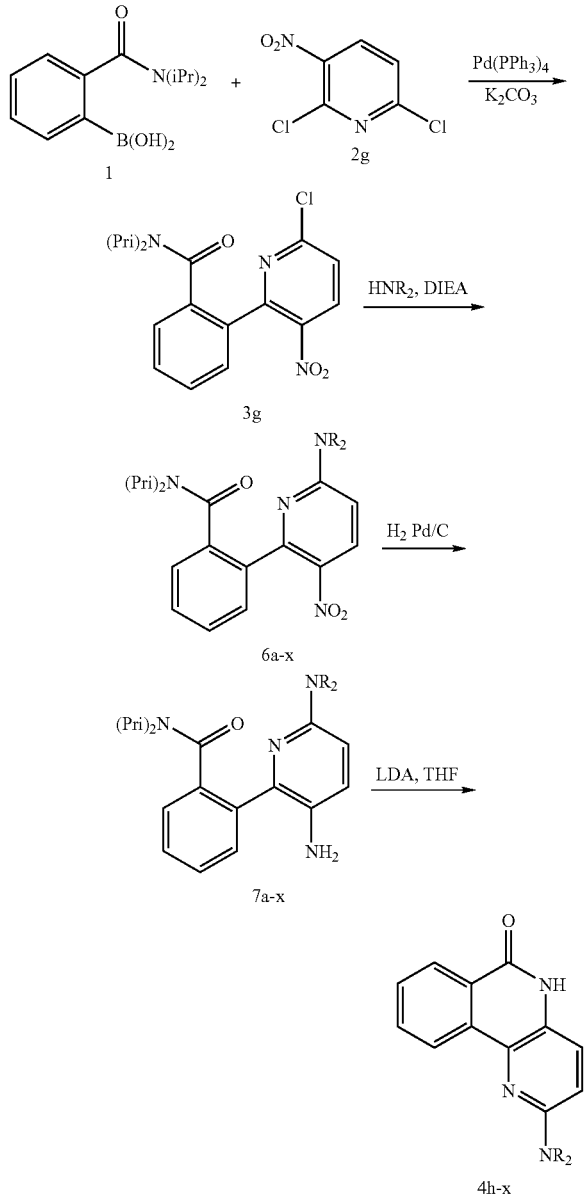

General procedure for the synthesis of nitro compound 3g. The boronic acid 1 (2.0 g, 8.0 mmol) prepared according to the literature was added to a solution of potassium carbonate (2.2 g in 8 mL $H_2O$) and 2,5-dichloro-3-nitro pyridine 2g (1.4 g, 7.3 mmol) in 100 mL toluene/EtOH (8:1). This mixture was deoxygenated in vacuo and refilled with nitrogen. After stirring the mixture under nitrogen for 30 min, palladium tetrakistriphenylphosphine (250 mg) was added to the mixture. The solution was heated to 80° C. until complete conversion (no starting material) according to TLC (50/50 Hexanes/EtOAc). The reaction was then extracted with water and the toluene layer was dried and concentrated to yield a crude oil which was columned on silica gel to afford the desired isomer 3g in 45% yield (1.20 g). $^1$H NMR ($CDCl_3$) δ 8.26 (d, 1H), 7.45 (m, 3H), 7.34 (m, 2H), 3.99 (m, 1H), 3.41 (m, 1H), 1.38 (bs, 9H), 1.21 (d, 3H).

General procedure for the synthesis of amines 6a–x. Chloride 3g (300 mg, 0.83 mmol) was dissolved in THF (5 mL) followed by the addition of diisopropylethylamine (160 μL, 0.91 mmol), and 2-(4-aminoethyl)morpholine (220 μL, 1.66 mmol). The reaction was heated to 65° C. overnight and TLC analysis indicated a low running spot on the baseline (EtOAc). Water (5 mL) was added to the mixture followed by extraction with DCM (3×10 mL). The combined organics were dried and concentrated to yield a crude foam which solidified upon drying in vacuo. The solid was triturated with hexanes and filtered to yield 320 mg (85%) of the desired amine 6a.

$NR_2$=aminoethylmorpholine (6a). Yield=85%. $^1$H NMR (DMSO-$d_6$) δ 8.21 (m, 1H), 7.40 (m, 5H), 6.30 (d, 1H), 3.97 (m, 1H), 3.70 (m, 6H), 3.47 (m, 2H), 3.31 (m, 1H), 2.45 (m, 6H), 1.48 (bs, 3H), 1.24 (bs, 3H), 1.06 (bs, 3H), 0.87 (bs, 3H).

$NR_2$=N-methylpiperazine (6b). Yield=72%; MS (ES+)=426.21.

$NR_2$=N-boc-[2.2.1]diazabicycloheptane (6c). Yield=72%; MS (ES+)=486.43.

$NR_2$=N-boc-piperazine (6d). Yield=72%; MS (ES+)=473.23.

$NR_2$=amino (6e). Yield=72%; MS (ES+)=343.31.

General procedure for the synthesis of analines 7a–x. Nitro compound 6a (300 mg, 0.66 mmol) was dissolved in MeOH (20 mL) with Pd/C (100 mg) and hydrogenated at 30 psi for 2 h. TLC indicated complete conversion of the nitro compound (10% MeOH/EtOAc). The reaction mixture was filtered through a plug of celite and the filtrate was concentrated and dried. The crude foam was used in the cyclization step without further purification. The dry yield of the aniline 7a was 275 mg (99%). $^1$H NMR ($CDCl_3$) δ 7.41 (m, 3H), 6.98 (d, 1H), 6.31 (d, 1H), 4.75 (bs, 2H), 3.78 (m, 1H), 3.70 (m, 4H), 3.28 (m, 3H), 2.56 (m, 2H), 2.47 (m, 4H), 1.50 (d, 3H), 1.19 (d, 3), 1.00 (d, 3H), 0.83 (d, 3H).

4h

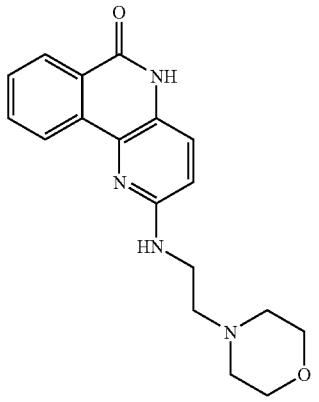

General procedure for the cyclization of anilines 7a–x. The crude aniline 7a (270 mg, 0.64 mmol) was dissolved in THF (20 mL) and cooled to −78° C. A 2.0M solution of LDA (1 mL) was added to the aniline and the reaction was slowly warmed to room temperature overnight. The mixture was quenched with water (10 mL) and extracted several times with EtOAc (3×15 mL). The combined organics were dried and concentrated and the resulting solid was triturated with EtOAc (3 mL) and filtered yielding 125 mg (58%) of the desired amine 4h. $^1$H NMR (DMSO $d_6$) δ 11.46 (s, 1H), 8.70 (d, 1H), 8.32 (d, 1H), 7.92 (t, 1H), 7.71 (t, 1H), 7.49 (d, 1H), 6.82 (d, 1H), 6.63 (t, 1H), 3.66 (m, 4H), 3.58 (m, 2H), 2.60 (m, 4H). MS ES+=324.9). Mp=250–255° C. Anal Calcd for $C_{18}H_{20}N_4O_2$(0.5 $H_2O$) C, 64.85; H, 6.35; N, 16.81. Found: C, 65.44; H, 6.27; N, 16.71.

4i

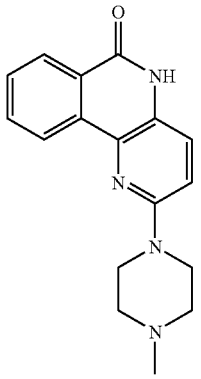

$NR_2$=N-methylpiperazine (4i). Yield 46%; mp=285–288° C.; $^1$H NMR ($CDCl_3$) δ 11.50 (s, 1H), 8.65 (d, 1H), 8.27 (d, 1H), 7.88 (t, 1H), 7.69 (t, 1H), 7.56 (d, 1H), 7.14 (d, 1H), 3.56 (t, 4H), 2.46 (t, 4H), 2.24 (s, 3H). Anal. Calcd for $C_{17}H_{18}N_4O$: C, 69.37; H, 6.16; N, 19.03. Found: C, 69.38; H, 6.15; N, 18.84.

4j

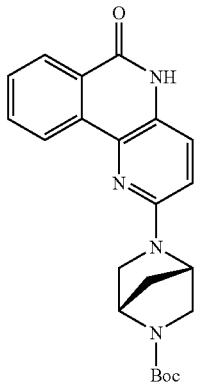

$NR_2$=(S,S)-N-Boc-[2.2.1] diazabicycloheptane (4j). Yield=36; mp=259–261° C.; $^1$H NMR (DMSO-$d_6$) δ 11.44 (s, 1H), 8.65 (d, 1H), 8.26 (d, 1H), 7.67 (t, 1H), 7.45 (d, 1H), 6.85 (t, 1H), 4.92 (dd, 2H), 3.38 (m, 2H), 3.30 (s, 1H), 3.23 (m, 1H), 1.96 (d, 2H), 1.60 (s, 9H). Anal Calcd. for $C_{22}H_{24}N_4O_3$: C, 67.33; H, 6.16; N, 14.28. Found: C, 67.30; H, 6.19; N, 14.21.

4k

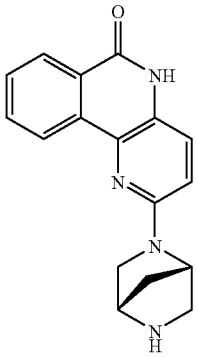

$NR_2$=[2.2.1]-diazabicycloheptane (4k). This compound was made by deprotection of the boc group by 10% TFA/DCM (16b). Yield=98%; mp=160–165° C.; $^1$H NMR (DMSO-$d_6$) δ 11.54 (s, 1H), 8.68 (d, 1H), 8.59 (d, 1H), 7.90 (t, 1H), 7.72 (t, 1H), 7.61 (d, 1H), 6.92 (d, 1H), 5.04 (s, 1H), 4.53 (s, 1H), 3.68 (m, 2H), 3.29 (m, 2H), 2.19 (d, 1H), 2.00 (d, 1H). Anal Calcd. for $C_{17}H_{16}N_4O$ (1.1 $C_2HF_3O_2$)(0.4 $H_2O$): C, 54.41; H, 4.00; N, 13.22. Found: C, 54.12; H, 4.26; N, 12.98.

4l

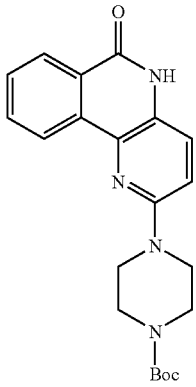

$NR_2$=Boc-piperazine (4l). Yield=48%; mp=231–235° C.; $^1$H NMR (DMSO-$d_6$) δ 11.52 (s, 1H), 8.67 (d, 1H), 8.27 (d, 1H), 7.89 (t, 2H), 7.70 (t, 2H), 7.58 (d, 1H), 3.50 (dd, 8H), 1.44 (s, 9H). Anal Calcd. for $C_{21}H_{24}N_4O_3$ (0.5 $H_2O$): C, 64.77; H, 6.47; N, 14.39. Found: C, 64.83; H, 6.39; N, 14.23.

4m

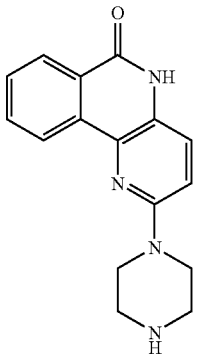

$NR_2$=piperazine (4m). This compound was made by the deprotection of the boc group with 10% TFA/DCM (16b). Yield=99%; mp=250–252° C.; $^1$H NMR (DMSO-$d_6$) δ 11.56 (s, 1H), 8.93 (bs, 1H), 8.65 (d, 1H), 8.27 (d, 1H), 7.87 (t, 1H), 7.70 (t, 1H), 7.61 (d, 1H), 7.21 (d, 1H), 3.61 (t, 4H), 3.26 (bs, 4H). Anal Calcd. for $C_{16}H_{16}N_4O$ (0.5 $H_2O$) (1.9 TFA): C, 47.18; H, 3.40; N, 11.11. Found: C, 47.39; H, 3.64; N, 11.18.

4n

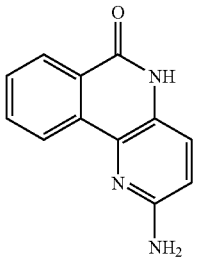

$NR_2$=amino (4n). Yield=50%; mp=310–315° C.; $^1H$ NMR (DMSO-$d_6$) δ 11.42 (s, 1H), 8.50 (d, 1H), 8.26 (d, 1H), 7.85 (t, 1H), 7.66 (t, 1H), 7.44 (d, 1H), 6.70 (d, 1H), 6.02 (d, 2H). Anal Calcd. for $C_{12}H_9N_3O$ (0.11 EtOAc): C, 67.64; H, 4.51; N, 19.02. Found: C, 67.98; H, 4.57; N, 18.67.

4o

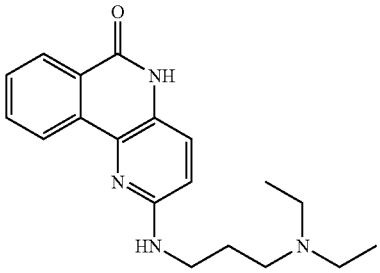

$NR_2$=N,N-diethyl aminopropyl (4o). Yield=45%; mp=114–116° C.; $^1H$ NMR (DMSO-$d_6$) δ 300 MHz 0.96(t, 6H, J=7.07, 7.73), 1.72(m, 2H), 2.49(m, 6H), 3.39(m, 2H), 6.70(d, 1H, J=8.84), 7.41(d, 1H, J=8.84), 7.65(t, 1H, J=8.08, 8.09), 7.84(t, 1H, J=8.09, 8.34), 8.24(d, 1H, J=7.83), 8.83 (d, 1H, J=7.83), 11.4 (s, 1H).

4p

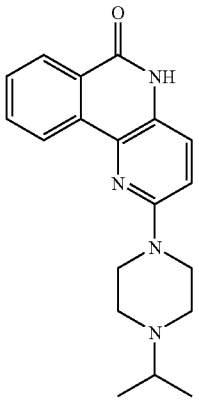

$NR_2$=N-isopropyl piperazine (4p). mp=260–264° C.; $^1H$ NMR (DMSO-$d_6$) δ 300 MHz 11.48(s, 1H), 8.63(d, J=7.44 Hz, 1H), 8.25(d, J=7.25 Hz, 1H), 7.86(t, J=8.2, 8.39 Hz, 1H), 7.67(t, J=8.20, 6.87 Hz, 1H), 7.53(d, J=9.15 Hz, 1H), 7.10(d, J=9.16 Hz, 1H), 3.55(t, J=4.96, 4.58 Hz, 4H), 2.68(m, 1H), 2.56(t, J=4.77, 4.77 Hz, 4H), 1.00(d, J=6.48 Hz, 6H). Anal Calcd. for $C_{19}H_{24}N_4O$: C, 70.8; H, 6.9; N, 17.2. Found: C, 70.9; H, 6.9; N, 17.2.

4q

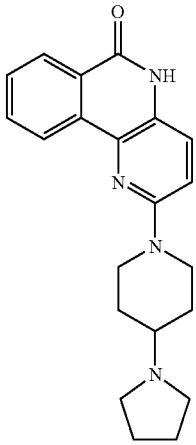

$NR_2$=pyrrolylpiperidine (4q). mp=170–175° C.; $^1H$ NMR ($D_2O$) δ 300 MHz 7.89(d, J=7.63 Hz, 1H), 7.80(d, J=7.82 Hz, 1H), 7.54(t, J=7.06, 7.63 Hz, 1H), 7.43(t, J=6.48, 7.44 Hz, 1H), 6.94(d, J=8.21 Hz, 1H), 6.54(d, J=7.25 Hz, 1H), 4.08(d, J=12.21 Hz, 2H), 3.63(t, J=9.72, 8.01 Hz, 2H), 3.31 (m, 1H), 3.13(m, 2H), 2.70(t, J=9.92, 12.02 Hz, 2H), 2.11–2.2(m, 4H), 1.94(q, 2H), 1.63(q, 2H). Anal Calcd. for $C_{21}H_{24}N_4O$ (1 $H_2O$) (1.4 HCl): C, 58.4; H, 6.4; N, 13.0; Cl, 11.5. Found: C, 58.7; H, 6.8; N, 12.8; Cl, 11.1.

4r

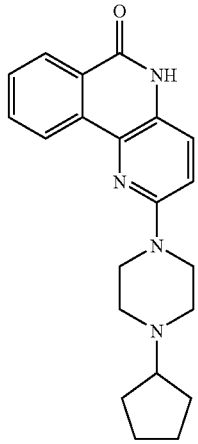

$NR_2$=N-cyclopentylpiperazine (4r). mp=285–290° C.; $^1H$ NMR (DMSO-$d_6$) δ 300 MHz 11.50 (s, 1H), 8.65(d, J=7.82 Hz, 1H), 8.28(d, J=8.01 Hz, 1H), 7.88(t, J=7.06, 6.86 Hz, 1H), 7.70(t, J=7.06, 7.06 Hz, 1H), 7.56(d, J=8.96 Hz, 1H), 7.13(d, J=9.16 Hz, 1H), 3.58(t, J=4.96, 4.20 Hz, 4H), 2.57(t, J=4.58, 4.57 Hz, 4H), 1.83(m, 2H), 1.64(m, 2H), 1.57(m, 1H), 1.50(m, 2H), 1.37(m, 2H). Anal Calcd. for $C_{21}H_{24}N_4O$ (0.2 $H_2O$): C, 71.7; H, 7.0; N, 15.9. Found: C, 71.6; H, 7.0; N, 15.7.

4s

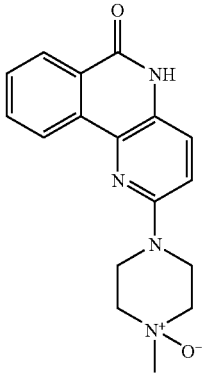

$NR_2$=N-oxo-N-methylpiperidine (4s). The synthesis of this compound and 4t was performed by the oxidation of 4i with excess mCPBA. $^1$H NMR ($D_2O$) δ 300 MHz 7.62 (d, J=6 Hz, 1H), 7.52 (d, J=9 Hz, 1H), 7.33 (m, 2H), 6.59 (d, J=9 Hz, 1H), 6.14 (d, J=9 Hz, 1H), 3.73 (m, 4H), 3.62 (t, 2H), 3.55 (s, 3H), 3.08 (t, 2H).

4t

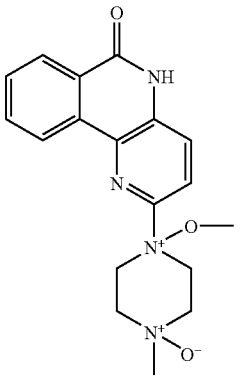

$NR_2$=N-oxo-methylpiperidine-N-oxide (4t). mp=230–235° C.; $^1$H NMR ($D_2O$) δ 300 MHz 7.97 (m, 2H), 7.51 (d, J=9 Hz, 1H), 7.43 (d, J=9 Hz, 1H), 7.36 (t, J=9 Hz, 1H), 7.27 (t, J=9 Hz, 1H), 4.88 (bt, 2H), 4.56 (bt, 2H), 3.96 (bd, 2H), 3.69 (s, 3H), 3.64 (bd, 2H). Anal Calcd. for $C_{17}H_{18}N_4O_3$ (1.25 $H_2O$): C, 50.1; H, 50.1; N, 13.8. Found: C, 50.7; H, 5.2; N, 13.8.

4u

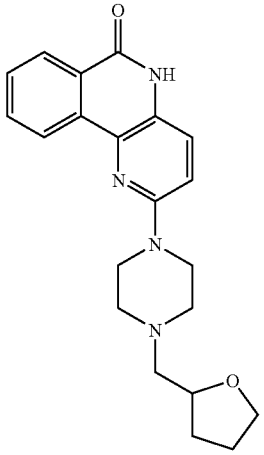

$NR_2$=N-methylfuranylpiperazine (4u). mp=270–275° C.; $^1$H NMR (DMSO-$d_6$) 300 MHz 11.49(s, 1H), 6.63(d, J=8.01 Hz, 1H), 8.25(d, J=7.82 Hz, 1H), 7.86(t, J=8.20, 8.21 Hz, 1H), 7.67(t, J=7.06, 7.06 Hz, 1H), 7.53(d, J=8.96, 1H), 7.11 (d, J=8.96 Hz, 1H), 3.96(m, 1H), 3.73(q, 1H), 3.59(q, 1H), 3.55(t, J=4.96, 3.44 Hz, 4H), 2.61(m, 2H), 2.55(m, 2H), 2.41 (m, 2H), 1.86–1.98(m, 1H), 1.75–1.82 (m, 2H), 1.43–1.47 (m, 1H). Anal Calcd. for $C_{21}H_{24}N_4O_2$(0.3 $H_2O$): C, 68.2; H, 6.7 N, 15.2. Found: C, 68.2; H, 6.7; N, 15.0.

4v

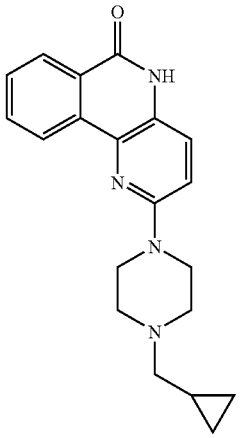

$NR_2$=N-cyclopropylmethylpiperazine (4v). $^1$H NMR (DMSO-$d_6$) 300 MHz 11.38 (bs, 1H), 8.55 (d, 1H), 8.17 (d, 1H), 7.76 (t, 1H), 7.58 (t, 1H), 7.46 (d, 1H), 7.05 (d, 1H), 3.49 (m, 4H), 2.40 (m, 4H), 2.12 (m, 2H), 0.77 (m, 1H), 0.39 (m, 2H), 0.00 (m, 2H).

4w

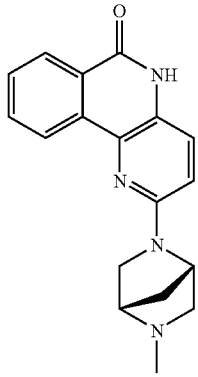

$NR_2$=N-methyl-[2.2.1]-diazabicycloheptane (4w). $^1H$ NMR (DMSO-$d_6$) 300 MHz 11.43 (bs, 1H), 8.66 (d, 1H), 8.27 (d, 1H), 7.84 (t, 1H), 7.70 (t, 1H), 7.53 (d, 1H), 6.81 (d, 1H), 4.73 (m, 1H), 3.52 (m, 1H), 3.48 (m, 1H), 3.37 (m, 1H), 3.34 (m, 1H), 2.87 (d, 1H), 2.28 (s, 3H), 1.86 (dd, 2H).

4x

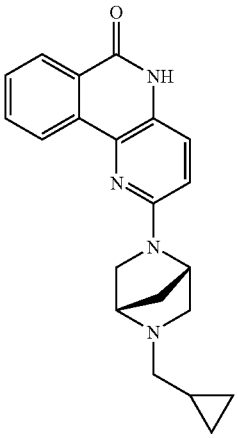

$NR_2$=N-cyclopropylmethyl-[2.2.1]-diazabicycloheptane (4x). MS (ES+) 347.28.

Scheme 5-5
Synthesis of the amines 8a-r.

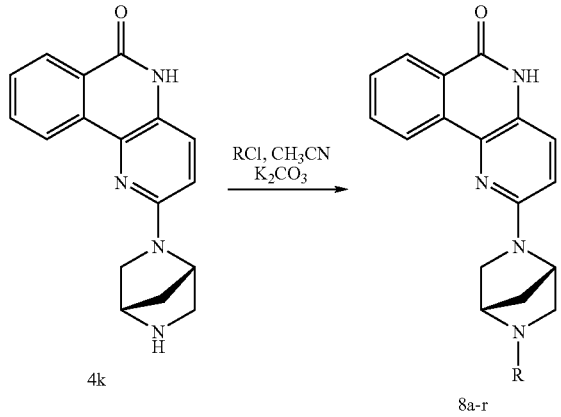

General procedure for the alkylation of amine 4k. Amine 4k (10 mg), excess $K_2CO_3$, and corresponding benzyl chloride were placed in test tubes in 1 mL $CH_3CN$. Those mixtures were heated to 60° C. on heat block overnight. EtOAc and 10% HCl were added. The organic layer was removed and the aqueous layer was basified with 10% NaOH. Extracted with EtOAc and then evaporated under reduced pressure. Compounds 8a–r were made in this manner.

R=$CR_2CN$ (8a). MS (ES+)=332.41.

R=$CH_2COOEt$ (8b). MS (ES+)=378.45.

R=$CH_2$-(2,5-dimethylphenyl) (8c). MS (ES+)=311.51.

R=$CH_2$-(4-fluorophenyl) (8d). MS (ES+)=401.45.

R=$CH_2$-(4-methoxyphenyl) (8e). MS (ES+)=413.49.

R=$CH_2$-(3,4-dimethylphenyl) (8f). MS (ES+)=411.23.

R=$CH_2$-(3,4-dichlorophenyl) (8g). MS (ES+)=451.36.

R=$CH_2$-(2-fluorophenyl) (8h). MS (ES+)=401.42.

R=$CH_2$-(3-methylphenyl) (8i). MS (ES+)=397.49.

R=$CH_2$-(3-chlorophenyl) (8j). MS (ES+)=417.83.

R=$CH_2$-(2-methylphenyl) (8k). MS (ES+)=397.41.

R=$CH_2$-(2-chlorophenyl) (8l). MS (ES+)=417.73.

R=$CH_2$-(4-carboxyphenyl) (8m). MS (ES+)=427.43.

R=$CH_2$-(3-carboxyphenyl) (8n). MS (ES+)=427.41.

R=$CH_2$-(4-methylphenyl) (8o). MS (ES+)=397.42.

R=$CH_2$-(4-benzyloxyphenyl) (8p). MS (ES+)=489.44.

R=$CH_2$-(3-fluorophenyl) (8q). MS (ES+)=400.42.

R=$CH_2$-(3-methylphenyl) (8r). MS (ES+)=412.43.

Scheme 6-5
Synthesis of the amines 9a-c.

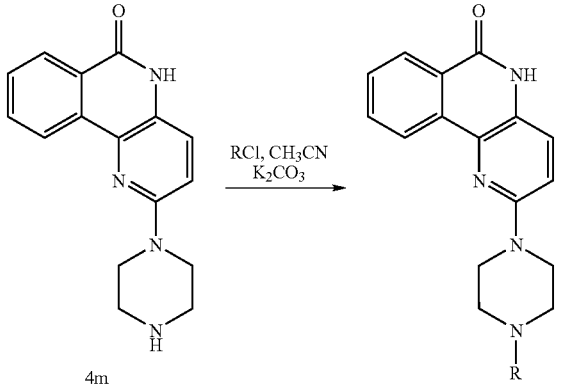

General procedures for parallel synthesis of amines 9a–c. To a mixture of the amine 4m, excess $K_2CO_3$, and corresponding bromomethylpyridines was added 1 mL $CH_3CN$. The reaction mixtures were heated to 90° C. for 4 h. Tris(2-aminoethyl)amine resin was added and heated to 70° C. for 1 h to remove excess of bromomethylpyridines. The mixtures were filtered and added to water (2 mL). Extracted with EtOAc. The organic layers were dried over $Na_2SO_4$ and evaporated under reduced pressure.

R=$CH_2$-(o-pyridine) (9a). MS (ES+)=372.41.

R=$CH_2$-(m-pyridine) (9b). MS (ES+)=372.40.

R=$CH_2$-(o-pyridine) (9c). MS (ES+)=372.41.

Scheme 7-5
Synthesis of the amines 11a-x.

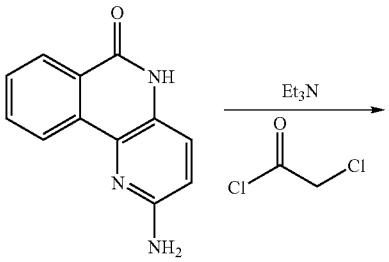

-continued

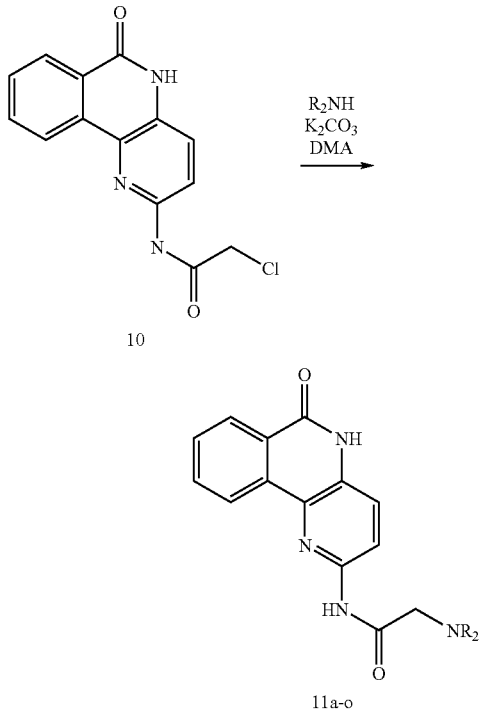

Procedure for synthesizing chloracetyl derivative (10). Amine 4n was dissolved in N,N'-dimethylacetamide and was cooled to 0° C. in ice bath. Triethylamine (1.1 eq) and Chloroacetylchloride (0.44 ml, 5.5 mmol) were added. The reaction mixture was stirred at room temperature under nitrogen over night. Solvent was evaporated under reduced pressure and the resulting brown residue was added water and 10% $NaHCO_3$. Solid was collected by filtration to yield 1.03 g (84% yield). Mp=287–290° C.; $^1H$ NMR (DMSO-$d_6$) δ 300 MHz 11.81(s, 1H), 10.94(s, 1H), 8.66(d, J=8.39, 1H), 8.31(d, J=7.63, 1H), 8.20(d, J=8.01, 1H), 7.96(t, J=7.82, 7.44, 1H), 7.77(m, 2H), 4.42(s, 2H). Anal Calcd. for $C_{14}H_{10}ClN_3O_2$: C, 58.5; H, 3.5; N, 14.6; Cl, 14.6. Found: C, 58.5; H, 3.6; N, 14.6; Cl, 14.6.

11a

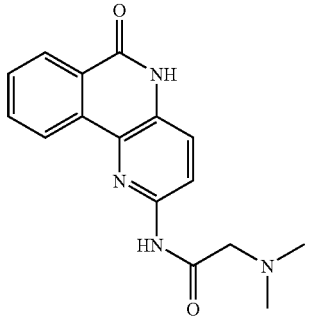

General procedure for the amination of chloride 10. Amination was carried out in a similar manner to 8a–r. $NR_2$=dimethylaminoacetyl (11a). mp=195–198° C.; $^1H$ NMR (DMSO-$d_6$) δ 300 MHz 7.87(d, J=7.44 Hz, 1H), 7.76(d, J=7.82 Hz, 1H), 7.56(t, J=7.24, 7.25 Hz, 1H), 7.47(m, 2H), 7.06(d, J=8.96 Hz, 1H), 4.15(s, 2H), 3.00(s, 6H). Anal Calcd. for $C_{16}H_{16}N_4O_2$(1.7 $H_2O$): (1.2 HCl): C, 50.8; H, 5.5; N, 14.8; Cl, 11.3. Found: C, 50.8; H, 5.5; N 14.7; Cl, 11.2.

11b

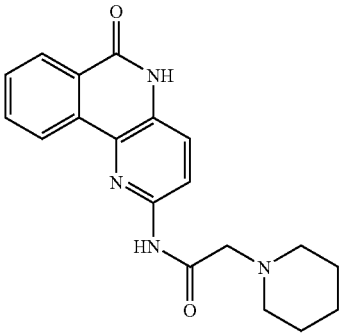

$NR_2$=piperidinylacetyl (11b). mp=175–180° C.; $^1H$ NMR (DMSO-$d_6$) δ 400 MHz 8.03(bd, J=8.33 Hz, 1H), 7.90(d, J=8.09 Hz, 1H), 7.66(d, J=7.33, 7.32 Hz, 1H), 7.59(d, J=7.83 Hz, 1H), 7.54(t, J=7.58, 7.33 Hz, 1H), 7.22(d, J=8.59 Hz, 1H), 4.12(s, 2H), 3.63(s, 2H), 3.13(s, 2H), 1.86(m, 6H). Anal Calcd. for $C_{19}H_{20}N_4O_2$(2 $H_2O$) (HCl): C, 54.4; H, 6.3; N, 13.4; Cl, 8.4. Found: C, 54.2; H, 6.0; N, 13.1; Cl, 8.6.

11c

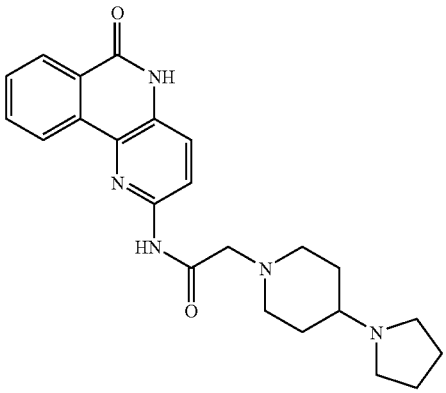

$NR_2$=pyrrolydylpiperidinylacetyl (11c). 300 MHz 7.61 (m, 2H), 7.47 (t, J=9 Hz, 1H), 7.38 (m, 2H), 6.90 (d, J=9 Hz, 1H), 3.68 (m, 2H), 3.50 (s, 2H), 3.33 (m, 4H), 2.68 (m, 2H), 2.39 (m, 3H), 1.87–2.12 (m, 6H). Anal Calcd. for $C_{23}H_{27}N_5O_2$(2 $H_2O$)(HCl): C, 57.8; H, 6.8 N, 14.7. Found: C, 57.8; H, 6.7; N, 14.6.

$NR_2$=2,3 tetrahydropyridine (11d). MS (ES−)=333.

$NR_2$=isoindole (11e). MS (ES−)=369.

$NR_2$=dipenylamine (11f). MS (ES−)=407.

$NR_2$=N-methylanisole (11g). MS (ES−)=387.

$NR_2$=N-methylbenzylamine (11h). MS ES−)=371.

$NR_2$=N-benzyl—N-phenethylamine (11i). MS (ES−)=461.

$NR_2$=N-hydroxyethylpiperazine (11j). MS(ES−)=381.

$NR_2$=N,N-dipropylamine (11k). MS (ES−)=351.

$NR_2$=4-oxopiperidine (11l). MS (ES−)=349.

$NR_2$=N,N-dibutylamine (11m). MS (ES−)=379.

$NR_2$=morpholine (11n). MS (ES−)=337. $NR_2$=imidazole (11o). MS (ES−)=318.

Scheme 8-5
Amide derivatives of aniline 4f.

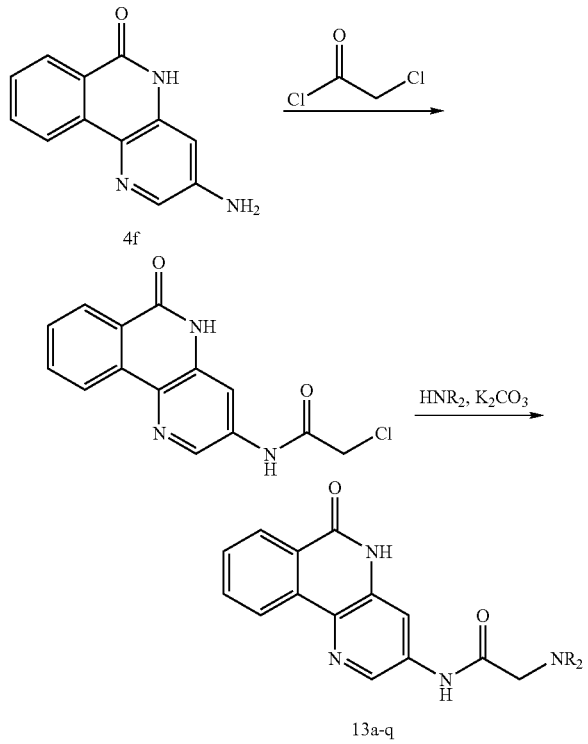

Chloride 12. The chloride 12 was synthesized identically to chloride 10. $^1H$ NMR ($d_6$-DMSO, 300 MHz): 11.81 (bs, 1H), 10.94 (s, 1H), 8.66 (s, 1H), 8.31 (s, 1H), 8.20 (d, 1H), 7.94 (t, 1H), 7.77 (m, 2H), 4.44 (s, 2H).

General procedure for the amination of chloride 12. The amination was carried out in a manner similar to amination of chloride 10 stated above.

13a

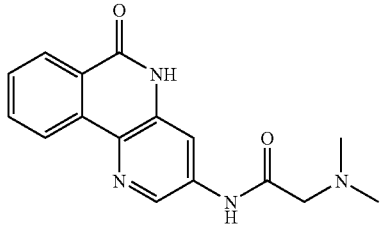

$NR_2$ dimethylamine hydrochloride (13a). $^1$HNMR ($D_2O$, 300 MHz): 7.82 (d, J=7.44 Hz, 1H), 7.76 (d, J=7.63 Hz, 1H), 7.70 (d, J=2.10 Hz), 7.63 (t, J=7.05, 7.63 Hz, 1H), 7.50 (t, J=7.06, 7.82 Hz, 1H), 7.40 (d, J=2.29 Hz, 1H), 4.16 (s, 2H), 3.03 (s, 6H).

13b

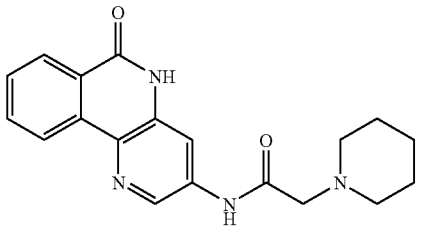

$NR_2$=piperidine hydrochloride (13b). $^1$HNMR ($D_2O$, 300 MHz): 400 MHz 8.03 (bd, J=8.33 Hz, 1H), 7.90 (d, J=8.09 Hz, 1H), 7.66 (t, J=7.33, 7.32 Hz, 1H), 7.59 (d, J=7.83 Hz, 1H), 7.54 (t, J=7.58, 7.33 Hz, 1H), 7.22 (d, J=8.59 Hz, 1H), 4.12 (s, 2H), 3.63 (s, 2H), 3.13 (s, 2H), 1.86 (m, 6H).

13c

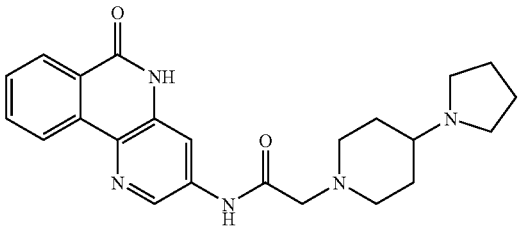

$NR_2$=pyrollylpiperidine (13c). $^1$HNMR ($D_2O$, 300 MHz) δ 7.48 (d, J=9 Hz, 1H), 7.31 (d, J=9 Hz, 1H), 7.29 (m, 2H), 7.17 (t, J=9 Hz, 1H), 6.99 (s, 1H), 3.58 (s, 2H), 3.43–3.31 (m, 5H), 3.22 (m, 2H), 2.91 (m, 2H), 2.74 (m, 2H), 2.48 (s, 6H), 2.14 (m, 2H), 1.89–1.65 (m, 6H). Anal Calcd. for $C_{23}H_{27}N_5O_2$(2 $H_2O$)(2 MsOH): C, 50.2; H, 5.9 N, 11.7. Found: C, 50.2; H, 6.0; N, 11.6.

$NR_2$=N-isopropylpiperidine (13d). $^1$HNMR ($D_2O$, 300 MHz) δ 300 MHz 7.78 (d, J=9 Hz, 1H), 7.60 (m, 3H), 7.50 (t, J=9 Hz, 1H), 7.23 (s, 1H), 3.74 (m, 3H), 3.47 (s, 2H), 3.40 (m, 4H), 2.90 (m, 2H), 1.55 (d, J=6 Hz, 6H). Anal Calcd. for $C_{21}H_{25}N_5O_2$ (2.25 $H_2O$) (1 HCl): C, 55.4; H, 6.5; N, 15.4. Found: C, 55.4; H, 6.6; N, 15.4.

$NR_2$=aminoethylpyrrolidine (13e). MS (ES+)=366.35.

$NR_2$=2-aminopropyl—N-methylpyrrolidine (13f). MS (ES+)=394.41.

$NR_2$=o-aminoethylpyridine (13g). MS (ES+)=374.30.

$NR_2$=m-aminoethylpyridine (13h). MS (ES+)=374.25.

$NR_2$=N-benzylpiperazine (13i). MS (ES+)=428.42.

$NR_2$=aminoethylmorpholine (13j). MS (ES+)=382.32.

$NR_2$=N,N-diethylethylenediamine (13k). MS (ES+)=368.31.

$NR_2$=N,N-dimethylethylenediamine (13l). MS=(ES+)=340.21.

$NR_2$=N,N-diethylpropylenediamine, (13m). MS (ES+)=382.41.

$NR_2$=N,N,N-trimethylpropylenediamine (13n). MS (ES+)=368.32.

$NR_2$=homopiperazine (13o). MS (ES+)=352.23.

$NR_2$=N-methylpiperazine (13p). MS (ES+)=352.32.

$NR_2$=piperonylpiperazine (13q). MS (ES+)=472.44.

$NR_2$=aminoethylpyrrolidin-2-one (13r). MS (ES+)=394.40.

$NR_2$=aminoethylpiperidine (13s). MS (ES+)=380.32.

Scheme 9-5
Alternate synthesis of the amines 4a-x.

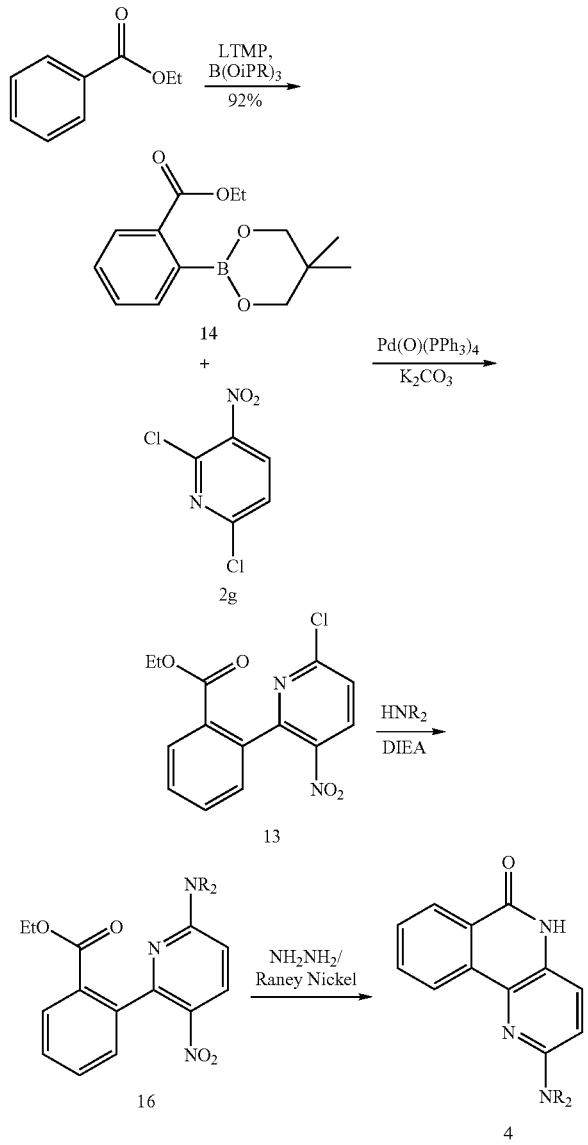

General alternate synthesis of amines 4a–x (example 4i). The proposed synthesis below would be more amenable to scale up. The boronic ester 14 can be made on a large scale (20 g) according to the literature reference (Kristensen, J. et al. Org. Lett. 2001, 3(10), 1435–1437). This synthesis cuts off one step, the LDA cyclization since the reduction/cyclization should work in the same step.

Synthesis of nitro chloride 15. The boronic ester 14 (16.0 g, 61.0 mmol), dinitro chloride 2g (11.7 g, 61 mmol) and potassium carbonate (21 g, 152 mmol) were dissolved in toluene/EtOH (20:1, 300 mL). This mixture was evacuated and refilled several times with nitrogen. Then, tetrakis-palladiumtriphenylphosphine (~2 g) was added followed by heating the mixture to 80° C. overnight. The reaction was then concentrated in vacuo and partitioned between EtOAc (200 mL) and $H_2O$ (200 mL). The organic layer was dried with sodium sulfate and concentrated in vacuo, The crude residue was chromatographed using a gradient system (5% EtOAc/Hexanes→20% EtOAc/Hexanes). The final product ($R_f$=0.3, 10% EtOAc/Hexanes) was isolated as a low melting solid/foam (7.12 g, 38%). Another 1.3 g (7.0%) of a mixture of isomers (other isomer $R_f$=0.25, 10% EtOAc/Hexanes) was isolated from the column. $^1$H NMR ($CDCl_3$, 300 MHz) δ 8.40 (d, 1H), 8.14 (d, 1H), 7.65 (t, 1H), 7.55 (m, 2H), 7.32 (d, 1H), 4.16 (q, 2H), 1.19 (t, 3H).

Synthesis of Diamine 16. The chloride 14 (7.12 g, 23.2 mmol) was dissolved in DCM (250 mL). Diisopropylethylamine (3.3 g, 25.5 mmol) was added to this solution followed by N-methylpiperazine (4.6 g, 46.4 mmol). This mixture was stirred overnight until complete conversion of the chloride was evident by TLC ($R_f$ of diamine=0.1, EtOAc). The reaction was worked up by extraction with water (2×100 mL). The organic layer was dried with sodium sulfate and concentrated in vacuo to yield the crude diamine 16 (6.56 g, 77%). $^1$H NMR ($CDCl_3$, 300 MHz) δ 8.32 (d, 1H), 8.07 (d, 1H), 7.58 (t, 1H), 7.48 (t, 1H), 7.26 (d, 1H), 6.60 (d, 1H), 4.13 (q, 2H), 3.73 (t, 4H), 2.46 (t, 4H), 2.33 (s, 3H), 1.13 (t, 3H).

Reduction/cyclization to form (4i). The crude diamine 16 was dissolved in MeOH (300 mL). Wet Raney nickel was added (500 mg, catalytic amount) followed by dropwise addition of hydrazine hydrate (4.1 g, 82 mmol). The mixture was heated to reflux and monitored by TLC until completion (approximately 3 h). The product $R_f$ value was 0.1 in 10% MeOH/EtOAc. The Raney nickel was then filtered off and the filtrate was concentrated and suspended in 1 N HCl/EtOAC (150 mL/100 mL) and the solid that resulted was filtered off and triturated with 50 mL of $CH_3CN$ and filtered. The resulting light yellow solid was dried under high vac for 2 h to yield 4.1 g (84% yield) of GPI 16539. $^1$H NMR (DMSO-$d_6$, 300 MHz) δ 11.50 (bs, 1H), 8.67 (d, 1H), 8.28 (d, 1H), 7.88 (t, 1H), 7.69 (t, 1H), 7.58 (d, 1H), 7.15 (d, 1H), 3.58 (t, 4H), 2.46 (t, 4H), 2.24 (s, 3H).

Mesylate salt formation (4i'). A solution of the diamine 4i (2.85 g, 9.7 mmol) in 500 mL dry THF was added methanesulfonic acid (0.65 mL, 10 mmol). The reaction mixture was stirred under $N_2$ at room temperature overnight. Off white solid was collected by filtration and washed with ether. The solid was vacuum dried to yield 3.2 g (85% yield).

EXAMPLE 6

Compounds of the following general formula II-6 may be synthesized, for example, by the following methods.

II-6

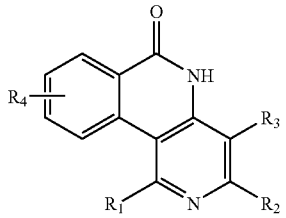

Scheme 1-6

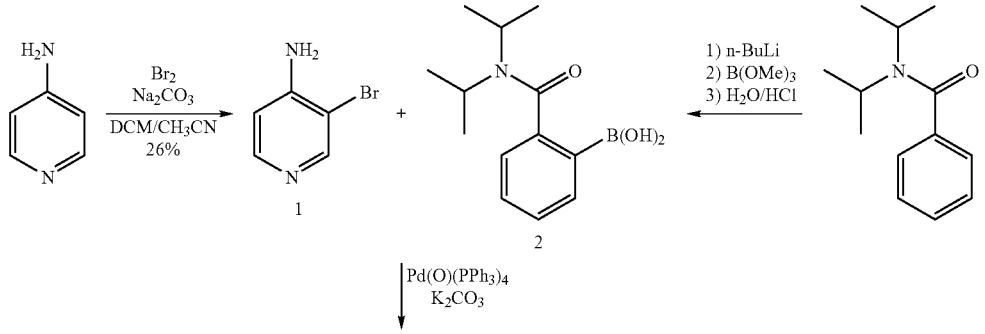

-continued

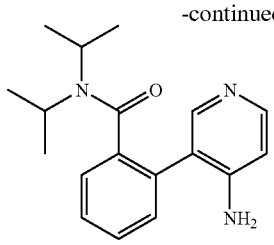

3

LDA, −78° C.

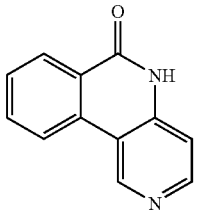

4

3-Bromo-4-aminopyridine (1). 4-Aminopyridine (3.0 g, 31.9 mmol) was dissolved in 100 mL of DCM and 60 mL $CH_3CN$. Bromine (5.1 g, 31.9 mmol) was added to this solution dropwise and the solution was stirred for 2 h. Sodium carbonate (6.2 g, 73.8 mmol) was added to the mixture and the reaction was stirred overnight. TLC (EtOAc) analysis of the reaction mixture showed two major spots, the higher running was 4-amino-3,5-dibromopyridine and the lower running one was the desired product ($R_f$=0.4, EtOAc). The reaction mixture was filtered and the filtrate was concentrated and chromatographed on a minimum amount of silica gel to yield 1.4 g (26%) of the desired product. $^1H$ NMR ($CDCl_3$): δ 8.39 (s, 1H), 8.10 (d, 1H), 6.60 (d, 1H), 4.74 (bs, 2H).

N,N-diisopropylbenzamide-boronic acid (2). Diisopropyl benzamide (10.0 g, 48.7 mmol) was dissolved in 200 mL of dry THF. This reaction was placed under inert atmosphere and cooled to −78° C. n-Butyl lithium (20.5 mL, 2.5 M) was added dropwise over a 15 minute period. This reaction mixture was stirred at this temperature for 4 h with a noticeable precipitation of the lithium salt. Trimethoxyborane (5.8 mL, 51.2 mmol) was added dropwise over a 10 minute period and the reaction was warmed to room temperature and stirred overnight. The reaction mixture was poured onto 300 g of ice and allowed to warm to room temperature. This mixture was partitioned in a separatory funnel and the aqueous layer was extracted once with 100 mL of DCM. The organic layer was acidified with conc. HCl and extracted with DCM (3×100 mL). The combined organic layers were dried and concentrated in vacuo. The residual foam was dried on high vac for several hours. The resulting material, 5.8 g (48%) was the desired product 2 as characterized spectroscopically (cis:trans amide): $^1H$ NMR ($CDCl_3$): δ 8.04 (d, 0.7H), 7.94 (d, 0.3H), 7.35 (m, 3H), 4.11 (m, 0.7H), 3.74 (m, 0.3H), 3.54 (m, 0.3H), 3.37 (m, 0.7H), 1.57 (d, 1.8H), 1.26 (m, 6H), 1.08 (d, 4.2H).

2-(4-amino-3-pyridinyl)-N,N-bis(1-methylethyl) benzamide (3). The bromopyridine 1 (1.4 g, 8.1 mmol), boronic acid 2 (2.0 g, 8.9 mmol) and potassium carbonate (2.2 g, 15.9 mmol) were dissolved in 80 mL toluene, 8 mL EtOH and 8 mL $H_2O$. This mixture was evacuated and refilled with nitrogen several times. Then, tetrakistriphenylphosphine palladium (0) (350 mg, 0.30 mmol) was added to the mixture and the mixture was heated to 80° C. overnight. Water (100 mL) was then added to the reaction and the organic layer was partitioned. The aqueous layer was extracted with EtOAc (2×100 mL) and the combined organics were dried with $Na_2CO_3$ and concentrated. The crude reaction product was triturated with diethyl ether (25 mL) and filtered. The resulting solid (2.0 g, 83%) was collected and characterized as the biphenyl amine 3. $^1H$ NMR ($CDCl_3$): δ 8.17 (d, 1H), 8.03 (s, 1H), 7.45 (m, 2H), 7.25 (m, 2H), 6.55 (d, 1H), 4.50 (bs, 2H), 3.61 (m, 1H), 3.31 (m, 1H), 1.49 (d, 3H), 1.16 (d, 3H), 1.03 (d, 3H), 0.83 (d, 3H).

benzo[c]1,6-napthyridine-6-(5H)-one (4). A solution of lithium diisopropyl amide (LDA, 2.0 M, Aldrich, 10 mL) was dissolved in 90 mL of THF and cooled to −78° C. A solution of amine 3 (2.0 g, 6.73 mmol) in THF (25 mL) was added to the LDA dropwise over a 15 minute period. The reaction was warmed to room temperature and stirred overnight. The reaction was concentrated in vacuo and suspended in 100 mL water. The solid was filtered off and triturated with ethyl acetate (100 mL). The resulting solid was dried to yield 1.24 g (94%) of the desired compound 4. An analytical sample can be obtained by recrystallization with copious amounts of methanol. $^1H$ NMR (DMSO): δ 9.57 (s, 1H), 8.65 (d, 1H), 8.50 (d, 1H), 8.33 (d, 1H), 7.90 (t, 1H), 7.71 (t, 1H), 7.28 (d, 1H). Anal Calcd for $C_{12}H_8N_2O$: C, 73.46; H, 4.11; N, 14.28. Found: C, 73.53; H, 4.26; N, 14.37.

EXAMPLE 7

The following general formulas I-7a and I-7b may be synthesized, for example, as follows.

I-7a

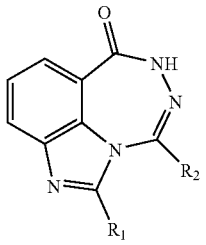

I-7b

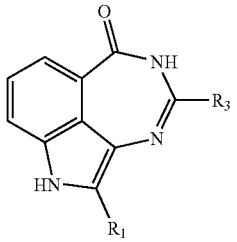

Scheme 1-7
Synthesis of Imidazolobenz-1,3,4-triazepin-5-one

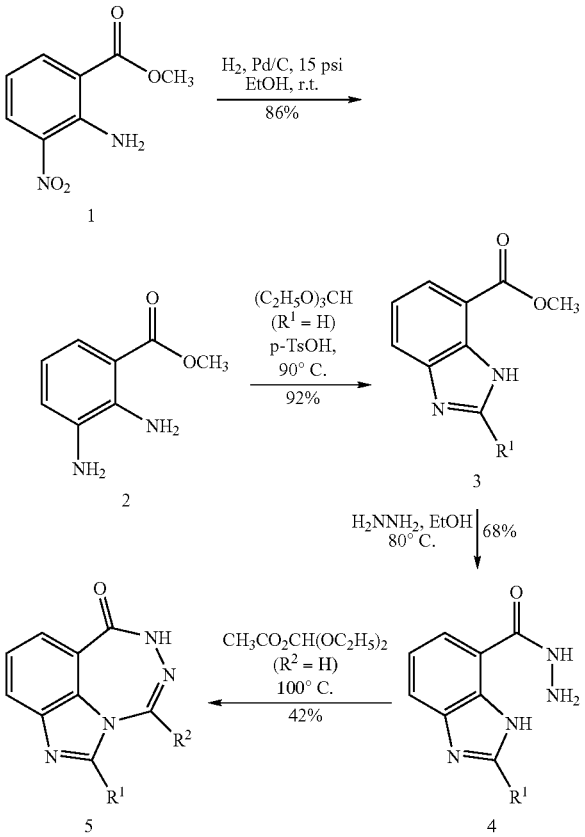

Synthesis of 2,3-Diaminobenzoic Acid Methyl Ester (2). 2-Amino-3-nitro benzoic acid methyl ester 1 (1.0 g, 5.1 mmol) and palladium on carbon (10%, 0.5 g) were mixed in EtOH (20 mL) and were hydrogenated at 15 psi for 1 h. The catalyst was filtered off and the filtrate was concentrated in vacuo. The resulting solid was dried to give 0.73 g (86%) of pure 2: $^1$H NMR ($CDCl_3$) δ 7.47 (d, 1H, J=8.0 Hz), 6.85 (d, 1H, J=6.5 Hz), 6.60 (t, 1H, J=8.0 Hz), 3.87 (s, 3H).

Synthesis of Benzimidazole-7-Carboxylic Acid Methyl Ester ($R^1$=H) (3). Ester 2 (1.7 g, 10.2 mmol), triethyl orthoformate (2.5 mL) and p-toluenesulfonic acid (10 mg) were mixed in "Performance Fluid" (3M Co., 40 mL) and refluxed with reversed Dean-Stark trap at 90° C. for 3 h. The reaction mixture was cooled to room temperature and the solid formed was filtered, washed with hexanes and dried to give 1.65 g (92%) of pure 3: $^1$H NMR (DMSO-$d_6$) δ 12.59 (br.s, 1H), 8.32 (s, 1H), 7.97 (d, 1H, J=8.0 Hz), 7.86 (d, 1H, J=6.5 Hz), 7.32 (t1, 1H, J=8.0 Hz), 3.95 (s, 3H).

Synthesis of Benzimidazole-7-Carboxylic Acid Hydrazide ($R^1$=H) (4). Benzimidazole ester 3 (1.65 g, 9.36 mmol), hydrazine monohydrate (10 mL), and water (3 mL) were refluxed in EtOH (60 mL) for 24 hs. Reaction mixture was cooled to room temperature and solid formed was filtered, washed with EtOH and dried to give 1.13 g (68%) of pure 4: $^1$H NMR (DMSO-$d_6$) δ 12.31 (br.s, 1H), 10.59 (s, 1H), 8.44 (s, 1H), 7.86 (d, 1H, J=6.5 Hz), 7.76 (d, 1H, J8.0 Hz), 7.34 (t, 1H, J=8.0 Hz), 4.68 (s, 1H).

Synthesis of Imidazolobenz-1,3,4-Triazepin-5-one ($R^1$=$R^2$=H) (5). Hydrazide 4 (0.25 g, 1.42 mmol) and diethoxymethylacetate (10 mL) were mixed and refluxed for 3 h. The reaction mixture was cooled to room temperature, and the resulting white solid was filtered, washed with hexanes (10 mL) and dried to give 0.109 g (42%) of pure 5: mp=266–268° C.; $^1$H NMR (DMSO-$d_6$) δ 12.80 (br.s, 1H), 9.45 (s, 2H), 8.35 (s, 1H), 7.93 (d, 1H, J=8.0 Hz), 7.89 (d, 1H, J=8.0 Hz), 7.42 (t, 1H, J=8.0 Hz).

EXAMPLE 8

Compounds of the following general formula I-8 may be synthesized, for example, by the following methods.

I-8

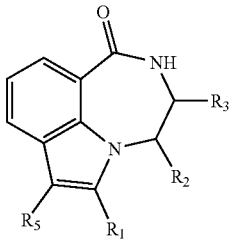

Scheme 1-8

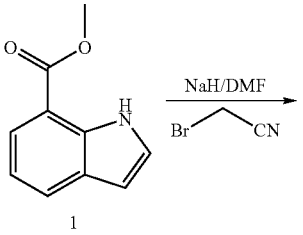

-continued

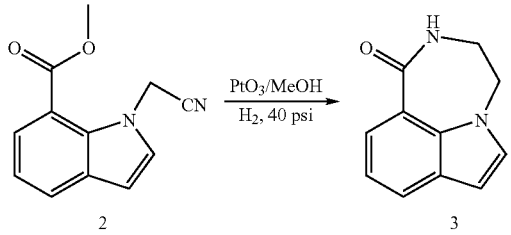

A solution of methyl indole-7-carboxylate (0.56 g, 3.2 mmol), 1, in dry DMF (4 mL) was added dropwise to a stirred ice-cooled suspension of sodium hydride (0.18 g of an 60% dispersion in mineral oil, 4.5 mmol) in dry DMF (3 mL) under a $N_2$ atmosphere. After the addition, the mixture was stirred at 0° C. for 30 min, then bromoacetonitrile (0.31 mL, 4.5 mmol) was added dropwise. The resulting mixture was stirred at room temperature overnight, then poured into ice-water, and extracted with ethyl acetate. The organic phase was washed with water, brine, dried over sodium sulfate, and concentrated in vacuo to give a residue, which was purified by flash column chromatography (silica gel; hexanes/ethyl acetate, 8:2) to give compound 2 (0.18 g, 26%) while recovering some starting material 1 (0.25 g). $^1$H NMR (400 MHz, $CDCl_3$) of 2: 7.90 (dd, 1H), 7.83 (dd, 1H), 7.21 (t, 1H), 7.11 (d, 1H), 6.67 (d, 1H), 5.51 (s, 2H), 4.00 (s, 3H).

A solution of compound 2 (0.10 g, 0.47 mmol) in MeOH (20 mL) was hydrogenated over platinum oxide ($PtO_2$, 10 mg) at 40 psi of $H_2$ for 15 h at room temperature. The catalyst was filtered on Celite, and the filtrate was concentrated in vacuo. The residue was purified by flash chromatography (silica gel; ethyl acetate/acetone, 9:1) to yield the title compound 3 (43 mg, 49%). MS: (M+1): 187. $^1$H NMR ($CDCl_3$, 400 MHz) 8.13 (dd, 1H), 7.84 (dd, 1H), 7.25 (t, 1H), 7.10 (d, 1H), 6.85 (s, br, 1H), 6.62 (d, 1H), 4.45 (m, 2H), 3.82 (m, 2H), Anal: Calcd for (C11H10N20+0.11 EtOAc): C, 70.14; H, 5.60; N, 14.30. Found: C, 70.53; H, 5.65; N, 14.74. MP: 164–167° C., Physical Form: Off white solid.

EXAMPLE 9

Compounds of the following general formula II-9 may be made, for example by the following general scheme.

II-9

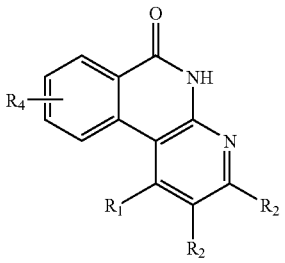

Scheme 1-7
General synthesis of 4-azaphenanthridones 14

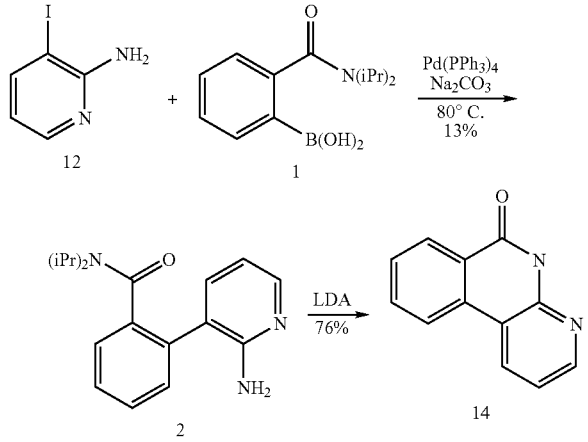

Synthesis of aniline 13. This coupling procedure was similar to the synthesis of amines 3a–c. Yield=13%; $^1$H NMR (DMSO-$d_6$, 300 MHz) δ 7.95 (m, 1H), 7.44 (m, 2H), 7.29 (m, 2H), 6.58 (m, 2H), 5.49 (bs, 2H), 3.56 (m, 1H), 3.29 (m, 1H), 1.39 (d, 3H), 1.05 (d, 3H), 0.93 (d, 3H), 0.64 (d, 3H).

Cyclization of aniline 13 to form 4-azaphenanthridone 14. The cyclization was carried out in a similar manner to compound 4a. Yield=76%; MS (ES+)=197.21; $^1$H NMR (DMSO-$d_6$, 300 MHz) δ 12.05 (bs, 1H), 8.85 (d, 1H), 8.56 (d, 1H), 8.51 (d, 1H), 8.37 (d, 1H), 7.91 (m, 1H), 7.71 (t, 1H), 7.33 (m, 1H). Anal. Calcd for $C_{12}H_8N_2O$: C, 73.46; H, 4.07; N, 14.12. Found: C, 73.06; H, 4.07; N, 14.12.

EXAMPLE 10

Compounds of the following general formula II-10 may be made, for example by the following general scheme.

II-10

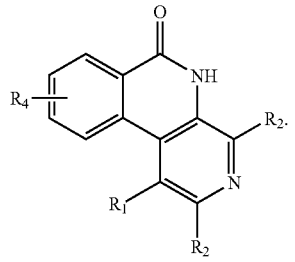

Scheme 1-10
General Synthesis of 3-azaphenanthridones.

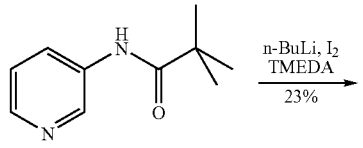

-continued

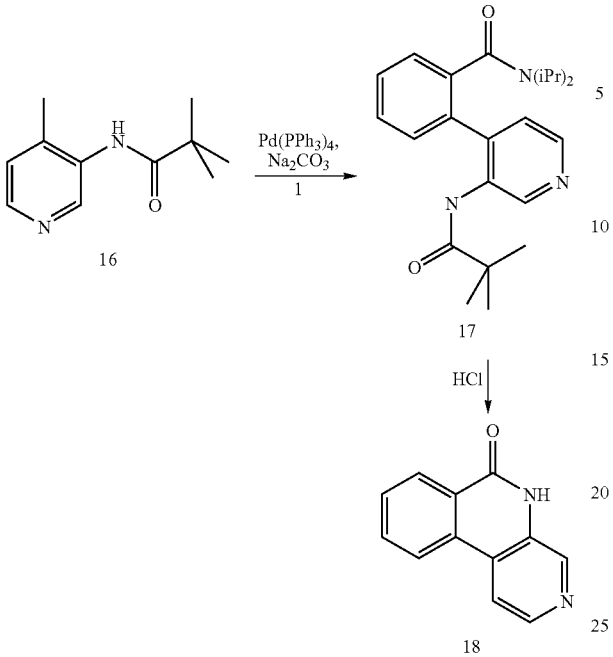

Iodopyridine 16. The 3-(Pivaloylamino)pyridine 15 (1.9 g, 11 mmol) and tetramethylethylene-diamine (4.0 mL, 26 mmol) were dissolved in dry THF (60 mL) and cooled to −78° C. While maintaining the temperature between −78° C. and −65° C., nBuLi (2.5 M solution in hexanes, 10.6 mL, 26.5 mmol) was added dropwise. The reaction was allowed to warm to −10° C. for 2 h, and then cooled back down to −78° C. Iodine (6.73 g, 26.5 mmol) dissolved in dry THF (20 mL) was added slowly. After stirring for 2 h at −78° C., the reaction was quenched with ice. Excess iodine was destroyed with addition of saturated potassium thiosulfate solution. The product was extracted with $CH_2Cl_2$, and the organic layers were washed with brine. The mixture was concentrated in vacuo to a black oil which was chromatographed (1:1 EtOAc/Hexanes; 2:1 EtOAc/Hexanes) to give 700 mg (23%) of 2,2-dimethyl-N-(4-iodo-3-pyridinyl) propanamide as a yellow solid. $^1$HNMR (DMSO-$d_6$ 300 MHz) δ 9.24 (s, 1H), 8.35 (s, 1H), 8.04 (d, 1H), 7.95 (d, 1H), 1.26 (s, 9H). MS (ES+)=305.

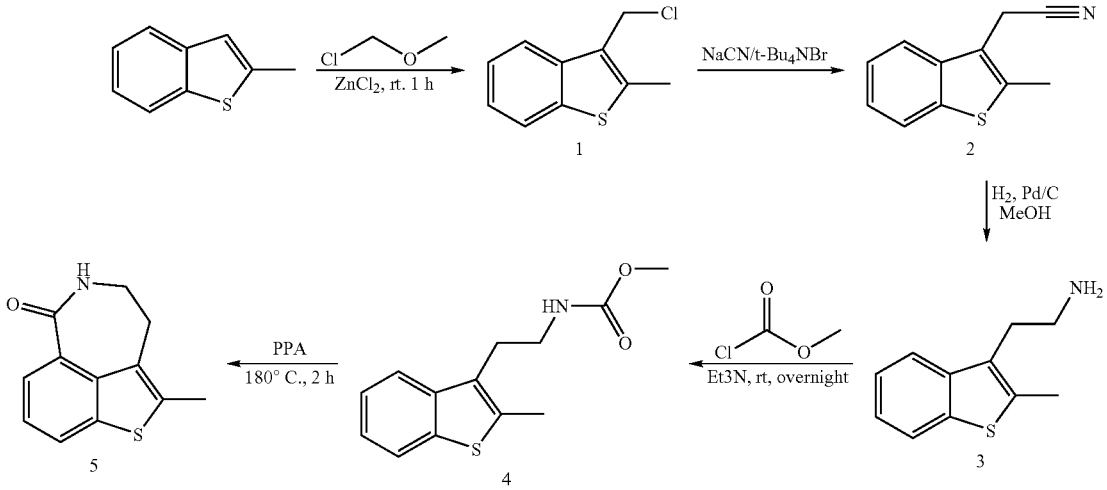

Bis amide 17. The 2,2-dimethyl-N-(4-iodo-3-pyridinyl) propanamide (700 mg, 2.3 mmol) and 2-diisopropylbenzamide boronic acid (1.3 g, 5.2 mmol) were dissolved in DME. Tetrakis(triphenylphosphine) palladium (133 mg, 0.11 mmol) and 2 M sodium carbonate solution (2.2 mL) were added. The reaction was refluxed at 83° C. for 18 h. The mixture was concentrated in vacuo, extracted with EtOAc, washed with brine and dried with sodium sulfate. The crude oil was chromatographed ($CH_2Cl_2$, 1%–5% MeOH/$CH_2Cl_2$) to obtain 2-[3-(2,2-dimethyl-propionylamino)-pyridin-4-yl]-N,N-diisopropylbenzamide as a white solid. $^1$HNMR (DMSO-$d_6$, 300 MHz) δ 9.08 (s, 1H), 8.64 (s, 1H), 8.43 (d, 1H), 7.58–7.48 (m, 2H), 7.40 (dd, 1H), 7.33 (d, 1H), 7.24 (dd, 1H), 3.53–3.36 (m, 2H), 1.38 (d, 3H), 1.01 (d, 3H), 0.97 (s, 9H), 0.91 (d, 3H), 0.77 (d, 3H); MS (ES+)=382.

Synthesis of 3-azaphenanthridone 18. All of 2-[3-(2,2-dimethyl-propionylamino)-pyridin-4-yl]-N,N-diisopropylbenzamide from the previous step was carried on and dissolved in methanol (20 mL). Concentrated HCl (1 mL) was added, followed by 24 h of refluxing. A white solid which precipitated out of solution was filtered and dissolved in $H_2O$. After 15 minutes of stirring, the free base crashed out of solution. The solid was filtered and dried, providing 150 mg (33% for two steps) of the desired final product as a white solid. Mp=303–309° C.; $^1$H NMR (DMSO-$d_6$, 300 MHz) δ 8.70 (s, 1H), 8.60 (d, 1H), 8.41 (t, 2H), 8.31 (d, 1H), 7.95 (t, 1H), 7.80 (t, 1H); $C_{12}H_8N_2O$.(0.3 $H_2O$).(0.2 ClH). Anal: Calcd for: C, 68.99; H, 4.25; N, 13,41. Found: C, 68.83; H, 3.99; N, 13.26.

EXAMPLE 11

Compounds of the general formula I-3c may be made, for example by the following general scheme.

3-chloromethyl-2-methylbenzo[b]thiophene 1 To a solution of chloromethyl methyl ether(30.0 g) in dichloroethane (250 mL) was added 2-methylbenzothiophene (2.0 g, 0.014 mol) and $ZnCl_2$ (200 mg). The resulting mixture was stirred for 1 h. The reaction mixture was poured into water and extracted with chloroform. The organic layer was dried ($MgSO_4$) and concentrated to afford the compound 1 (2.4 g, 90% yield) which was used directly in next step.

3-Acetonitril-2-methylbenzo[b]thiophene 2 To a solution of 1 (1.4 g, 7.7 mmol) in benzene (10 mL) was added NaCN (2.5 g) in water (10 mL) and tetrabutylammonium bromide (7.7 mmol). The solution was vigorously stirred at 60° C. for 2 h. The reaction mixture was poured into water, and extracted with benzene. The organic layers were dried ($MgSO_4$), filtered, and concentrated. The purification via column chromatography (2% EtOAc in hexanes to 10%) afford the compound 2 as an white solid (1.07 g, 74% yield): $^1$HNMR ($CDCl_3$) δ 7.77 (d, J=8.0 Hz, 1H), 7.67 (d, J=8.0 Hz, 1H), 7.41 (dt, J=1.0, 7.0, 8.0 Hz, 1H), 7.33 (dt, J=1.0, 7.0, 8.0 Hz, 1H), 3.81 (s, 1H), 2.58 (s, 1H).

3-Ethylamino-2-methylbenzo[b]thiophene hydrogen chloride 3 To a stirring solution of LAH (1N in $Et_2O$, 5.13 mL, 5.13 mmol) in $Et_2O$ (20 mL) was added $AlCl_3$ (684 mg, 5.13 mmol) gradually under $N_2$ at r.t. After 5 min, a solution of 2 (960 mg, 5.13 mmol) in $Et_2O$ (10 mL) was added dropwise in 10 min. The resulting mixture was refluxed overnight. After the reaction, the reaction mixture was cooled to r.t., neutralized with a 20% aqueous solution of Rochelle's salt, extracted with EtOAc. The organic layers were dried ($Na_2SO_4$), filtered, and concentrated. The resulting residue was dissolved in MeOH (15 mL) and 4N HCl solution in 1,4-dioxane (2.5 mL) was added dropwise. Solvent was removed and the resulting product 3 as an white solid (1.16 g, quantitively) was used directly in the next step: $^1$HNMR ($CD_3OD$) δ 7.64 (d, J=8.1 Hz, 1H), 7.59 (d, J=7.8 Hz, 1H), 7.25 (dt, J=1.0, 7.1, 8.1 Hz, 1H), 7.16 (dt, J=1.0, 7.1, 8.1 Hz, 1H), 2.94–3.09 (m, 4H).

Methyl [2-(2-methylbenzo[b]thien-3-yl)ethyl]-carbamate 4 To a suspension of 3 (1.16 g, 5.13 mmol) in $CH_2Cl_2$ (30 mL) was added methyl chloroformat (0.43 mL, 5.5 mmol) and $Et_3N$ (2.1 mL, 15.3 mmol) under $N_2$ at r.t. The resulting mixture was stirred continuously overnight. After the reaction, water was added, and extracted with $CH_2Cl_2$. The organic layers were dried ($MgSO_4$), filtered, and concentrated. Purification via column chromatography (10% EtOAc in hexanes to 20%) afforded the compound 4 as an white solid (1.0 g, 79% yield): $^1$HNMR ($CDCl_3$) δ 7.74 (d, J=7.8 Hz, 1H), 7.65 (d, J=7.8 Hz, 1H), 7.84 (dt, J=1.3, 8.3, 7.1, 6.8, 8.1 Hz, 1H), 7.26 (dt, J=1.3, 8.1, 6.8, 7.1, 8.3, 1H), 3.67 (s, 3H), 3.39 (q, J=6.8, 13 Hz, 2H), 3.01 (t, J=7.1, 6.8 Hz, 2H), 2.50 (s, 3H).

4,5-Dihydro-2-methylthieno[4,3,2-ef][2]benzazepin-6(3H)-one 5 A mixture of 4 (170 mg, 0.68 mmol) and PPA (1 mL) was heated at 180° C. for 2 h. Then the reaction mixture was cooled to r.t., and water was added. The resulting mixture was neutralized to pH ~5 with 3N aq. NaOH solution, and extracted with EtOAc. The organic layers were dried ($MgSO_4$), filtered, and concentrated. The purification via column chromatography (2% MeOH in $CH_2Cl_2$) afforded the compound 5 as an yellow solid (20 mg, 14% yield): mp 195–197° C., $^1$HNMR ($CDCl_3$) δ 8.21 (dd, J=1.0, 7.6 Hz, 1H), 7.91 (dd, J=1.0, 7.8 Hz, 1H), 7.37 (t, J=7.6, 7.8 Hz, 1H), 3.60 (q, J=5.6, 9.6 Hz, 2H), 3.01–3.08 (m, 2H), 2.48 (s, 3H); MS: 218 ($ES^+$); Anal. Calcd. for $C_{12}H_{11}NOS$: C, H, N.

EXAMPLE 12

Compounds of the general formula I-11, may be prepared as follows:

Preparation of 2,7-Dihydro-1,2,7,8-tetraaza-benzo[cd] azulen-6-one

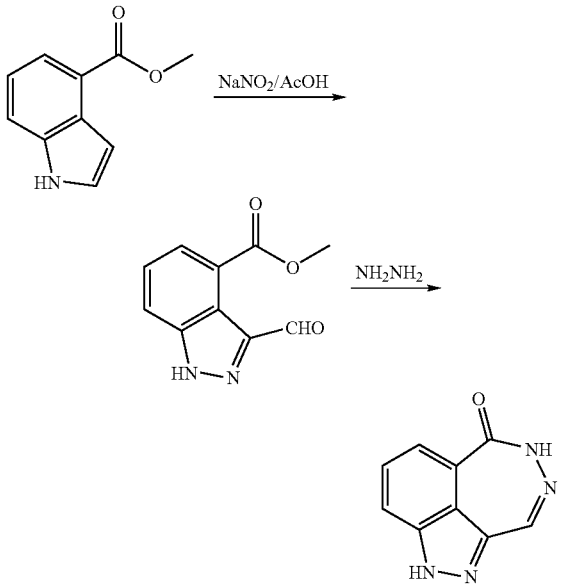

2,7-Dihydro-1,2,7,8-tetroaza-benzo(cd)azulen-6-one

Scheme above illustrates schematically the preparation of desired PARP inhibitor 2,7-dihydro-1,2,7,8-tetraaza-benzo

[cd]azulen-6-one starting from the commercially available indole-4-carboxylic acid methyl ester.

3-Formyl-1H-indazole-4-carboxylic acid methyl ester: Methyl indole-4-carboxylate (4.0 g, 22.85 mmol) was suspended in acetic acid (60 mL). The mixture was cooled down to 10 degrees Celsius. It was stirred and added sodium nitrite (3.2 g, 45.71 mmol). The reaction was slowly promoted to rt for 1 h. After this period, the reaction solvent was evaporated to dryness. It was washed with water (300 mL) and extracted with EtOAc (3×150 mL). The organic layer was washed with brine, dried in $MgSO_4$, and concentrated. The crude mixture was purified by silica gel column eluted with 40% EtOAc in Hexane to give the desired indole-3-carboxaldehyde-4-methyl ester ($R_f$=0.4, 40% EtOAc in Hex), (0.40 g, white solid). $^1$H NMR (d-6 DMSO) d 14.50 (bs, 1H), 10.33 (s, 1H), 7.94 (d, 1H, J=8.39 Hz), 7.68 (m, 1H), 7.58 (t, 1H, J=7.25 Hz), 3.87 (s, 3H).

2,7-Dihydro-1,2,7,8-tetraaza-benzo[cd]azulen-6-one: 3-Formyl-1H-indazole-4-carboxylic acid methyl ester (0.10 g, 0.53 mmol) was suspended in EtOH (6 mL). The mixture was added 5 drops of hydrazine. It was stirred and refluxed for 5 h. The product was forming as it precipitated in the hot solution. The reaction was cooled down to room temperature. The product was collected by vacuum filtration with no further purification (0.025 g, white solid). $^1$H NMR (d-6 DMSO) d 13.4 (bs, 1H), 11.01 (s, 1H), 7.87 (s, 1H), 7.70 (d, 1H, J=8.20 Hz), 7.67 (d, 1H, J=7.06 Hz), 7.54 (t, 1H, J=8.20 Hz). Anal. $C_9H_6N_4O_1$-1 $H_2O$.

Other manners, variations or sequences of preparing the compounds of the present invention will be readily apparent to those of ordinary skill in the art.

The compounds of the present invention may be useful in the free base form, in the form of base salts where possible, and in the form of addition salts, as well as in the free acid form. All these forms are within the scope of this invention. In practice, use of the salt form amounts to use of the base form. Pharmaceutically acceptable salts within the scope of this invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfonate, ethanesulfonate, benzenesulfonate, p-toluenesulfonate, and the like respectively, or those derived from bases such as suitable organic and inorganic bases. Examples of pharmaceutically acceptable base addition salts with compounds of the present invention include organic bases which are nontoxic and strong enough to form such salts. These organic bases and the use thereof are readily understood by those skilled in the art. Merely for the purpose of illustration, such organic bases may include mono-, di-, and trialkylamines, such as methylamine, diethylamine and triethylamine; mono-, di-, or trihydroxyalkylamines such as mono-, di-, and triethanolamine; amino acids such as arginine, and lysine; guanidine; N-methylglucosamine; N-methylgiucamine; L-glutamine; N-methylpiperazine; morpholine; ethylenedianane; N-benzylphenethylamine; tris(hydroxymethyl) antinoethane; and the like.

The acid addition salts of the basic compounds may be prepared by dissolving the free base of the compounds of the present invention in aqueous or aqueous alcohol solution or other suitable solvents containing the appropriate acid or base and isolating the salt by evaporating the solution, or by reacting the free base of a compound of the present invention with an acid as well as reacting a compound of the present invention having an acid group thereon with a base such that the reactions are in an organic solvent, in which case the salt separates directly or can be obtained by concentration of the solution.

The compounds of this invention contain one or more asymmetric carbon atoms. Therefore, the invention includes the individual stereoisomers and mixtures thereof as well as the racemic compounds. The individual isomers may be prepared or isolated by methods known in the art.

The compounds of the invention exhibit pharmacological activity and are, therefore, useful as pharmaceuticals. In particular the compounds exhibit central nervous and cardiac vesicular system activity.

Other variations and modifications of this invention using the synthetic pathways described above will be obvious to those of ordinary skill in the art.

Methods of Using the Compounds of the Invention

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; and can radiosensitize cells. Generally, inhibition of PARP activity spares the cells from energy loss, preventing, in the case of neural cells, irreversible depolarization of the neurons, and thus, provides neuroprotection While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, immune senescence, inflammation, gout, inflammatory bowel disorders (such as colitis and Crohn's disease), muscular dystrophy, osteoarhritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another preferred embodiment is when the reperfusion injury is a vascular stroke. Yet another preferred embodiment is when the peripheral neuropathy is caused by Guillain-Barre syndrome. Still another preferred embodiment is when the demyelinating disease and neurological disorder relates to neurodegeneration. Another preferred embodiment is when the reperfusion injury is a vascular stroke. Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

Yet another preferred embodiment is a method of treating, preventing or inhibiting a cardiovascular disease in an animal, such as angina pectoris, myocardial infarction, cardiovascular ischemia, and cardiovascular tissue damage related to PARP activation, by administering to said animal an effective amount of the compounds of the present invention.

The present invention also contemplates the use of compounds of formulas I, I-1, I-2, I-3a, I-3b, I-3c, I-3d, I-3e, I-4, II-5, II-6, I-7a, I-7b, I-8, II-9, II-10, I-11 or I-12 for inhibiting PARP activity, for treating, preventing or inhibiting tissue damage resulting from cell damage or death due to necrosis or apoptosis, for treating, preventing or inhibiting a neurological disorder in an animal.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another preferred embodiment is when the reperfusion injury is a vascular stroke. Yet another preferred embodiment is when the peripheral neuropathy is caused by Guillain-Barre syndrome. Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

The present invention also contemplates the use of compounds of formula I, I-1, I-2, I-3a, I-3b, I-3c, I-3d, I-3e, I-4, II-5, II-6, II-9, II-10, I-7a, I-7b, I-11 or I-12, or I-8 in the preparation of a medicament for the treatment of any of the diseases and disorders in an animal described herein.

In a particular embodiment, the disease or disorder is a neurological disorder.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another preferred embodiment is when the reperfusion injury is a vascular stroke. Yet another preferred embodiment is when the peripheral neuropathy is caused by Guillain-Barre syndrome.

Still another preferred embodiment is when the demyelinating diseases is multiple sclerosis. Another preferred embodiment is when the neurological disorder relating to neurodegeneration is selected from the group consisting of Alzheimer's Disease, Parkinson's Disease, and amyotrophic lateral sclerosis.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

As used herein, the term "neural tissue damage resulting from ischemia and reperfusion injury" includes neurotoxicity, such as seen in vascular stroke and global and focal ischemia. As used herein, the term "neurodegenerative diseases," includes Alzheimer's disease, Parkinson's disease and Huntington's disease.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

The term "radiosensitizer", as used herein, is defined as a molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^{0}$ meters. Preferred embodiments of the present invention employ the electromagnetic radiation of: gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), or microwave radiation (1 mm to 30 cm).

Compositions and Methods for Effecting Neuronal Activity

Preferably, the compounds of the invention inhibit PARP activity and, thus, are believed to be useful for treating neural tissue damage, particularly damage resulting from cerebral ischemia and reperfusion injury or neurodegenerative diseases in animals. The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

Further according to the invention, an effective therapeutic amount of the compounds and compositions described above are administered to animals to effect a neuronal activity, particularly one that is not mediated by NMDA neurotoxicity. Such neuronal activity may consist of stimulation of damaged neurons, promotion of neuronal regeneration, prevention of neurodegeneration and treatment of a neurological disorder. Accordingly, the present invention further relates to a method of effecting a neuronal activity in an animal, comprising administering an effective amount of a compound of formula I, I-1, I-2, I-3a, I-3b, I-3c, I-3d, I-3e, I-4, II-5, II-6, II-9, II-10, I-7a, I-7b, I-8, I-11 or I-12 to said animal.

Examples of neurological disorders that are treatable by the method of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; Huntington's Disease and Parkinson's disease.

The method of the present invention is particularly useful for treating a neurological disorder selected from the group consisting of: peripheral neuropathy caused by physical injury or disease state; head trauma, such as traumatic brain injury; physical damage to the spinal cord; stroke associated with brain damage, such as vascular stroke associated with hypoxia and brain damage, focal cerebral ischemia, global cerebral ischemia, and cerebral reperfusion injury;. demyelinating diseases, such as multiple sclerosis; and neurological disorders related to neurodegeneration, such as Alzheimer's Diseases, Parkinson's Disease, Huntington's Disease and amyotrophic lateral sclerosis (ALS).

Treating Other PARP-Related Disorders

The compounds, compositions and methods of the present invention are particularly useful for treating or preventing tissue damage resulting from cell death or damage due to necrosis or apoptosis.

The compounds, compositions and methods of the invention can also be used to treat a cardiovascular disorder in an animal, by administering an effective amount of a compound of formula I, I-1, I-2, I-3a, I-3b, I-3c, I-3d, I-3e, I-4, II-5, II-6, II-9, II-10, I-7a, I-7b, I-8, I-11 or I-12 to the animal. As used herein, the term "cardiovascular disorders" refers to those disorders that can either cause ischemia or are caused by reperfusion of the heart. Examples include, but are not limited to, coronary artery disease, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to PARP activation.

For example, the methods of the invention are believed to be useful for treating cardiac tissue damage, particularly damage resulting from cardiac ischemia or caused by reperfusion injury in animals. The methods of the invention are particularly useful for treating cardiovascular disorders selected from the group consisting of: coronary artery diseases, such as atherosclerosis; angina pectoris; myocardial infarction; myocardial ischemia and cardiac arrest; cardiac bypass; and cardiogenic shock. The methods of the invention are particularly helpful in treating the acute forms of the above cardiovascular disorders.

Further, the methods of the invention can be used to treat tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize tumor cells Further still, the methods of the invention can be used to treat cancer and to radiosensitize tumor cells. The term "cancer" is interpreted broadly. The compounds of the present invention can be "anti-cancer agents", which term also encompasses "anti-tumor cell growth agents" and "anti-neoplastic agents". For example, the methods of the invention are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasma, uterine cancer, vaginal cancer, cancer of the vulva and Wilm's tumor.

The term "radiosensitizer", as used herein, is defined as a molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^{0}$ meters. Preferred embodiments of the present invention employ the electromagnetic radiation of: gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 nm), and microwave radiation (1 mm to 30 cm).

Radiosensitizers are known to increase the sensitivity of cancerous cells to the toxic effects of electromagnetic radiation. Several mechanisms for the mode of action of radiosensitizers have been suggested in the literature including: hypoxic cell radiosensitizers (e.g., 2-nitroimidazole compounds, and benzotriazine dioxide compounds) promote the reoxygenation of hypoxic tissue and/or catalyze the generation of damaging oxygen radicals; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, NPe6, tin etioporphyrin SnET2, pheoborbide-a, bacteriochiorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but are not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Pharmaceutical Compositions of the Invention

The present invention also relates to a pharmaceutical composition comprising (i) a therapeutically effective amount of a compound of formula I, I-1, I-2, I-3a, I-3b, I-3c, I-3d, I-3e, I-4, II-5, II-6, II-9, II-10, I-7a, I-7b, I-8, I-11 or I-12 and (ii) a pharmaceutically acceptable carrier.

The above discussion relating to the preferred embodiments' utility and administration of the compounds of the present invention also applies to the pharmaceutical composition of the present invention.

The term "pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener.

For these purposes, the composition of the invention may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrastemal, and intracranial injection or infusion techniques.

When administered parenterally, the composition will normally be in a unit dosage, sterile injectable form (solution, suspension or emulsion ) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent surface active, or dispersing agent Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant, or externally applied patch, suitable for providing efficacious concentrations of the PARP inhibitors over a prolonged period of time without the need for frequent re-doing. Such controlled release films are well known to the art. Particularly preferred are transdermal delivery systems. Other examples of polymers commonly employed for this purpose that may be used in the present invention include nondegradable ethylene-vinyl acetate copolymer as degradable lactic acid-glycolic acid copolymers which may be used externally or internally. Certain hydrogels such as poly(hydroxyethylmethacrylate) or poly (vinylalcohol) also may be useful, but for shorter release cycles than the other polymer release systems, such as those mentioned above.

It is preferred embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be eliminated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The PARP inhibitors are used in the composition in amounts that are therapeutically effective. The compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances. The compositions are prepared according to conventional mixing, granulating, or coating methods, and contain about 0.1 to 75% by weight, preferably about 1 to 50% by weight, of the active ingredient.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

Doses of the compounds preferably include pharmaceutical dosage units comprising an efficacious quantity of active compound. By an efficacious quantity is meant a quantity sufficient to inhibit PARP and derive its beneficial effects through administration of one or more of the pharmaceutical dosage units. Preferably, the dose is sufficient to prevent or reduce the effects of vascular stroke or other neurodegenerative diseases.

For medical use, the amount required of the active ingredient to achieve a therapeutic effect will vary with the particular compound, the route of administration, the mammal under treatment, and the particular disorder or disease being treated. A suitable systemic dose of a compound of the present invention or a pharmacologically acceptable salt thereof for a mammal suffering from, or likely to suffer from, any of condition as described hereinbefore is in the range of about 0.1 mg/kg to about 100 mg/kg of the active ingredient compound, the most preferred dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administration, parenterally or orally, as considered appropriate. While it is possible for an active ingredient to be administered alone, it is preferable to present it as a formulation.

When preparing a dosage form incorporating the compositions of the invention the compounds may also be blended with conventional excipients such as binders, including gelatin, pregelatinized starch and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D. & C. dyes and lakes; flavorants; and sweeteners.

The present invention relates to the use of a compound of formulas I, I-1, I-2, I-3a, I-3b, I-3c, I-3d, I-3e, I-4, II-5, II-6, II-9, II-10, I-7a, I-7b, I-8, I-11 or I-12 in the preparation of a medicament for the treatment of any disease or disorder in an animal described herein.

PARP Assays $IC_{50}$

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 3.0 μg/ml of DNase I activated herring sperm DNA (Sigma, Mo.), 30 micromolar [3H]nicotinamide adenine dinucleotide (62.5 mci/mmole), 15 micrograms/ml PARP enzyme, and various concentrations of the compounds to be tested. The reaction is initiated by adding enzyme and incubating the mixture at 25° C. After 2 minutes of incubation, the reaction is terminated by adding 500 microliters of ice cold 30% (w/v) trichloroacetic acid. The precipitate formed is transferred onto a glass fiber filter (Packard Unifilter-GF/C) and washed three times with 70% ethanol. After the filter is dried, the radioactivity is determined by scintillation counting. The compounds of this invention were found to have potent enzymatic activity in the range of a few nM to 20 mM in $IC_{50}$ in this inhibition assay.

Using the PARP assay described above, approximate $IC_{50}$ (μM) values were obtained as shown in the following Table III, which also include specific embodiments of the compounds of the present invention.

TABLE III

| STRUCTURE | $IC_{50}$ (μM) |
|---|---|
| 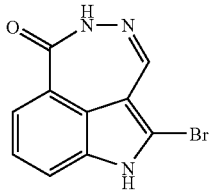 | 0.026 |

TABLE III-continued

| STRUCTURE | $IC_{50}$ (μM) |
|---|---|
| 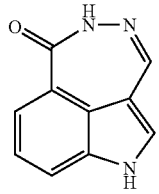 | 0.018 |
| 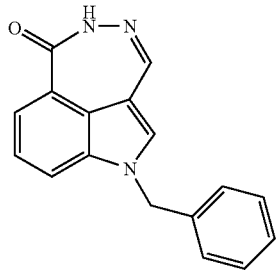 | 13 |
| 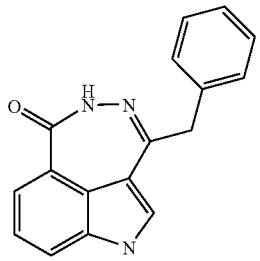 | 0.064 |
| 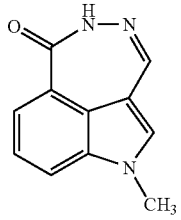 | 0.146 |
| 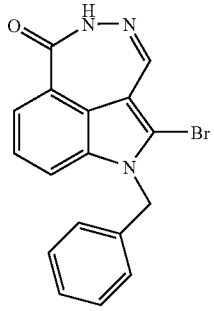 | 20 |
| 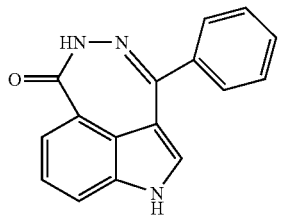 | 0.021 |

TABLE III-continued
| STRUCTURE | $IC_{50}$ (μM) |
|---|---|
| 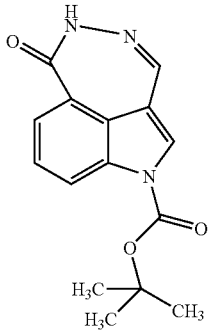 | 1.2 |
| 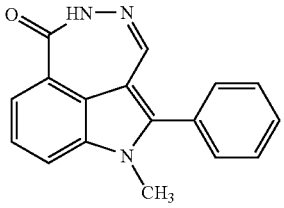 | 0.047 |
| 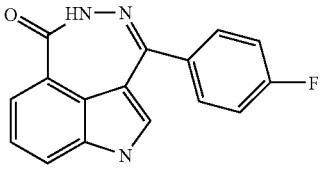 | 0.073 |
| 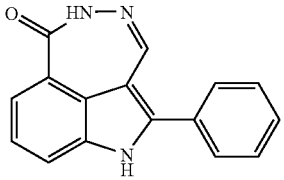 | 0.01 |
| 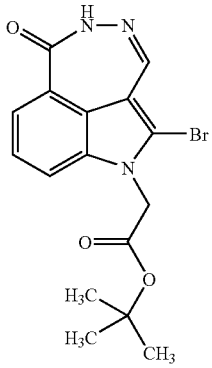 | 24.1 |
| 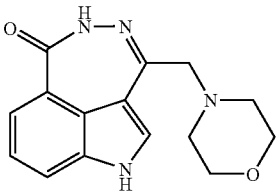 | 0.037 |
TABLE III-continued
| STRUCTURE | $IC_{50}$ (μM) |
|---|---|
| 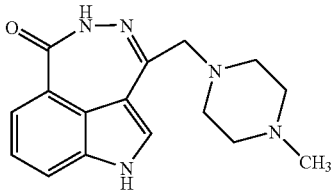 | 0.037 |
| 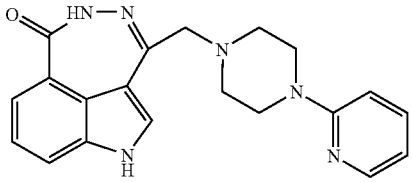 | 0.025 |
| 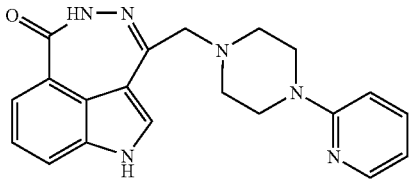 | 0.037 |
| 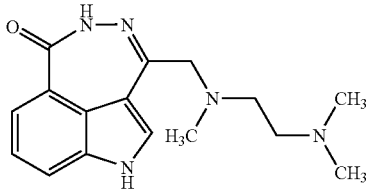 | 0.035 |
| 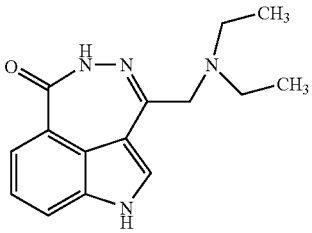 | 0.034 |
| 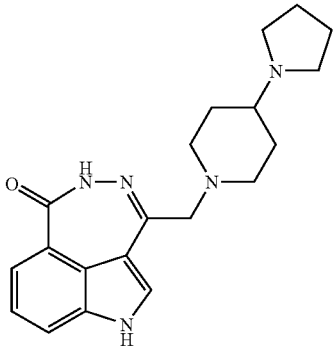 | 0.098 |

TABLE III-continued
| STRUCTURE | $IC_{50}$ (μM) |
|---|---|
| 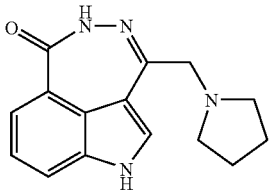 | 0.033 |
| 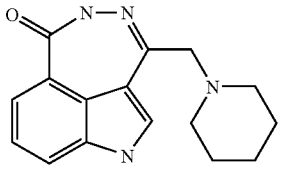 | 0.027 |
| 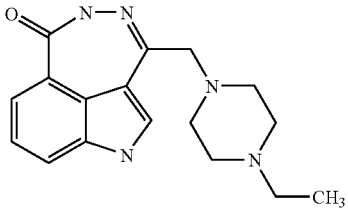 | 0.06 |
| 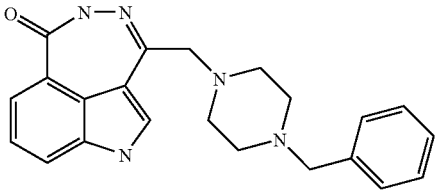 | 0.141 |
| 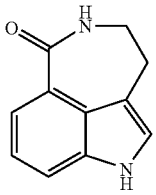 | 0.366 |
| 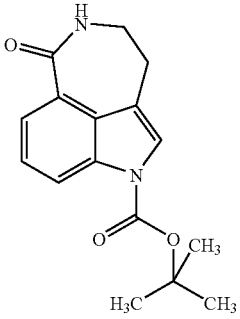 | 20 |
| 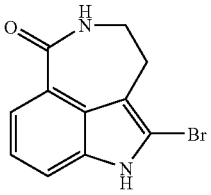 | 0.051 |
TABLE III-continued
| STRUCTURE | $IC_{50}$ (μM) |
|---|---|
| 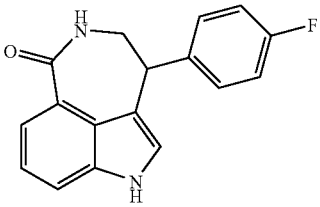 | 0.427 |
| 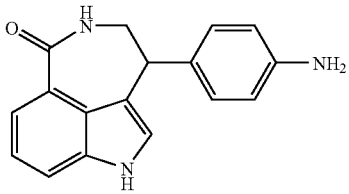 | 0.172 |
| 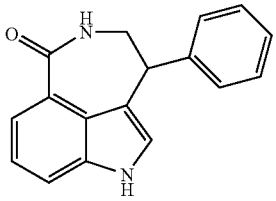 | 0.176 |
| 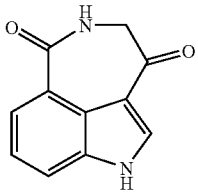 | 0.035 |
| 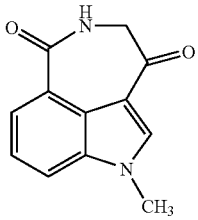 | 0.028 |
| 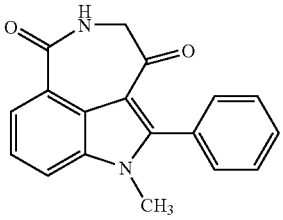 | 0.058 |
| 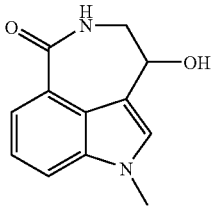 | 0.79 |

TABLE III-continued
| STRUCTURE | $IC_{50}$ (μM) |
|---|---|
| 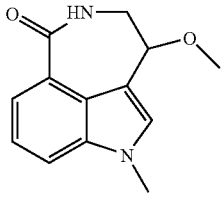 | 4.6 |
| 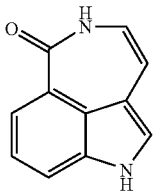 | 0.161 |
| 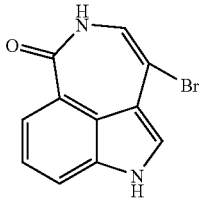 | 0.061 |
| 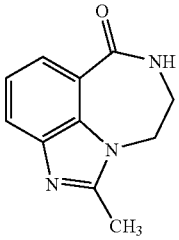 | 0.141 |
| 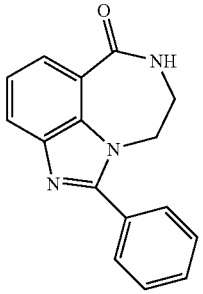 | 0.088 |
| 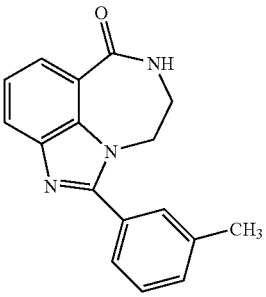 | 0.097 |
TABLE III-continued
| STRUCTURE | $IC_{50}$ (μM) |
|---|---|
| 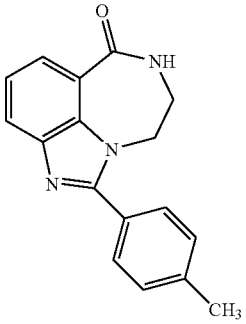 | 0.11 |
| 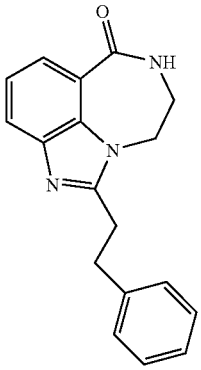 | 0.026 |
| 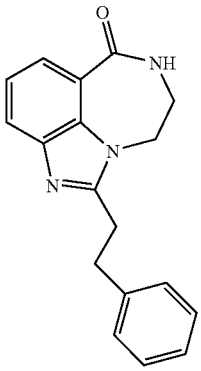 | 0.118 |
| 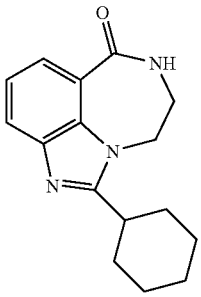 | 0.204 |

TABLE III-continued
| STRUCTURE | $IC_{50}$ (μM) |
|---|---|
| 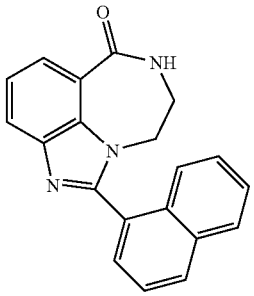 | 0.382 |
| 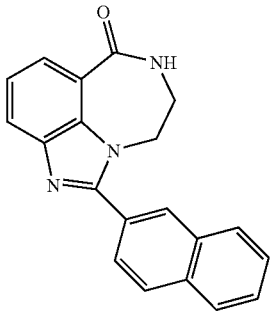 | 0.032 |
| 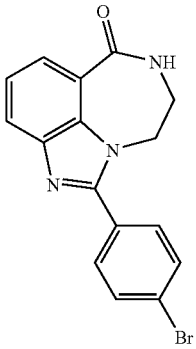 | 0.054 |
| 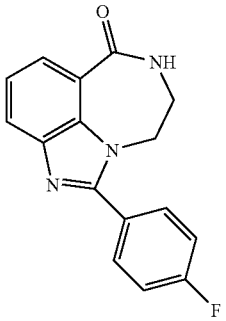 | 0.201 |
TABLE III-continued
| STRUCTURE | $IC_{50}$ (μM) |
|---|---|
| 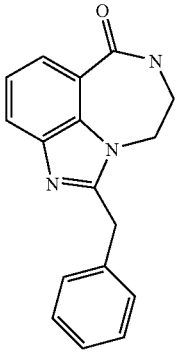 | 0.108 |
| 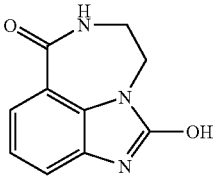 | 1.4 |
| 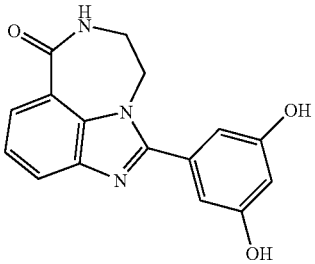 | 0.089 |
| 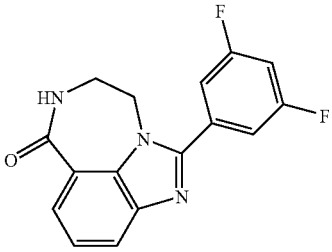 | 0.061 |
| 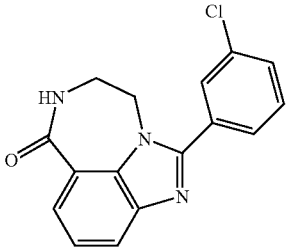 | 0.08 |

TABLE III-continued
| STRUCTURE | $IC_{50}$ (μM) |
|---|---|
| 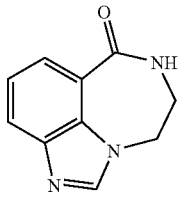 | 0.299 |
| 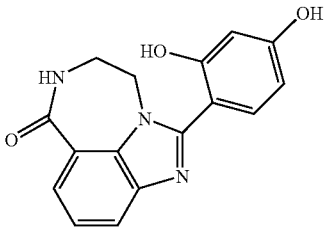 | 0.186 |
| 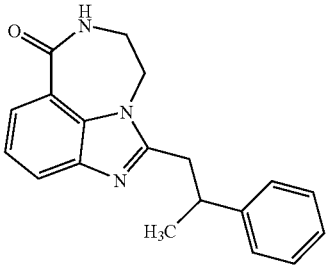 | 0.13 |
| 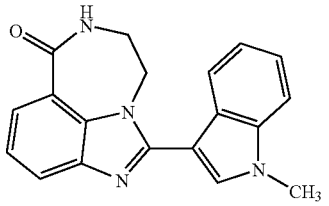 | 0.268 |
| 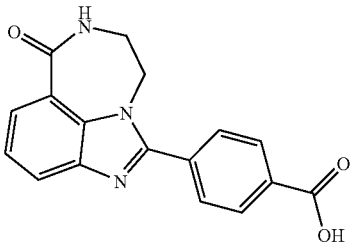 | 1.19 |
| 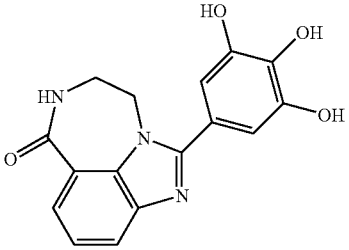 | 0.324 |
TABLE III-continued
| STRUCTURE | $IC_{50}$ (μM) |
|---|---|
| 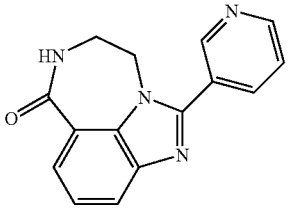 | 0.168 |
| 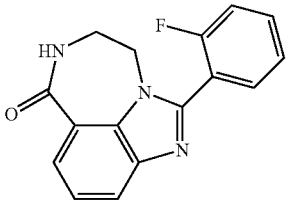 | 0.329 |
| 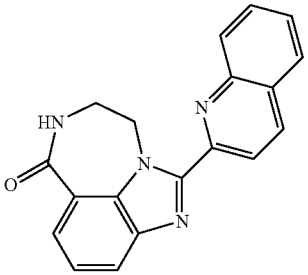 | 0.299 |
| 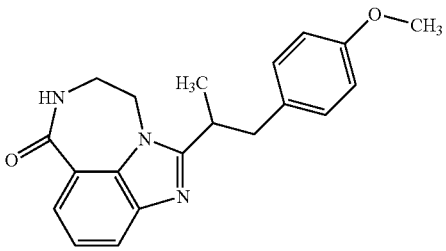 | 0.128 |
| 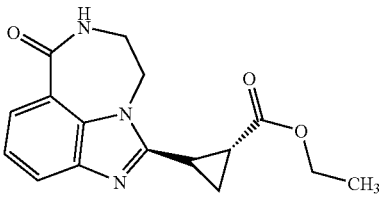 | 0.108 |
| 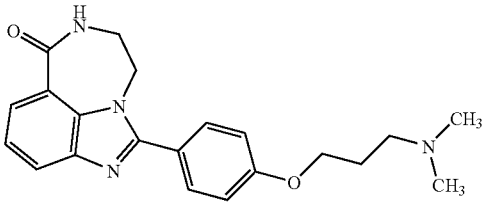 | 0.237 |

TABLE III-continued
| STRUCTURE | $IC_{50}$ (μM) |
|---|---|
| 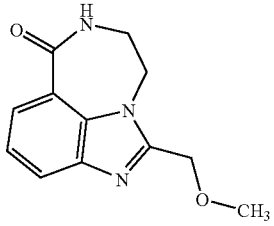 | 0.227 |
| 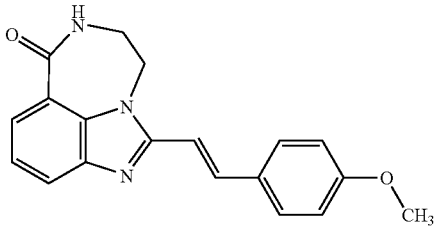 | 0.142 |
| 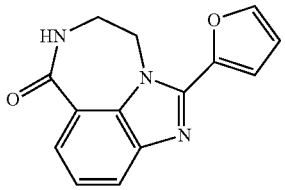 | 0.108 |
| 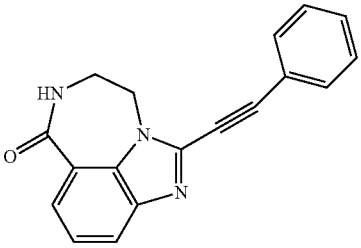 | 0.044 |
| 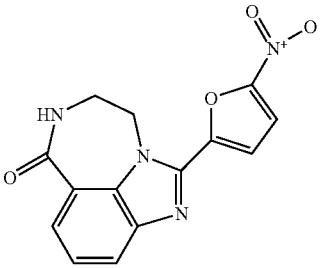 | 0.021 |
| 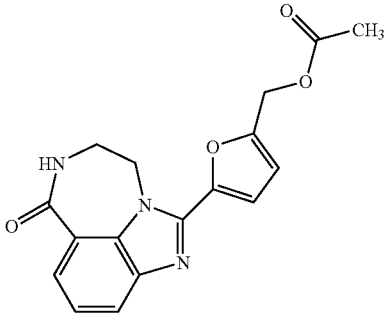 | 0.068 |
TABLE III-continued
| STRUCTURE | $IC_{50}$ (μM) |
|---|---|
| 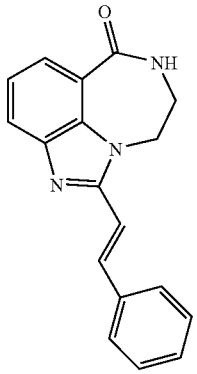 | 0.071 |
| 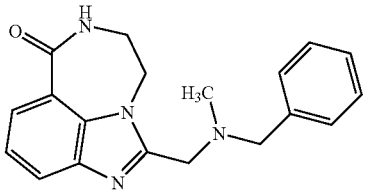 | 0.088 |
| 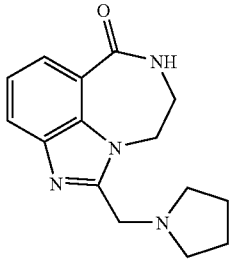 | 0.109 |
| 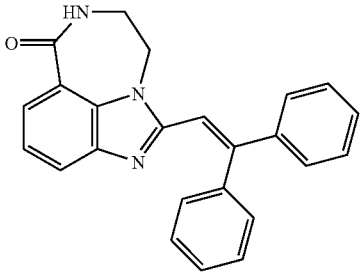 | 0.33 |
| 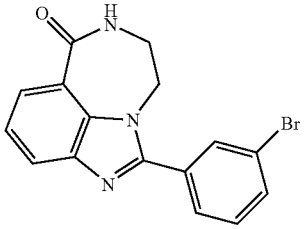 | 0.106 |

TABLE III-continued
| STRUCTURE | $IC_{50}$ (μM) |
|---|---|
| 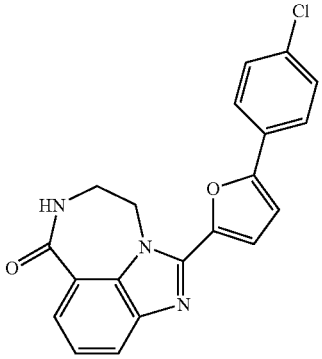 | 0.96 |
| 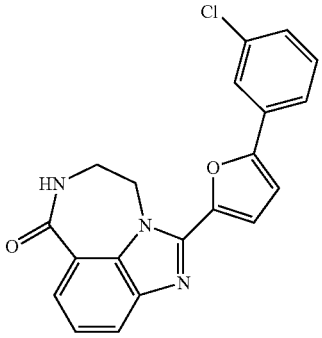 | 0.2 |
| 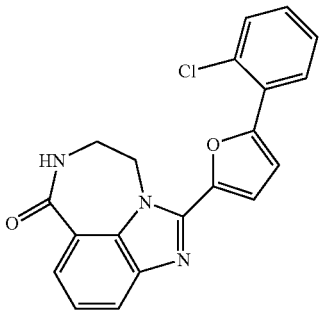 | 0.145 |
| 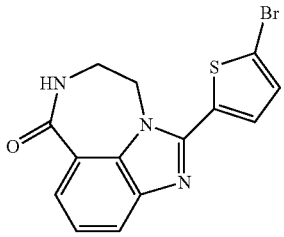 | 0.094 |
| 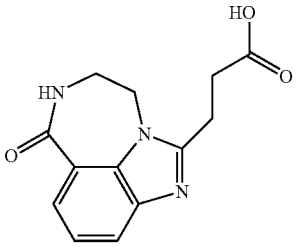 | 1.44 |
TABLE III-continued
| STRUCTURE | $IC_{50}$ (μM) |
|---|---|
| 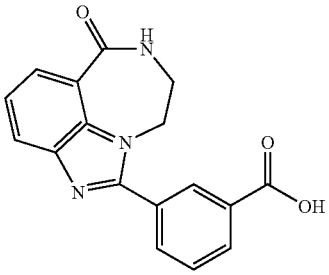 | 0.155 |
| 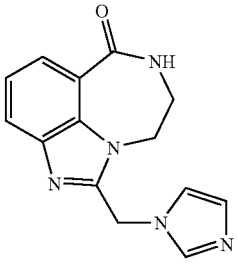 | 0.738 |
| 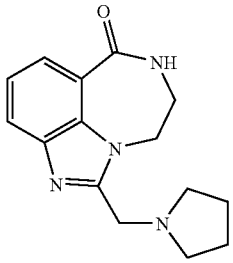 | 0.37 |
| 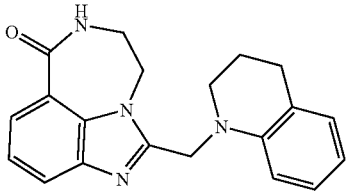 | 0.818 |
| 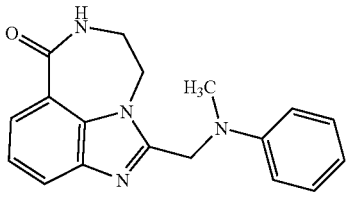 | 0.28 |
| 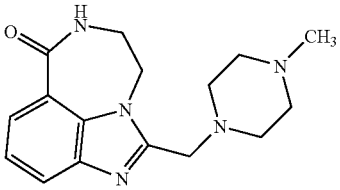 | 1.57 |

TABLE III-continued
| STRUCTURE | $IC_{50}$ (μM) |
|---|---|
| 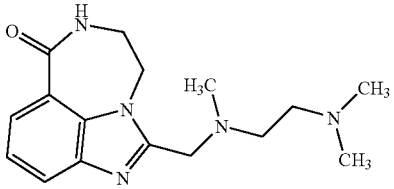 | 0.288 |
| 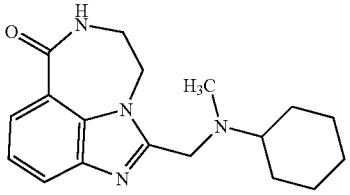 | 0.46 |
| 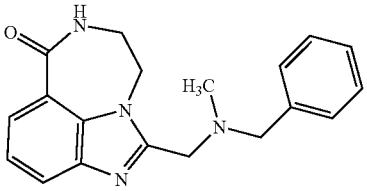 | 0.166 |
| 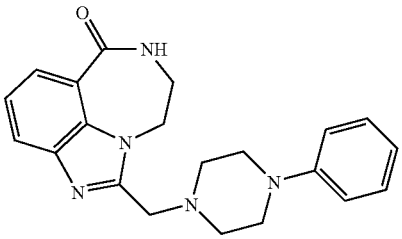 | 1.9 |
| 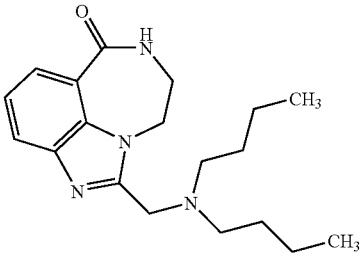 | 1.75 |
| 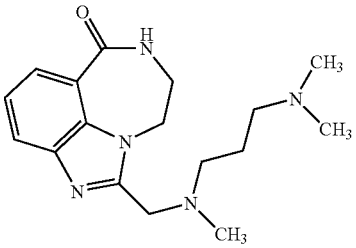 | 0.473 |
TABLE III-continued
| STRUCTURE | $IC_{50}$ (μM) |
|---|---|
| 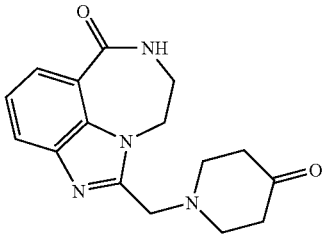 | 0.329 |
| 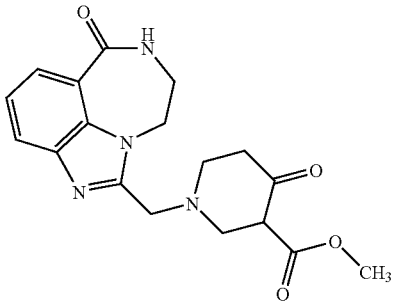 | 0.441 |
| 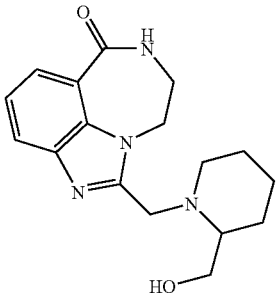 | 0.337 |
| 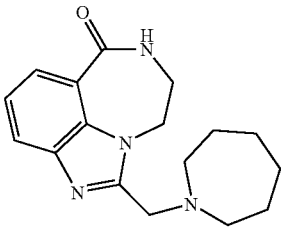 | 1 |
| 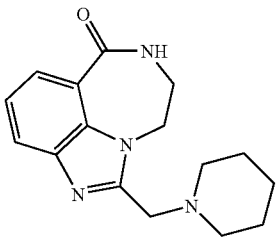 | 0.801 |

TABLE III-continued
| STRUCTURE | $IC_{50}$ (μM) |
|---|---|
| 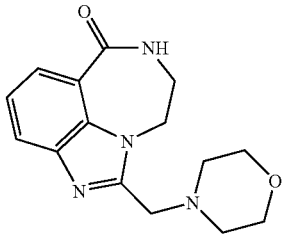 | 0.523 |
| 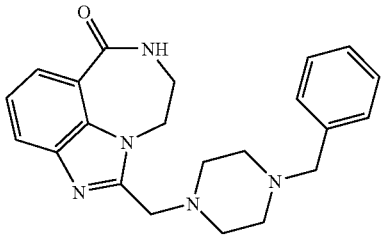 | 2.19 |
| 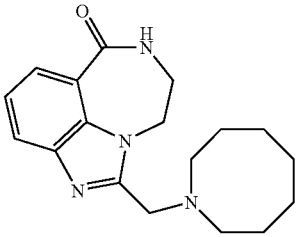 | 0.6 |
| 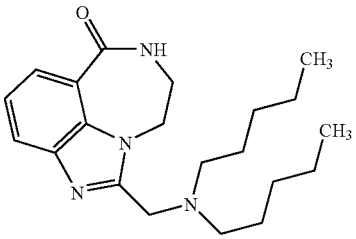 | 0.915 |
| 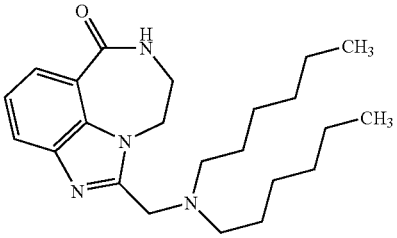 | 0.915 |
| 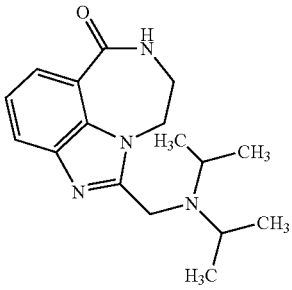 | 0.647 |
TABLE III-continued
| STRUCTURE | $IC_{50}$ (μM) |
|---|---|
| 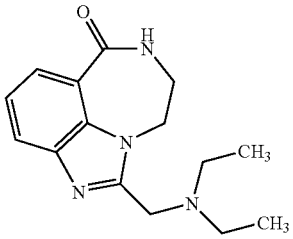 | 0.535 |
| 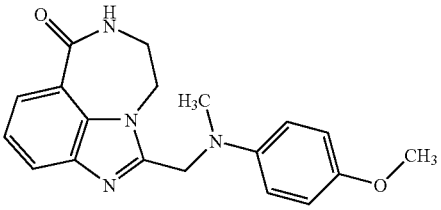 | 0.121 |
| 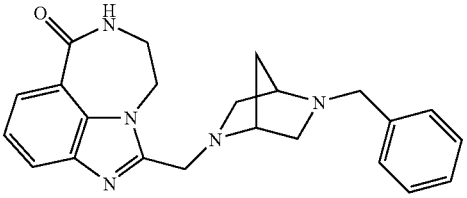 | 0.115 |
| 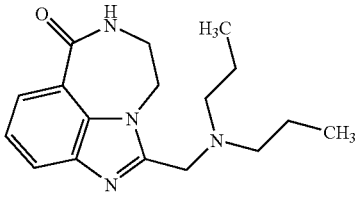 | 0.204 |
| 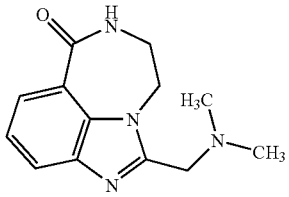 | 0.068 |
| 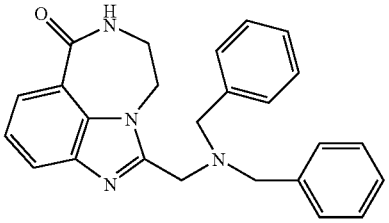 | 0.218 |
| 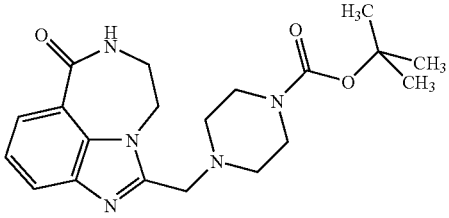 | 0.266 |

TABLE III-continued
| STRUCTURE | $IC_{50}$ (μM) |
|---|---|
| 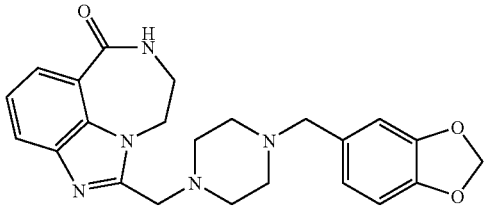 | 0.12 |
| 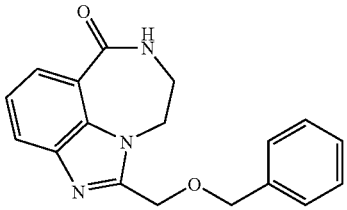 | 0.434 |
| 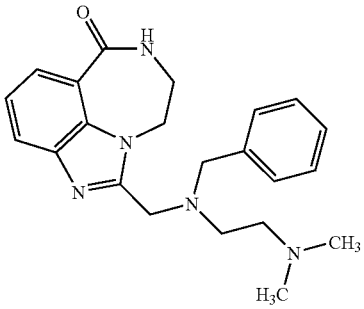 | 0.153 |
| 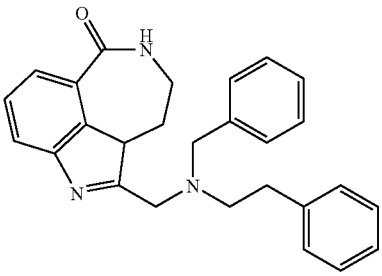 | 10.5 |
| 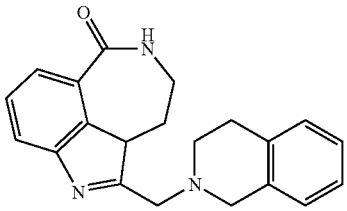 | 0.193 |
TABLE III-continued
| STRUCTURE | $IC_{50}$ (μM) |
|---|---|
| 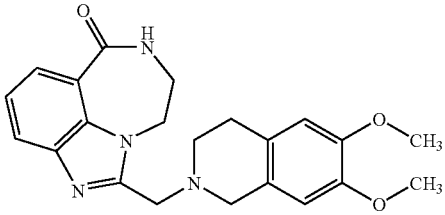 | 0.713 |
| 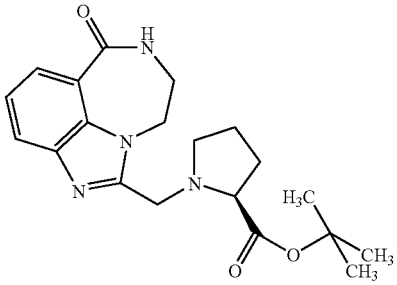 | 0.349 |
| 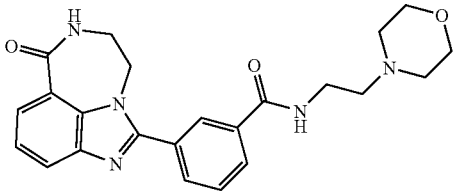 | 0.448 |
| 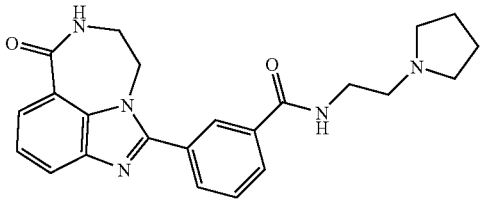 | 0.321 |
| 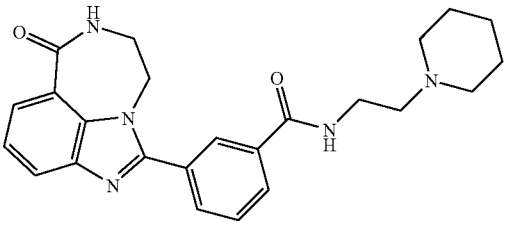 | 0.376 |

TABLE III-continued
| STRUCTURE | $IC_{50}$ (μM) |
|---|---|
| 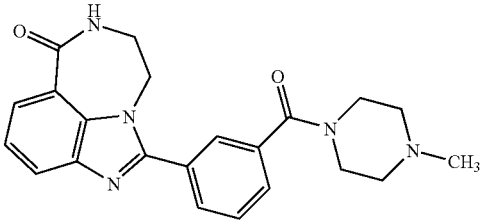 | 0.284 |
| 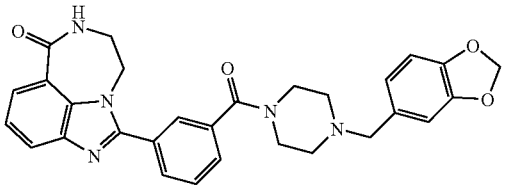 | 0.635 |
| 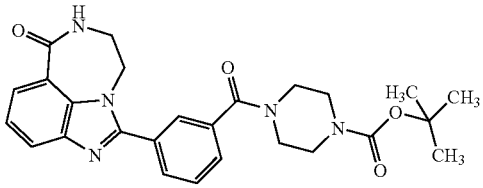 | 0.583 |
| 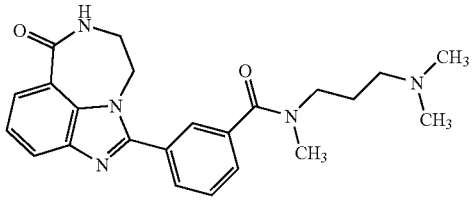 | 0.199 |
| 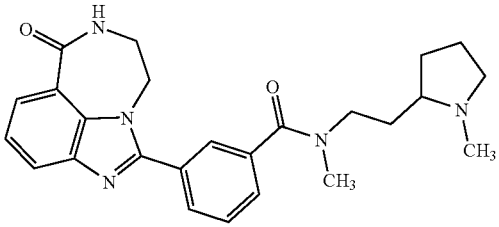 | 1.24 |
| 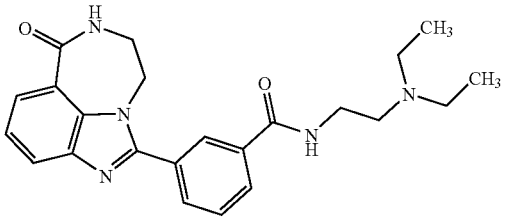 | 0.449 |
| 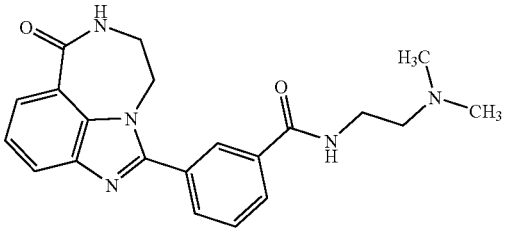 | 0.246 |
TABLE III-continued
| STRUCTURE | $IC_{50}$ (μM) |
|---|---|
| 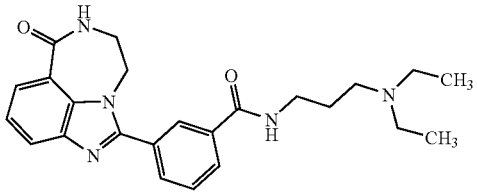 | 0.179 |
| 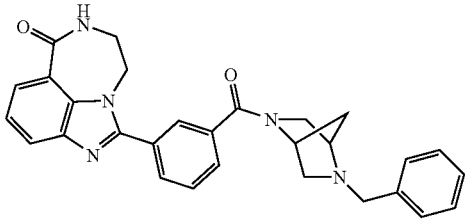 | 0.405 |
| 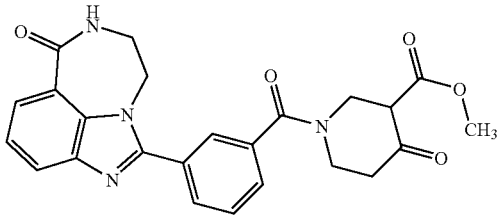 | 0.375 |
| 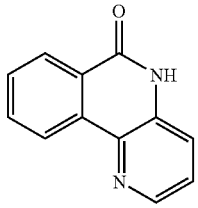 | 0.12 |
| 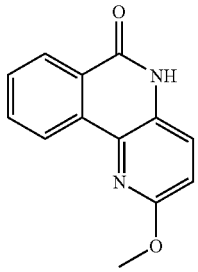 | 0.216 |
| 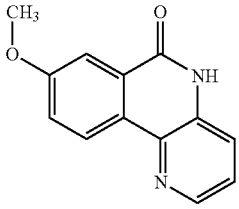 | 4.15 |

TABLE III-continued
| STRUCTURE | $IC_{50}$ (μM) |
|---|---|
| 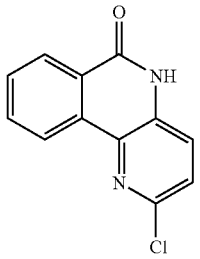 | 2.1 |
| 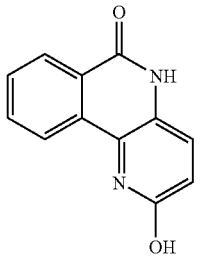 | 0.114 |
| 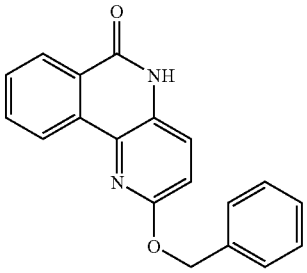 | 20 |
| 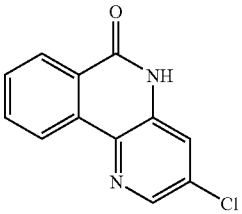 | 0.292 |
| 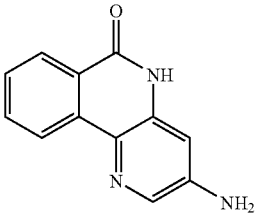 | 0.18 |
| 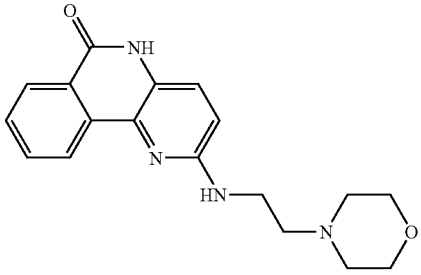 | 0.339 |
TABLE III-continued
| STRUCTURE | $IC_{50}$ (μM) |
|---|---|
| 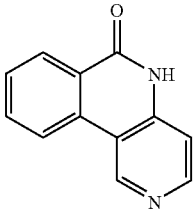 | 0.045 |
| 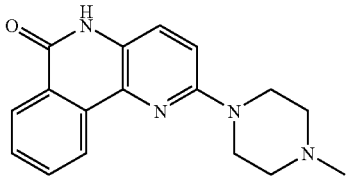 | 0.076 |
| 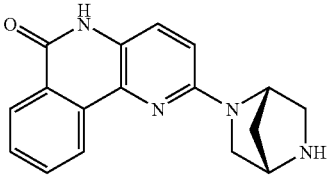 | 0.042 |
| 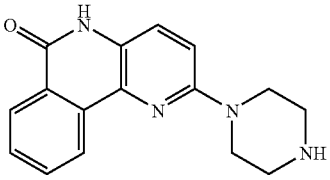 | 0.045 |
| 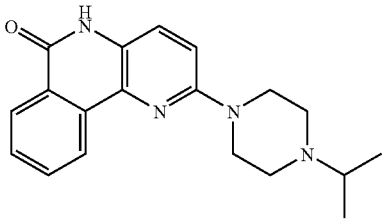 | 0.179 |
| 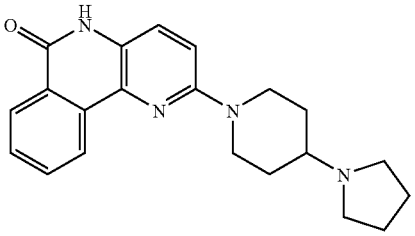 | 0.079 |
| 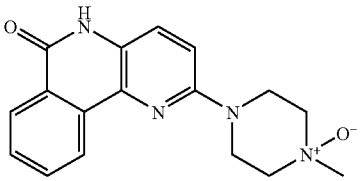 | 0.247 |

TABLE III-continued
| STRUCTURE | $IC_{50}$ (μM) |
|---|---|
| 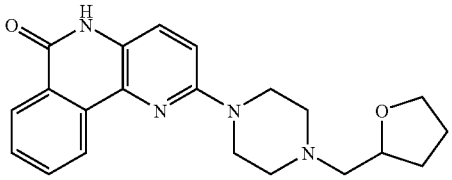 | 0.179 |
| 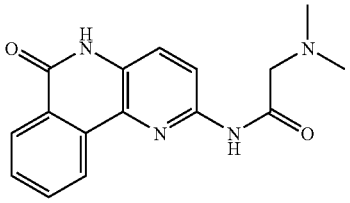 | 0.098 |
| 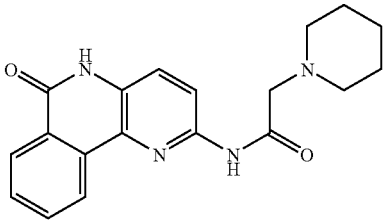 | 0.150 |
| 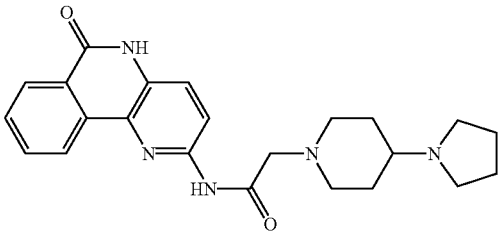 | 0.142 |
| 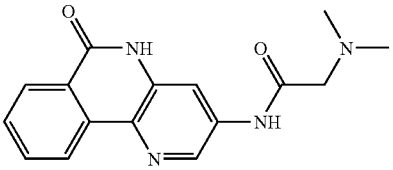 | 0.165 |
| 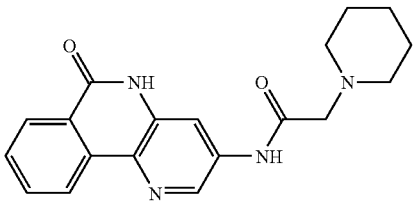 | 0.111 |
| 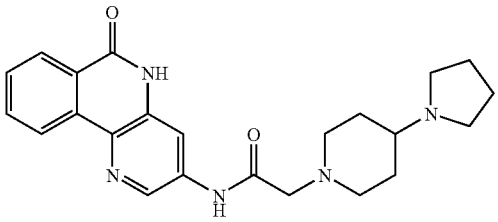 | 0.134 |
TABLE III-continued
| STRUCTURE | $IC_{50}$ (μM) |
|---|---|
| 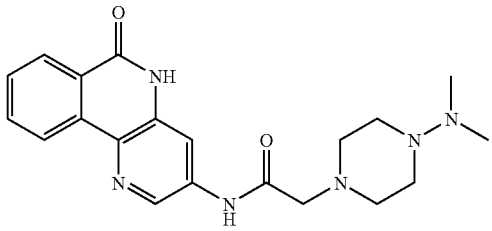 | 0.086 |
| 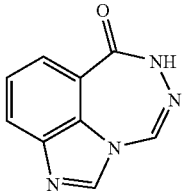 | 20 |
| 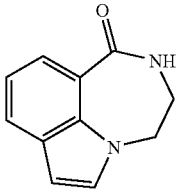 | 0.7 |
| 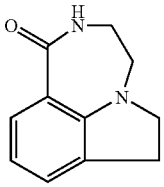 | 2.41 |
Further compounds, which are exemplified embodiments of the present invention, include the following:
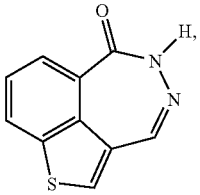
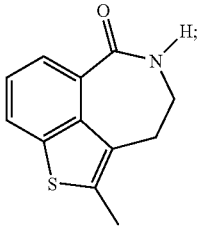
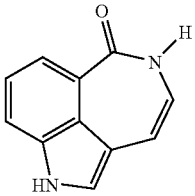
;
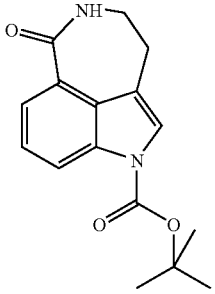
;

-continued
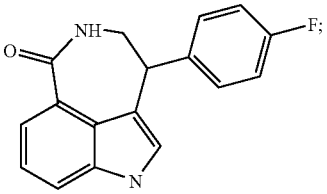
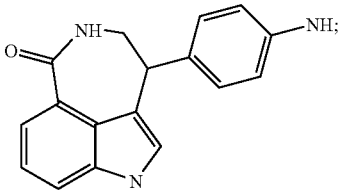
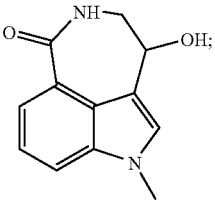
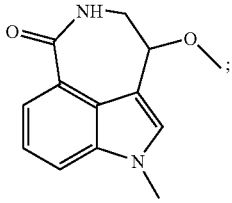
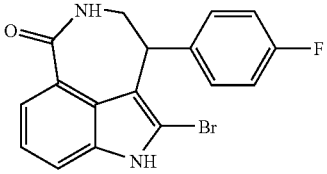
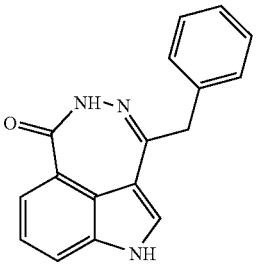
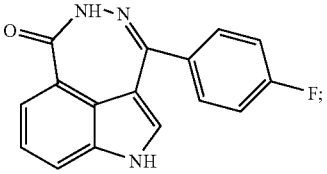
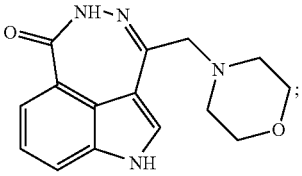
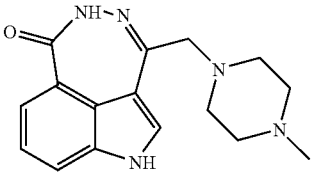
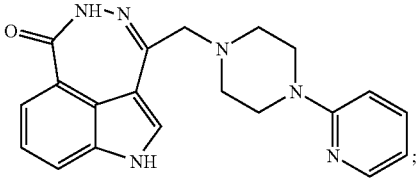
-continued
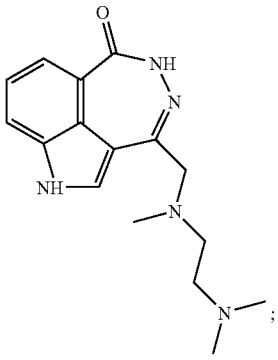
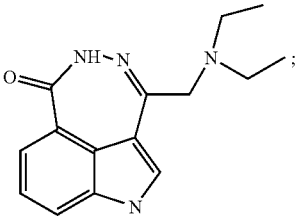
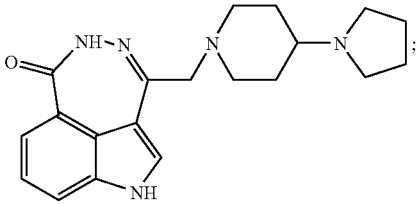
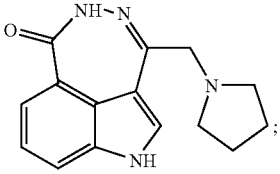
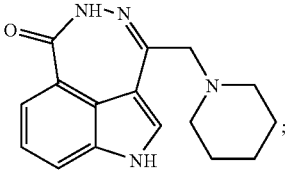
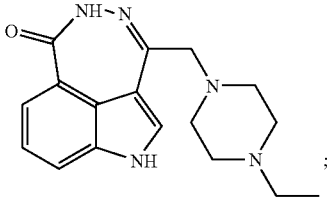

-continued
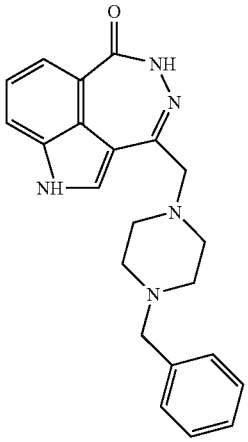
;
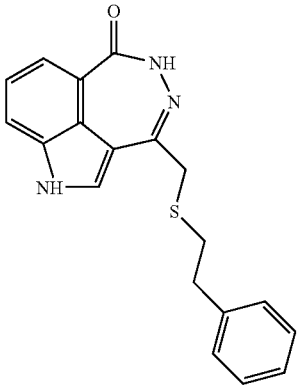
;
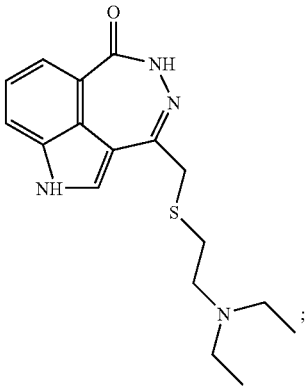
;
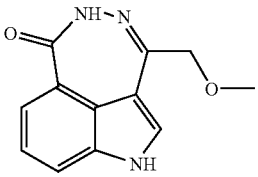
;
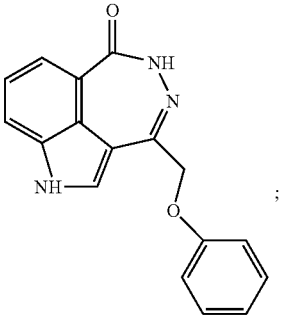
;
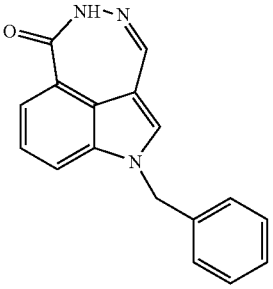
;
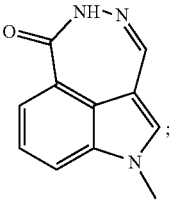
;
-continued
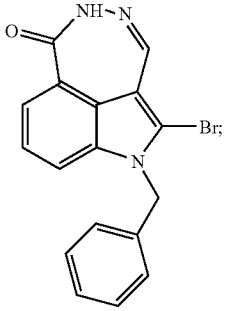
Br;
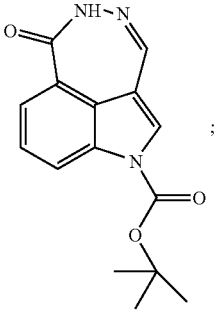
;
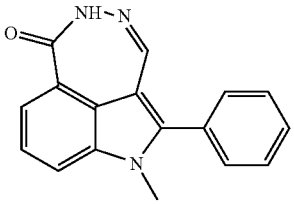
;
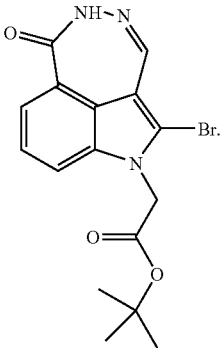
Br.
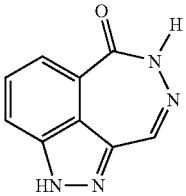
,
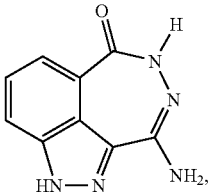
$NH_2$,
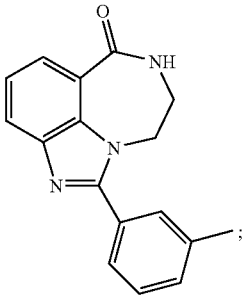
;
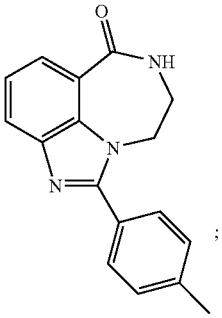
;

-continued
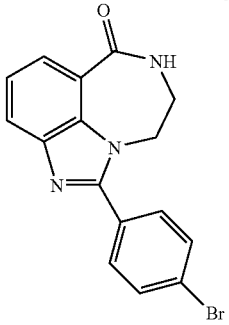
;
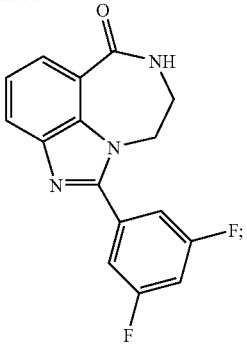
;
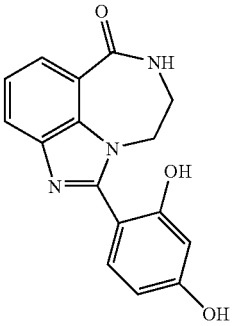
;
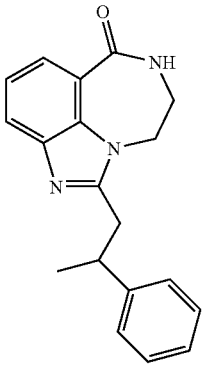
;
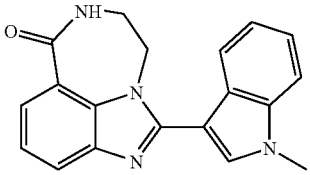
;
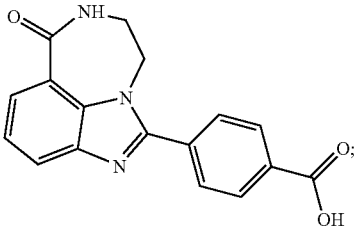
;
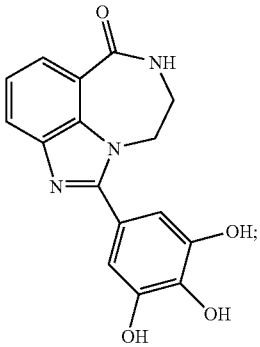
;
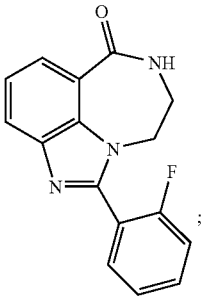
;
-continued
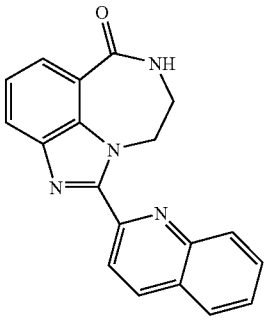
;
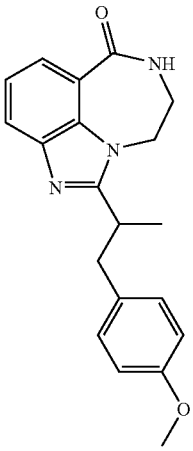
;
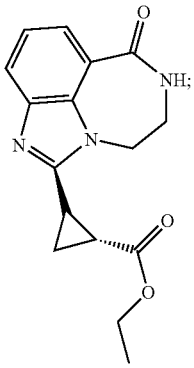
;
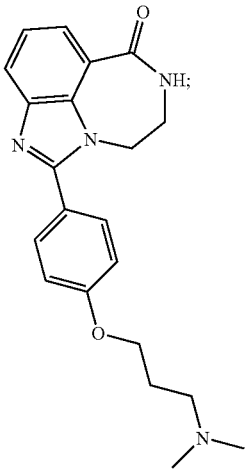
;
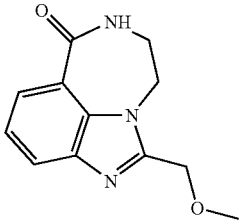
;
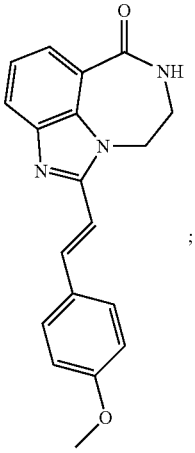
;

-continued
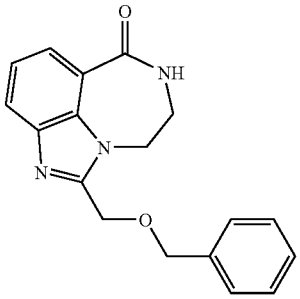
;
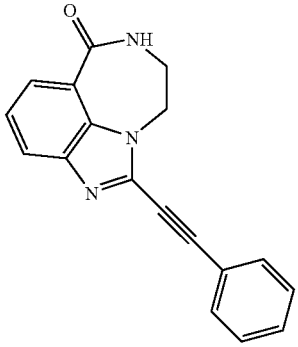
;
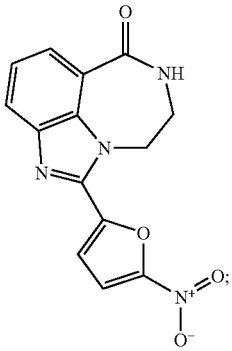
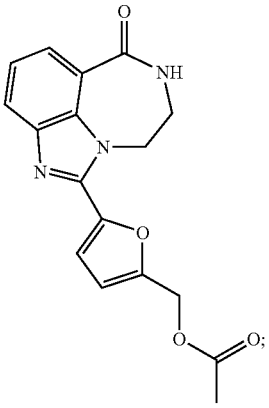
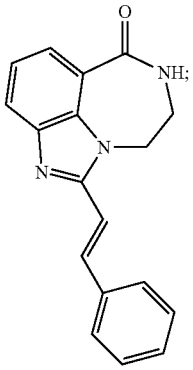
;
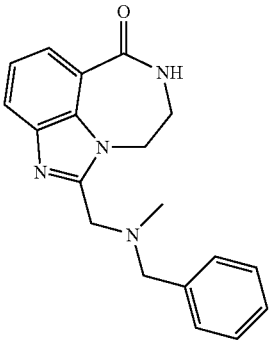
-continued
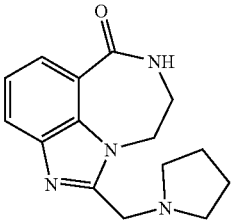
;
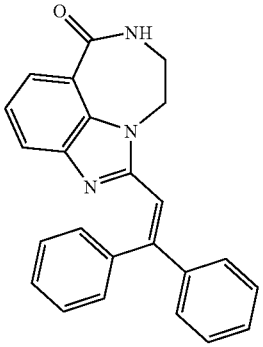
;
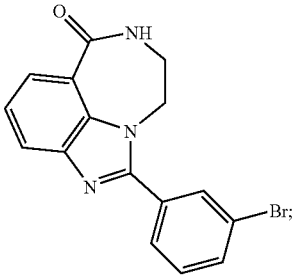
Br;
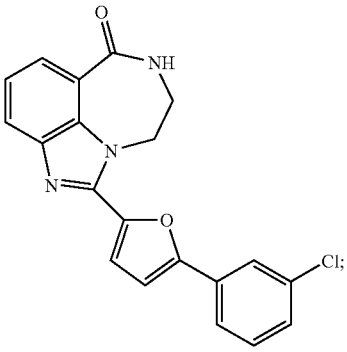
Cl;
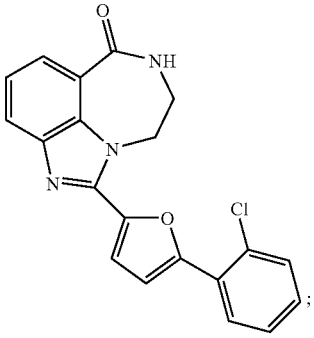
;

-continued
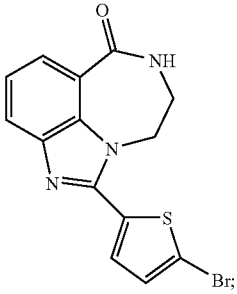
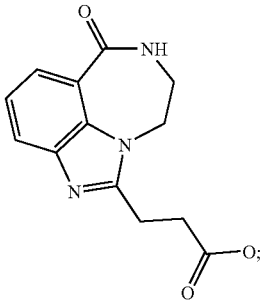
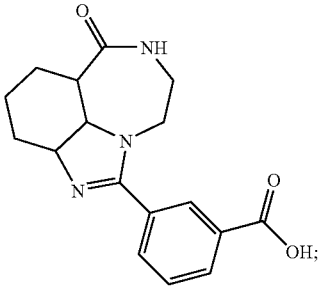
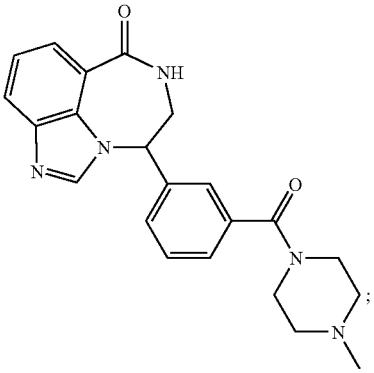
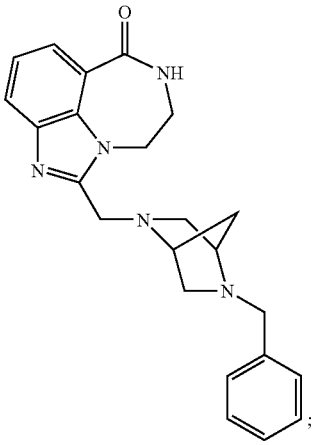
-continued
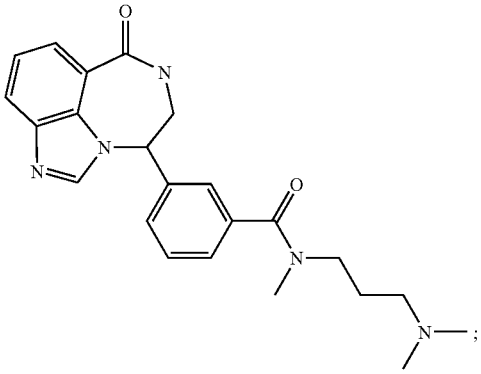
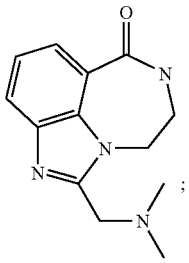
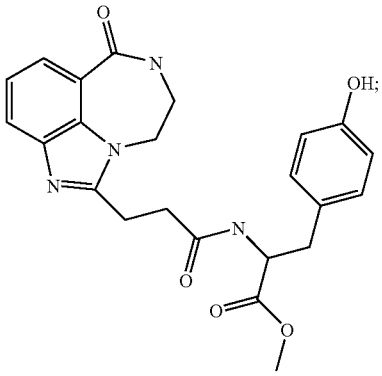
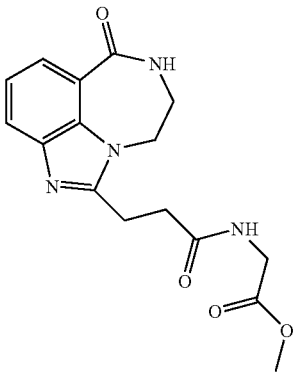
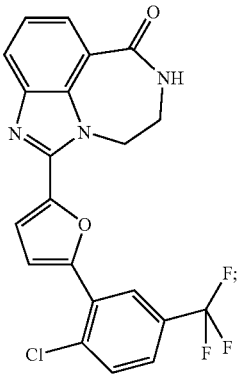

-continued
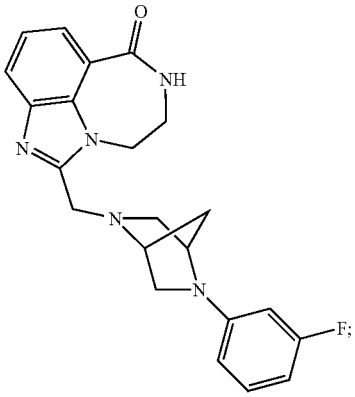
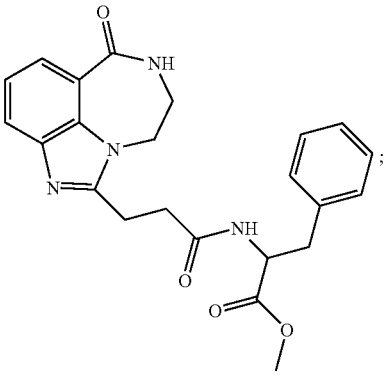
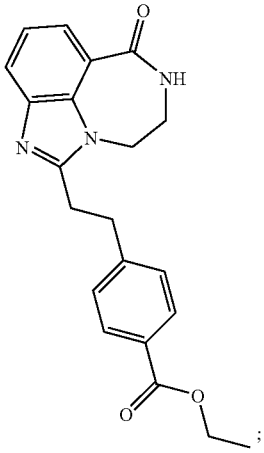
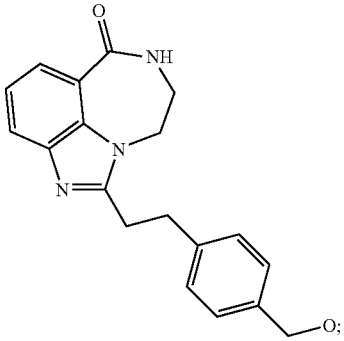
-continued
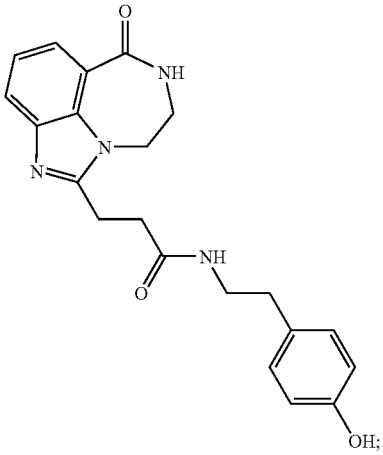
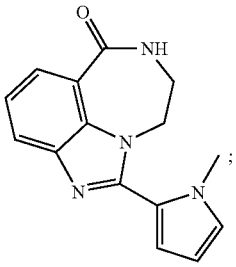
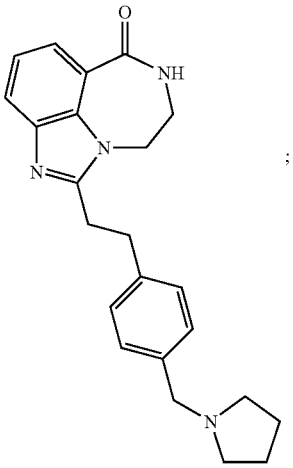
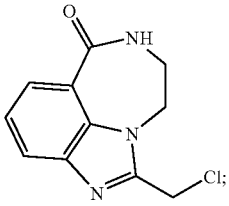
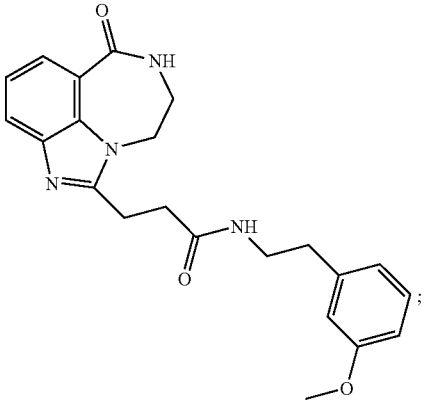

-continued
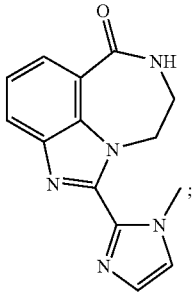
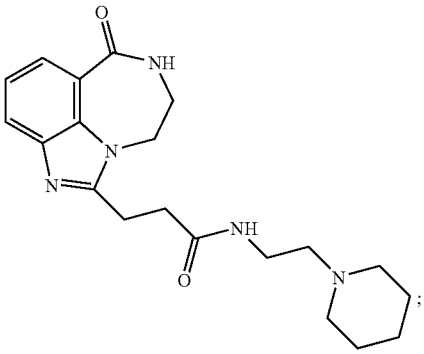
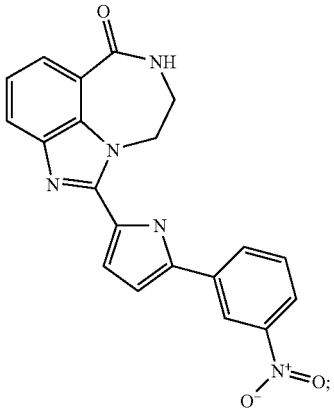
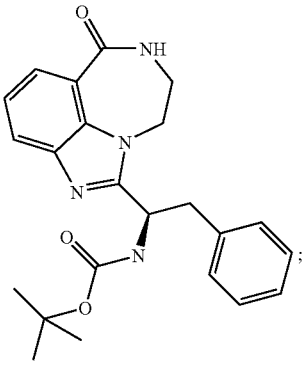
-continued
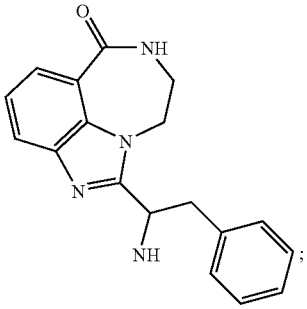
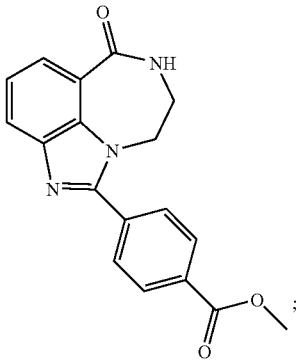
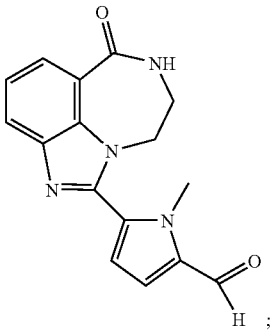
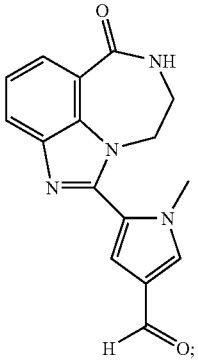

-continued
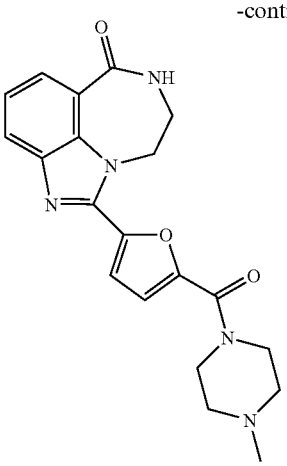
;
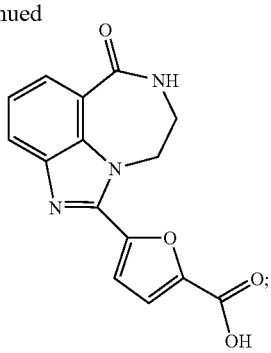
;
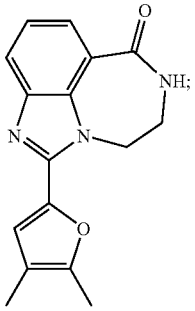
;
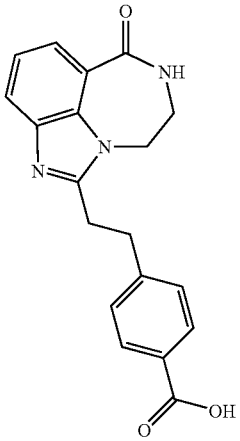
;
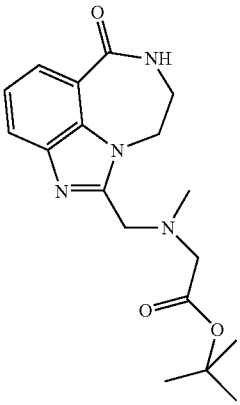
;
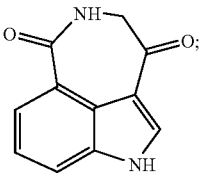
;
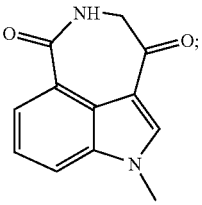
;
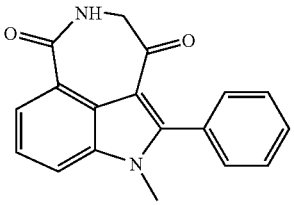
-continued
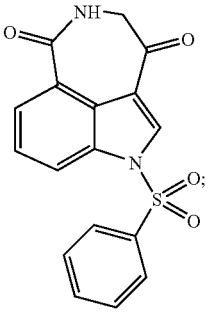
;
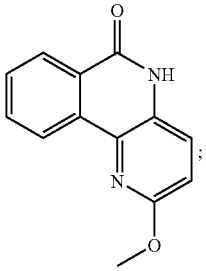
;
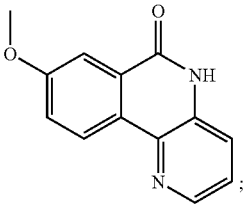
;
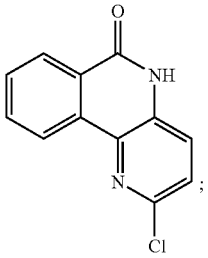
;
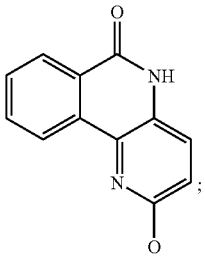
;
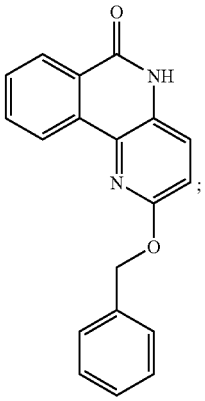
;
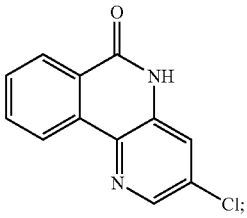
;
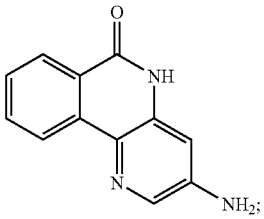
;
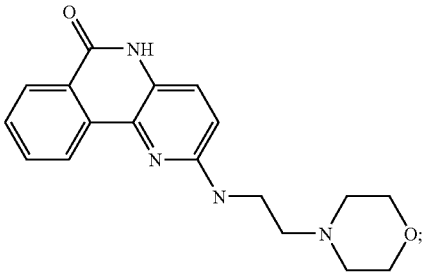
;

-continued
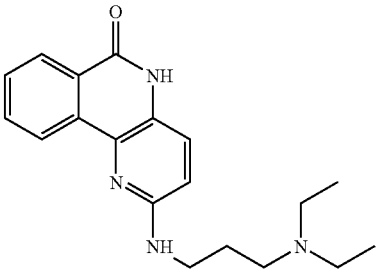
;
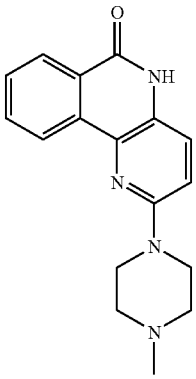
;
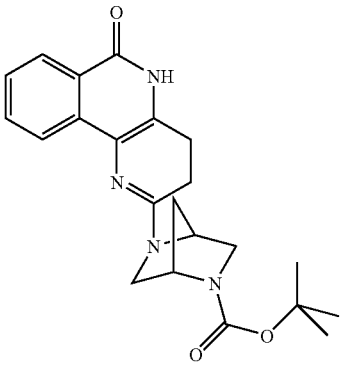
;
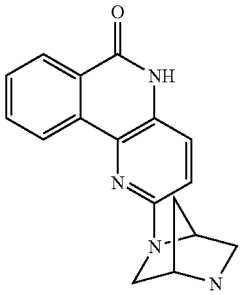
;
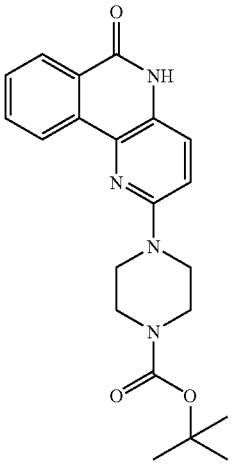
;
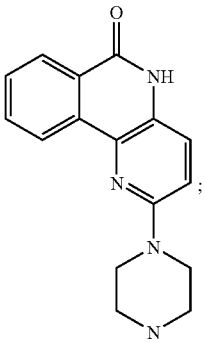
;
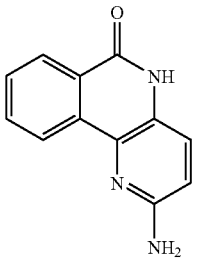
;
-continued
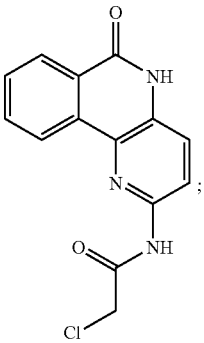
;
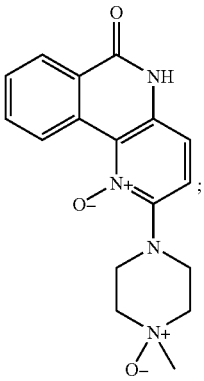
;
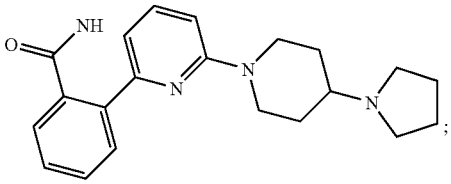
;
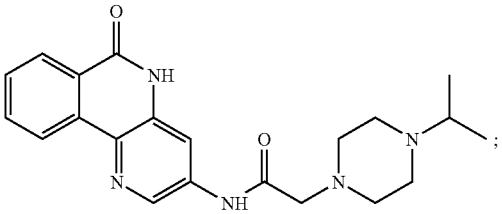
;
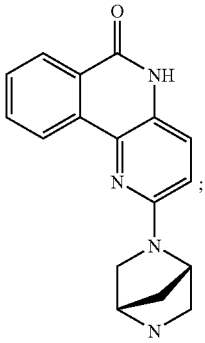
;
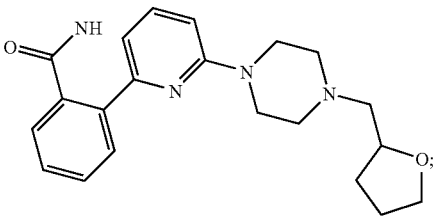
O;

-continued

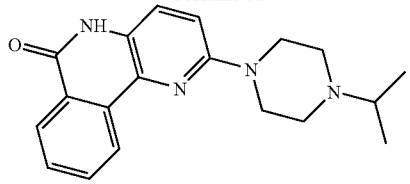

;

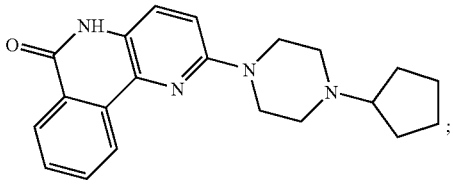

;

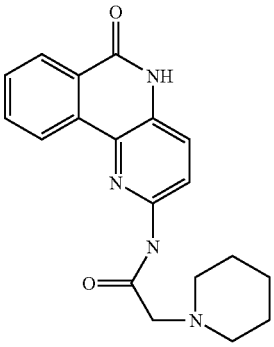

;

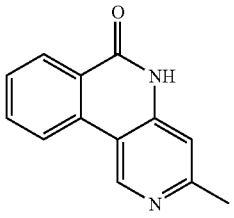

; and

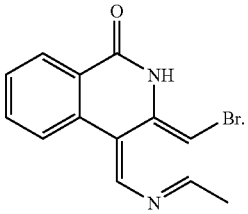

Focal Cerebral Ischemia

The following focal cerebral ischemia assay is useful for determining the PARP inhibiting effects of the compounds of the present invention. The following examples demonstrate that compounds related to those of the present invention are effective in inhibiting PARP activity.

Focal cerebral ischemia is produced by cauterization of the right distal MCA (middle cerebral artery) with bilateral temporary common carotid artery occlusion in male Long-Evans rats for 90 minutes. All procedures performed on the animals are approved by the University Institutional Animal Care and Use Committee of the University of Pennsylvania. A total of 42 rats (weights; 230–340 g) obtained from Charles River were used in this study. The animals fasted overnight with free access to water prior to the surgical procedure.

Two hours prior to MCA occlusion, varying amounts (control, n=14; 5 mg/kg, n=7; 10 mg/kg, n=7; 20 mg/kg, n=7; and 40 mg/kg, n=7) of the compound, 3,4-dihydro-5-[4-(1-piperidinyl)-butoxy]-1(2H)-isoquinolinone ("DPQ") were dissolved in dimethyl sulfoxide (DMSO) using a sonicator. A volume of 1.28 ml/kg of the resulting solution was injected intraperitoneally into fourteen rats.

The rats were then anesthetized with halothane (4% for induction and 0.8%-1.2% for the surgical procedure) in a mixture of 70% nitrous oxide and 30% oxygen. The body temperature was monitored by a rectal probe and maintained at 37.5±0.5° C. with a heating blanket regulated by a homeothermic blanket control unit (Harvard Apparatus Limited, Kent, U.K.). A catheter (PE-50) was placed into the tail artery, and arterial pressure was continuously monitored and recorded on a Grass polygraph recorder (Model 7D, Grass Instruments, Quincy, Mass.). Samples for blood gas analysis (arterial pH, $PaO_2$ and $PaCO_2$) were also taken from the tail artery catheter and measured with a blood gas analyzer (ABL 30, Radiometer, Copenhagen, Denmark). Arterial blood samples were obtained 30 minutes after MCA occlusion.

The head of the animal was positioned in a stereotaxic frame, and a right parietal incision between the right lateral canthus and the external auditory meatus was made. Using a dental drill constantly cooled with saline, a 3 mm burr hole was prepared over the cortex supplied by the right MCA, 4 mm lateral to the sagital suture and 5 mm caudal to the coronal suture. The dura mater and a thin inner bone layer were kept, care being taken to position the probe over a tissue area devoid of large blood vessels. The flow probe (tip diameter of 1 mm, fiber separation of 0.25 mm) was lowered to the bottom of the cranial burr hole using a micromanipulator. The probe was held stationary by a probe holder secured to the skull with dental cement. The microvascular blood flow in the right parietal cortex was continuously monitored with a laser Doppler flowmeter (FloLab, Moor, Devon, U.K., and Periflux 4001, Perimed, Stockholm, Sweden).

Focal cerebral ischemia was produced by cauterization of the distal portion of the right MCA with bilateral temporary common carotid artery (CCA) occlusion by the procedure of Chen et al., "A Model of Focal Ischemic Stroke in the Rat: Reproducible Extensive Cortical Infarction", Stroke 17:738–43 (1986) and/or Liu et al., "Polyethylene Glycol-conjugated Superoxide Dismutase and Catalase Reduce Ischemic Brain Injury", Am. J. Physiol. 256:H589–93 (1989), both of which are hereby incorporated by reference.

Specifically, bilateral CCA's were isolated, and loops made from polyethylene (PE-10) catheter were carefully passed around the CCA's for later remote occlusion. The incision made previously for placement of the laser doppler probe was extended to allow observation of the rostral end of the zygomatic arch at the fusion point using a dental drill, and the dura mater overlying the MCA was cut. The MCA distal to its crossing with the inferior cerebral vein was lifted by a fine stainless steel hook attached to a micromanipulator and, following bilateral CCA occlusion, the MCA was cauterized with an electrocoagulator. The burr hole was covered with a small piece of Gelform, and the wound was sutured to maintain the brain temperature within the normal or near-normal range.

After 90 minutes of occlusion, the carotid loops were released, the tail arterial catheter was removed, and all of the wounds were sutured. Gentamicin sulfate (10 mg/ml) was topically applied to the wounds to prevent infection. The anesthetic was discontinued, and the animal was returned to his cage after awakening. Water and food were allowed ad libitum.

Two hours after MCA occlusion, the animals were given the same doses of the PARP inhibitor as in the pre-treatment. Twenty-four hours after MCA occlusion, the rats were sacrificed with an intraperitoneal injection of pentobarbital sodium (150 mg/kg). The brain was carefully removed from the skull and cooled in ice-cold artificial CSF for five minutes. The cooled brain was then sectioned in the coronal plane at 2 mm intervals using a rodent brain matrix (RBM-4000C, ASI Instruments, Warren, Mich.). The brain slices were incubated in phosphate-buffered saline containing 2%

2,3,5-triphenyltetrazolium chloride (FTC) at 37° C. for ten minutes. Color photographs were taken of the posterior surface of the stained slices and were used to determine the damaged area at each cross-sectional level using a computer-based image analyzer (NIH Image 1.59). To avoid artifacts due to edema, the damaged area was calculated by subtracting the area of the normal tissue in the hemisphere ipsilateral to the stroke from the area of the hemisphere contralateral to the stroke, by the method of Swanson et al., "A Semiautomated Method for Measuring Brain Infarct Volume", J. Cereb. Blood Flow Metabol. 10:290–93 (1990), the disclosure of which is hereby incorporated by reference. The total volume of infarction was calculated by summation of the damaged volume of the brain slices.

The cauterization of the distal portion of the right MCA with bilateral temporary CCA occlusion consistently produced a well-recognized cortical infarct in the right MCA territory of each test animal. There was an apparent uniformity in the distribution of the damaged area as measured by TTC staining in each group, as shown in FIG. 1.

In FIG. 1, the distribution of the cross-sectional infarct area at representative levels along the rostrocaudal axis was measured from the interaural line in non-treated animals and in animals treated with 10 mg/kg of 3,4-dihydro-5-[4-(1-piperidinyl)-butoxy]-1(2H)-isoquinolinone. The area of damage was expressed as mean±standard deviation. Significant differences between the 10 mg-treated group and the control group were indicated (*$p<0.02$, $p<0.01$, $p<0.001$). The 5 mg/kg and 20 mg/kg curves fell approximately halfway between the control and the 10 mg/kg curves, whereas the 40 mg/kg curve was close to the control. The 5, 20 and 40 mg/kg curves were omitted for clarity.

PARP inhibition led to a significant decrease in the damaged volume in the 5 mg/kg-treated group (106.7±23.2 $mm^3$, $p<0.001$), the 10 mg/kg-treated group (76.4±16.8 $mm^3$, $p<0.001$), and the 20 mg/kg-treated group (110.2±42.0 $mm^3$, $p<0.01$), compared to the control group (165.2±34.0 $mm^3$). The data are expressed as mean±standard deviation. The significance of differences between groups was determined using an analysis of variance (ANOVA) followed by Student's t-test for individual comparisons.

There was no significant difference between the control and the 40 mg/kg-treated group (135.6±44.8 $mm^3$). However, there were significant differences between the 5 mg/kg-treated group and the 10 mg/kg-treated group ($p<0.02$), and between the 10 mg/kg-treated group and the 40 mg/kg-treated group ($p<0.01$), as shown in FIG. 2.

Figure 2:
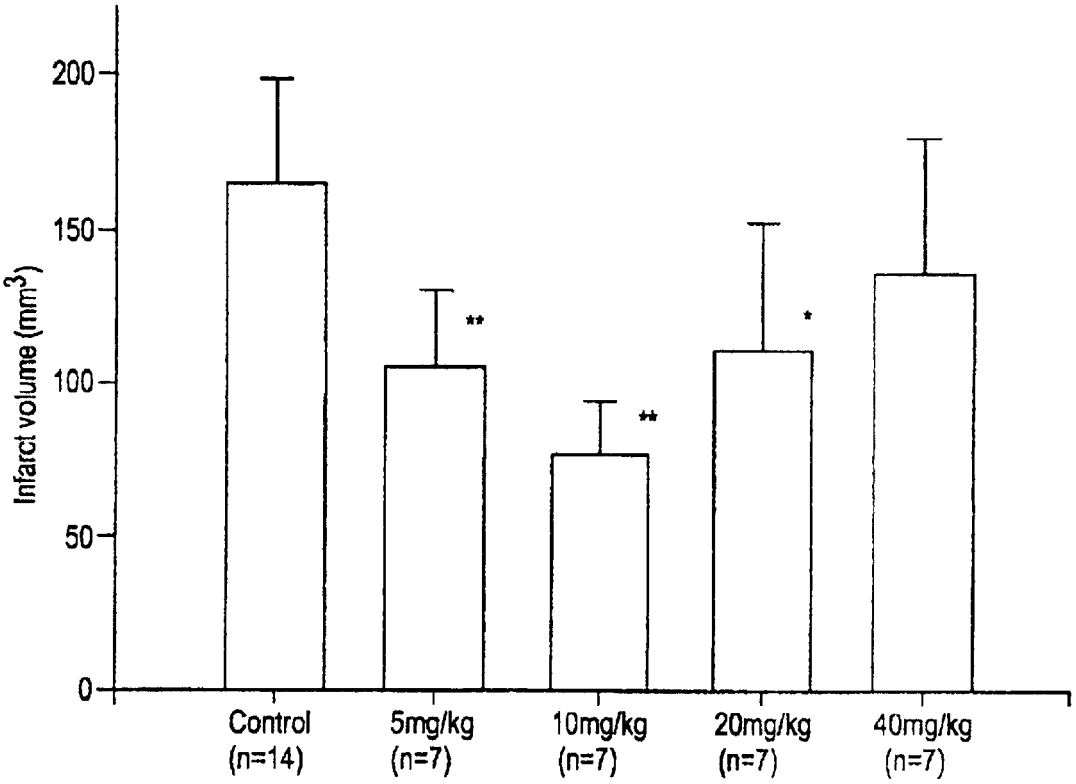
FIG. 2 shows the effect of intraperitoneal administration of 3,4-dihydro-5-[4-(1-piperidinyl)-butoxy]-1(2H)-isoquinolinone on the infarct volume.

In FIG. 2, the effect of intraperitoneal administration of 3,4-dihydro-5-[4-(1-piperidinyl)-butoxy]-1(2H)-isoquinolinone on the infarct volume was depicted graphically. The volumes of infarct were expressed as mean±standard deviation. Significant differences between the treated groups and the control group were indicated (*$p<0.01$, **$p<0.001$). It is not clear why a high dose (40 mg/kg) of the PARP inhibitor, 3,4-dihydro-5-[4-(1-piperidinyl)-butoxy]-1(2H)-isoquinolinone, was less neuroprotective. The U-shaped dose-response curve may suggest dual effects of the compound.

However, overall, the in vivo administration of the inhibitor led to a substantial reduction in infarct volume in the focal cerebral ischemia model in the rat. This result indicated that the activation of PARP plays an important role in the pathogenesis of brain damage in cerebral ischemia.

The values of arterial blood gases ($PaO_2$, $PaCO_2$ and pH) were within the physiological range in the control and treated groups were no significant differences in these parameters among the five groups, as shown below in Table IV. A "steady state" MABP was taken following completion of the surgical preparation, just prior to occlusion; an "ischemia" MABP was taken as the average MABP during occlusion.

TABLE IV

| | $PaO_2$ (mm Hg) | $PaCO_2$ (mm Hg) | pH | MABP (mm Hg) Steady | Ischemia State |
|---|---|---|---|---|---|
| Control group (n = 4) | 125 ± 21 | 38.6 ± 4.6 | 7.33 ± 0.05 | 79 ± 14 | 91 ± 13** |
| 5 mg/kg-treated group (n = 7) | 126 ± 20 | 38.0 ± 2.8 | 7.36 ± 0.02 | 78 ± 5 | 91 ± 12** |
| 10 mg/kg-treated group (n = 7) | 125 ± 16 | 39.3 ± 5.2 | 7.34 ± 0.03 | 80 ± 9 | 90 ± 14* |
| 20 mg/kg-treated group (n = 7) | 122 ± 14 | 41.3 ± 2.8 | 7.35 ± 0.23 | 79 ± 10 | 91 ± 12** |
| 40 mg/kg-treated group (n = 7) | 137 ± 17 | 39.5 ± 4.7 | 7.33 ± 0.24 | 78 ± 4 | 88 ± 12* |

* = Significantly different from the steady state value, $p < 0.05$.
** = Significantly different from the steady state value, $p < 0.01$.

There were no significant differences in any physiological parameter, including mean arterial blood pressure (MABP), prior to MCA and CCA occlusion among the five groups. Although MABP was significantly elevated following occlusion in all five groups, there were no significant differences in MABP during the occlusion period among the groups.

Since the blood flow values obtained from the laser doppler were in arbitrary units, only percent changes from the baseline (prior to occlusion) were reported. Right MCA and bilateral CCA occlusion produced a significant decrease in relative blood flow in the right parietal cortex to 20.8±7.7% of the baseline in the control group (n=5), 18.7±7.4% in the 5 mg/kg-treated group (n=7), 21.4±7.7% in the 10 mg/kg-treated group (n=7) and 19.3±11.2% in the 40 mg/kg-treated group (n=7). There were no significant differences in the blood flow response to occlusion among the four groups. In addition, blood flow showed no significant changes throughout the entire occlusion period in any group.

Following release of the carotid occlusions, a good recovery of blood flow (sometimes hyperemia) was observed in the right MCA territory of all animals. Reperfusion of the ischemic tissue resulted in the formation of NO and peroxynitrite, in addition to oxygen-derived free radicals. All of these radicals have been shown to cause DNA strand breaks and to activate PARP.

This example provided evidence that the related compounds of the present invention are effective in inhibiting PARP activity.

Exemplified compounds of the present invention may be tested for their ability to reduce focal cerebral ischemia in the following simplified procedure. Rats are allowed free access to water and rat chow (Wayne, Chicago, Ill.) until surgery. Housing and anesthesia concur with guidelines established by the institutional Animal Studies Committee, and are in accordance with the PHS Guide for the Care and Use of Laboratory Animals, USDA Regulations, and the AVMA Panel on Euthanasia guidelines.

The animals are anesthetized with isofluorane (induction, 3%, maintenance, 1.25% in a mixture of 30% $O_2$ and 70% $NO_2$ through a face mask. The rectal temperature is maintained at 37° C. with a homeotherinic blanket (Harvard Apparatus, South Natick, Mass.) First, an iv catheter is inserted into the left femoral vein and the line run up through the nape of the neck for connection to a tethered swivel (Instech Laboratories, Plymouth Meeting, Pa.) and remote infusion pump (Stoelting Inc., Wood Dale, Ill.). In some cases, the right femoral artery is cannulated for monitoring arterial blood pressure and heart rate and for obtaining blood samples for arterial blood gas.

The right middle cerebral artery (MCA) is then exposed by making vertical skin incision midway between the right eye and ear and overlying skull is removed with a dental drill (Chen et al, 1986). After incision of the dura, the artery is coagulated at the level of the inferior cerebral vein with a bipolar cautery unit (Valleylab NS2000, Boulder, Colo.), and cut to prevent spontaneous reperfusion (Takahashi et al., 1997). Both common carotid arteries (CCAs) that had been previously isolated and freed of soft tissues and nerves are then ligated using non-traumatic aneurysm clips. After the wounds are closed with surgical clips, the animals are allowed to recover from anesthesia and returned to their cage which is warmed to 27° C. with a heated water underpad and humidified warm tent.

The PARP inhibitor to be tested is first administered 30 min after MCAO as an iv bolus, 10 mg/kg infused over 5 min, followed by a 12 hr continuous infusion of 2 mg/kg/hr (0.3 ml/hr). Ninety minutes after the MCAO, the animals are removed from the infusion tether, briefly reanesthetized with isofluorane, and the carotid clips are removed. The animal is returned to its warm cage and reconnected to the iv infusion pump for the duration of the experiment.

At 24 hrs after permanent MCAO, animals are sedated with ketanine and the heads removed by guillotine. Brains are removed, cooled in ice-cold saline, and sliced into 2 mm coronal sections using a rat brain matrice (Harvard Bioscience, South Natick, Mass.). The brain slices are incubated in phosphate-buffered saline (pH 7.4) containing 2% TTC at 37° C. for 10 min. and then stored in 10% neutral-buffered formalin. Cross-sectiona area of the TTC-unstained region for each brain slice is determined using an image analyzer (MetaMorph, Universal Imaging Corp., West Chester, Pa.). The total volume of infarction in the right hemisphere is calculated by summation of the direct (TTC-negative) and indirect measures of the infarct areas in the component brain slices. The infarcted volumes in vehicle and drug-treated groups (n=8) are tested for significant statistical difference using an unpaired Student-t test.

Various doses of the compounds of the invention may be tested in this model. The compounds are administered in either a single dose or a series of multiple doses, i.p. or i.v., at different times, both before or after the onset of ischemia. Compounds of the invention are expected to provide protection from ischemia in the range of about 0 to 80%.

Heart Ischemia/Reperfusion Injury

The experiments of the heart ischemia/reperfusion injury model is performed using female Sprague-Dawley rats weighing 250–300 g which are anesthetized with sodium pentobarbital at dose of 65 mg/kg intraperitoneally. The rectal temperature is maintained at 37° C. by using a homeothermic blanket system (Harvard Apparatus, South Natick, Mass.). The trachea is cannulated and the rat is ventilated with Room Air by using Harvard Rodent Ventilator (Harvard Apparatus, South Natick, Mass.). The left jugular vein is cannulated with PE-50 tubing for drug delivery. The right carotid artery is cannulated for BP measurement. The heart is exposed by opening the chest at the $4^{th}$ left intercostal space. A main left branch of coronary artery (LAD) is occluded by 4-0 silk ligature for 30 min of ischemia and released for 90 min of reperfusion. During the experiment, arterial BP and EKG are monitored by Micro-Med Cardiovascular System (Louisville, Ky.).

At the end of reperfusion, the LAD coronary artery is re-occluded and about 2 ml of 5% Evans Blue dye is injected through i.v. line to distinguish the ischemic area from non-ischemic area of the heart. Then the heart is immediately taken off and frozen in the freezer. After at least 30 min of freezing, the heart is sliced into five sections with 2 mm thickness and stained in 1% TTC solution for 30 min at 37° C. The right ventricle is trimmed off. Infarct area, risk area and total left ventricular area in each face of the section are measured by using an image analysis system (BIOQUANT, Nashville, Tenn.). The infarct size is calculated as the percent total infarct volume of the total risk volume.

For drug treated group, compounds are administered according to the following three protocols: 1. Single dose of compound is given 60 min prior to the onset of ischemia through i. p. injection. 2. Compound is delivered through i.v. bolus 1 min before the onset of ischemia followed by i.v. infusion until the end of reperfusion. 3. Compound is delivered through i.v. bolus 1 min before the onset of reperfusion followed by i.v. infusion until the end of reperfusion. For each drug-treated group, there is a corresponding vehicle treated group with n=6 or n=8. The difference between vehicle and drug treated groups is compared by using unpaired t-test with $p<0.05$. Various doses of compounds are tested in this model. The compounds are given in either single or multiple doses, i.p or i.v., at different times before or after the onset of ischemia. The compounds of this invention are expected to have ischemia/reperfusion injury protection in the range of 10 to 40 percent in this assay.

As a result of the PARP inhibition activity, the compounds of this invention are expected to protect against ischemia-induced degeneration of rat cortical neurons in vitro and thus may be useful in disorders arising from cerebral ischemia such as stroke, septic shock, or CNS degenerative disorders. They may also be useful in protecting the spinal cord following trauma. As an experimental result of ischemia/reperfusion injury in rats, the present invention is further directed to a method of prophylactic or therapeutic treatment of heart attack, cardiac arrest, cardiac bypass, diabetes, or risk of damage which comprises administering an effective amount of a compound of the present invention for PARP inhibition in unit dosage form.

In Vitro Radiosensitization

In vitro radiosensitization may be measured with the use of a human prostate cancer cell line, PC-3s, which are plated in 6 well dishes and grown at monolayer cultures in RPMI1640 supplemented with 10% FCS. The cells are maintained at 37° C. in 5% $CO_2$ and 95% air. The cells are exposed to a dose response (0.1 mM to 0.1 μM) of 3 different PARP inhibitors prior to irradiation at one sublethal dose level. For all treatment groups, the six well plates are exposed at room temperature in a Seifert 250 kV/15 mA irradiator with a 0.5 mm Cu/1 mm. Cell viability is examined by exclusion of 0.4% trypan blue. Dye exclusion is assessed visually by microscopy and viable cell number was calculated by subtracting the number of cells from the viable cell number and dividing by the total number of cells. Cell proliferation rates are calculated by the amount of $^3$H-thymidine incorporation post-irradiation. The PARP inhibitors are expected to radiosensitize the cells.

Measuring Altered Gene Expression in mRNA Senescent Cells

Gene expression alteration may be measured with human fibroblast BJ cells which, at Population Doubling (PDL) 94, are plated in regular growth medium and then changed to low serum medium to reflect physiological conditions described in Linskens, et al., Nucleic Acids Res. 23:16:3244–3251 (1995). A medium of DMEMW/199 supplemented with 0.5% bovine calf serum is used. The cells are treated daily for 13 days. The control cells are treated with and without the solvent used to administer the PARP inhibitor. The untreated old and young control cells are tested for comparison. RNA is prepared from the treated and control cells according to the techniques described in PCT Publication No. 96/13610 and Northern blotting is conducted. Probes specific for senescence-related genes are analyzed, and treated and control cells compared. In analyzing the results, the lowest level of gene expression is arbitrarily set at 1 to provide a basis for comparison. Three genes particularly relevant to age-related changes in the skin are collagen, collagenase and elastin. West, Arch. Derm. 130:87–95 (1994). Elastin expression of the cells treated with the PARP inhibitor is expected to be significantly increased in comparison with the control cells. Elastin expression should be significantly higher in young cells compared to senescent cells, and thus treatment with the PARP inhibitor should cause elastin expression levels in senescent cells to change to levels similar to those found in much younger cells. Similarly, a beneficial effect should be seen in collagenase and collagen expression with treatment with the PARP inhibitors.

Neuroprotective Effects of PARP Inhibitors on Chronic Constriction Injury (CCI) in Rats Adult male Sprague-Dawley rats, 300–350 g, are anesthetized with intraperitoneal 50 mg/kg sodium pentobarbital. Nerve ligation is performed by exposing one side of the rat's sciatic nerves and dissecting a 5–7 mm-long nerve segment and closing with four loose ligatures at a 1.0–1.5-mm, followed by implanting of an intrathecal catheter and inserting of a gentamicin sulfate-flushed polyethylene (PE-10) tube into the subarachnoid space through an incision at the cisterna magna. The caudal end of the catheter is gently threaded to the lumbar enlargement and the rostral end is secured with dental cement to a screw embedded in the skull and the skin wound is closed with wound clips.

Thermal hyperalgesia to radiant heat is assessed by using a paw-withdrawal test. The rat is placed in a plastic cylinder on a 3-mm thick glass plate with a radiant heat source from a projection bulb placed directly under the plantar surface of the rat's hindpaw. The paw-withdrawal latency is defined as the time elapsed from the onset of radiant heat stimulation to withdrawal of the rat's hindpaw.

Mechanical hyperalgesia is assessed by placing the rat in a cage with a bottom made of performed metal sheet with many small square holes. Duration of paw-withdrawal is recorded after pricing the mid-plantar surface of the rat's hindpaw with the tip of a safety pin inserted through the cage bottom.

Mechano-allodynia is assessed by placing a rat in a cage similar to the previous test, and applying von Frey filaments in ascending order of bending force ranging from 0.07 to 76 g to the mid-plantar surface of the rat's hindpaw. A von Frey filament is applied perpendicular to the skin and depressed slowly until it bends. A threshold force of response is defined as the first filament in the series to evoke at least one clear paw-withdrawal out of five applications.

Dark neurons are observed bilaterally within the spinal cord dorsal horn, particularly in laminae I–II, of rats 8 days after unilateral sciatic nerve ligation as compared with sham operated rats. Various doses of PARP inhibitors are tested in this model and shown to reduce both incidence of dark neurons and neuropathic pain behavior in CCI rats.

Treatment and Prevention of Gout and Symptoms of Gout

Deposition of crystals of monosodium urate (MSU crystals) in the joint articular space is the etiological cause of inflammatory pathologies such as gout and pseudogout. Clinically, these inflammatory diseases are associated with oedema and erythema of the joints with consequently severe pain. A strong infiltration of leucocytes in the intraarticular and periarticular space leading to: 1) acute, episodic articular and periarticular inflammation, and 2) chronic articular changes, are also characteristic of this pathology. It has long been clear that neutrophils are the predominant cell type recovered from these inflammatory joints (Dieppe et al., (1979). Synovial fluid crystals. Q. J. Med. XLVIII: 533–553; Terkletaub, (1991). Monocyte-derived neutrophil chemotactic factor/interleukin-8 is a potential mediator of crystal-induced inflammation. Arth. Rheum. 34: 894–903.). A better understanding of the inflammatory process elicited by MSU crystals, and the fact that there is a clear relationship between these crystals and gouty arthritis, has prompted the characterisation of experimental models of crystal-induced inflammation. Examples of models where crystal challenge has led to cell recruitment into specific cavities, are canine joints (Phelps & McCarty, 1996, Ann Int. Med. 9: 115–125), rat pleurisy (Deporter et al., 1979, Br. J. Pharmacol. 65: 163–165; Sedgwick et al., 1985, Agents Actions 17: 209–213), and utilisation of a pre-formed rat air-pouch (Brookes et al., 1987). The latter experimental system has shown that neutrophil accumulation was related to generation of chemoattractants such as $LTB_4$, which was subsequently inhibited by colchicine (Brooks et al., 1987, Br. J. Pharmacol. 90: 413–419).

Neutrophils have been shown to be activated by MSU crystals, releasing an array of mediators that may be, in part, responsible for the local and systemic inflammatory manifestations found in crystal-induced joint disorders. The crystals interact with neutrophils leading to the release of lysomal enzymes (Hoffstein et al., 1975, Arth. Rheum. 18: 153–165), release of oxygen derived free radicals (Simchowitz et al., 1982, Arth. Rheum. 25: 181–188; Abramson et al., 1982, Arthr Rheum. 25: 174–180), induction of phospholipase $A_2$ ($PLA_2$) in leucocytes (Bomalaski et al., 1990, J. Immunol. 145: 3391–3397), and activation of synthesis of 5-lipoxygenase products (Poubelle et al., 1987, Biochem. Biophys. Res. Commun. 149: 649–657).

In vitro, MSU crystals have been shown to release the cytokine interleukin-1β (IL-1β) from human neutrophils, adding this stimulus to a list of others that also release this cytokine, such as zymosan, LPS, phorbol esters, granulocyte macrophage-colony stimulating hormone (GM-CSF) and TNF-alpha. Furthermore it has also been shown that human monocytes and synoviocytes can synthesise and release various cytokines such as IL-6 and IL-8 (Gueme et al., 1989, Arth. Rheum. 32: 1443–1452; Terkeltaub et al., 1991, Arth. Rheum. 34: 894–903). In addition, colchicine selectively inhibits MSU crystal- and TNF-α induced release of IL-1β (Roberge et al., 1994, J. Immunol. 152: 5485–5494).

In experimental models of gout the synthesis of a CXC chemokine selective for neutrophils, such as IL-8, has also been observed, but not that of a CC chemokine monocyte chemoattractant protein-1 (MCP-1) (Hachicha et al., 1995, J. Exp. Med. 182: 2019–2025). These results suggest that production of IL-8 and abolition of the release of MCP-1, will lead to an event where, theoretically there will be a recruitment of neutrophils but not mononuclear cells. This hypothesis is in accordance with the pathological state of gout and pseudogout, where the predominant inflammatory cell is the neutrophil (Hachicha et al., 1995). In addition MSU crystal activation of mononuclear phagocytes, which are normally found in the joint space, also induces secretion of IL-8 (Terkeltaub et al., 1991). The importance of IL-8 in this pathology has been shown in synovial fluids of patients with acute gouty arthritis where it occurs in elevated amounts (Terkeltaub et al., 199 1; di Giovine et al., 1991, J. Clin. Invest. 87: 1375–1381). The use of a neutralising antibody against IL-8 has been shown significantly to attenuate the crystal induced joint swelling at 12 h and neutrophil infiltration into artritic joints at 12 and 24 h in a rabbit model (Nishimura et al, 1997, J. Leukoc. Biol. 62: 444–449).

These studies demonstrate the importance of both the emigrating neutrophil and the chemokine IL-8, as well as the release of this and other cytokines from resident cells such as the synoviocytes, macrophages and mast cells in treating gout. Since neutroplis are not present or are extremely rare in normal synovial fluid, enhanced neutrophil-endothelial adhesion is necessary for gout to occur (Terkeltaub, 1996, In. Koopman, W. J. editor. Arthritis and allied conditions: a textbook of rheumatology. Baltimore: Williams and Wilkins: pp. 2085–2102, and Terkeltaub, 1992, In Inflammation, Basic Principles and Clinical Correlates, ed. by J. I. Gallin, I. M. Goldstein and R. Snyderman, pp 977–981, Raven Press, New York). IL-1β and TNF-alpha may be critical in mediating the rapid up-regulation of the major endothelial ligand for neutrophils. For instance rapid and prolonged expression of E-selectin in response to injection of urate crystals has been demonstrated in pig skin (Chapman et al., 1996, Br. J. Rheumatol. 35: 323–334). The release of cytokines, chemokines and products of the arachidonic acid cascade system lead to the recruitment of neutrophils in this pathology, and inhibition of these leads to an attenuation of the pathology.

The following gout model may be used to test a PARP inhibitor according to the present invention.

Male outbread Swiss albino mice (20–22 g body weight) were purchased from Banton and Kingsman (T. O. strain; Hull, Humberside) and maintained on a standard chow pellet diet with tap water ad libitum and a 12:00 h light/dark cycle. All animals were housed for 1 week prior to experimentation to allow body weight to reach 28–30 g.

1,11b-dihydrobenzopyrano[4,3,2-de]isoquinolin-1-one, as an example PARP inhibitor, was dissolved in 100% DMSO at room temperature at a concentration of 45 mg in 2 ml. The compound was then injected into the peritoneal cavity, so as each mouse received a single dose corresponding to 45 mg/2 ml/kg (e.g. 60 μl for a mouse of 30 g). Control mice received DMSO at 2 ml/kg i.p. A third group of mice which were left untreated were added to control for potential effects of the vehicle. The study involved therefore, the following three groups: group A, untreated mice, n=6, group B, DMSO-treated mice, n=8, and group C, mice treated with 1,11b-dihydrobenzopyrano[4,3,2-de ]isoquinolin-1-one, n=8

MSU crystal-induced neutrophil recruitment was tested as follows. In all cases, mice were treated 1 h after the treatment noted above, with MSU crystals. A homogeneous suspension of MSU crystals was obtained by a 30 min rotation. Peritonitis was induced by injection of 3 mg MSU crystals in 0.5 ml PBS (0.1 M, pH 7.4), and the recruitment of neutrophils into the cavity evaluated at the 6 h time point (Getting et al., 1997, J. Pharmacol. Exp. Ther. 283: 123–130). Animals were then euthanised by $CO_2$ exposure and the peritoneal cavity washed with 3 ml of PBS supplemented with 3 mM EDTA and 25 U/ml heparin.

An aliquot (100 μl) of the lavage fluid was then diluted 1:10 in Turk's solution (0.01% crystal violet in 3% acetic acid). The samples were then vortexed and 10 μl of the stained cell solution were placed in a Neubauer haematocymometer and neutrophils numbers counted using a light microscope (Olympus B061). Cell-free supernatants have been prepared by centrifugation and stored for potential future analysis.

Data are shown for single mice, and also shown as means±S.E. of (n) mice per group. Statistical differences were determined by ANOVA, plus Bonferroni test. A P value <0.05 was taken as significant.

TABLE V reports the number of neutrophils as measured 6 h post-MSU crystal injection in the three experimental groups.

TABLE V

Effect of 1,11b-dihydrobenzopyrano[4,3,2-de]isoquinolin-1-one on MSU crystal induced neutrophil migration as evaluated at the 6 h time-point.

| Mouse No. | Group | Neutrophil Numbers | Group | Neutrophil Numbers | Group | Neutrophil Numbers |
|---|---|---|---|---|---|---|
| 1 | A | 4.9 | B | 6.0 | C | 5.1 |
| 2 | A | 5.4 | B | 6.6 | C | 2.1 |
| 3 | A | 6.3 | B | 7.5 | C | 2.4 |
| 4 | A | 6.9 | B | 7.8 | C | 2.4 |
| 5 | A | 5.7 | B | 5.1 | C | 3.0 |
| 6 | A | 6.0 | B | 5.7 | C | 3.0 |
| 7 | | | B | 5.7 | C | 2.7 |
| 8 | | | B | 6.0 | C | 2.1 |

Legend: Mice were left untreated (group A), received vehicle DMSO (2 ml/kg i.p.; group B) or 1,11b-dihydrobenzopyrano[4,3,2-de]isoquinolin-1-one (45 mg/kg i.p.; group C), 1 h prior to peritoneal injection of 3 mg MSU crystals at time 0. Neutrophil influx in the peritoneal cavity was measured at the 6 h time-point after collection of the lavage fluids and specific staining as described in the experimental section. Values for neutrophil numbers are $10^6$ per mouse.

TABLE VI illustrates these data as means±S.E. It can be seen that DMSO produced a modest not significant increase in cell migration (+7%). In contrast, the exemplary compound of the present invention, at the dose of 45 mg/kg, significantly reduced cell influx, with a calculated 55% of inhibition vs. the vehicle group.

TABLE VI

Accumulation of data for the effect of the exemplified compound of the present invention (means).

| Experimental Group | Stimulus | Neutrophils ($10^6$ per mouse) |
|---|---|---|
| A | MSU crystals (3 mg) | 5.87 ± 0.28 (6) |
| B | MSU crystals (3 mg) | 6.30 ± 0.33 (8) |
| C | MSU crystals (3 mg) | 2.85 ± 0.34 (8) * |

Legend: as in TABLE IV. Values are mean ± S.E. of (n) mice per group.
* P < 0.05 vs. group B.

These results demonstrate the compounds and compositions of the present invention may be useful in treating and/or preventing gout, such as by reducing or eliminating urate crystal induced neutrophil recruitment.

The invention being thus described, it will be obvious that the same may be varied in many ways. Such variations are not to be regarded as a departure from the spirit and scope of the invention, and all such modifications are intended to be included within the scope of the following claims. All references cited herein are incorporated in their entirety by reference herein.
We claim:
1. A compound selected from the group consisting of:
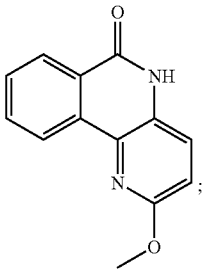
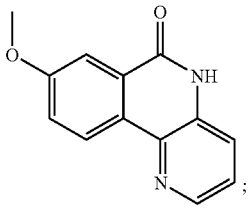
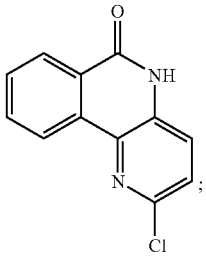
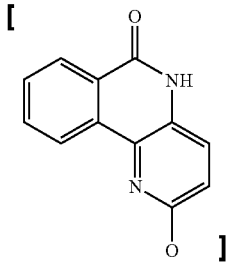
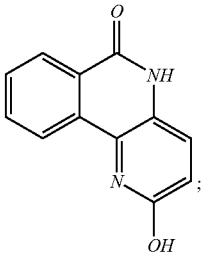
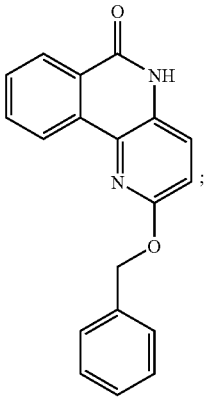
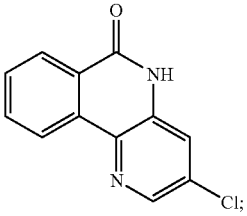
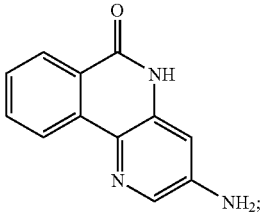
-continued
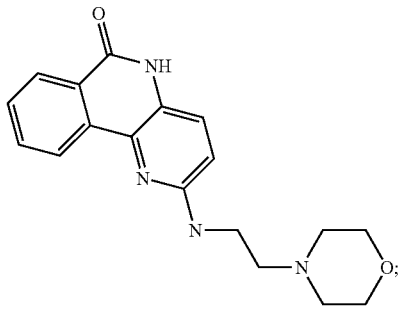
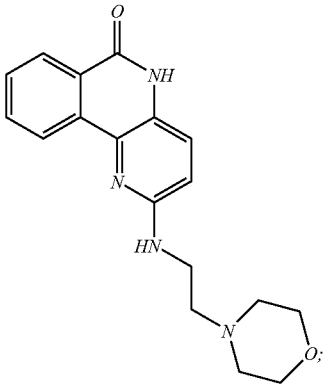
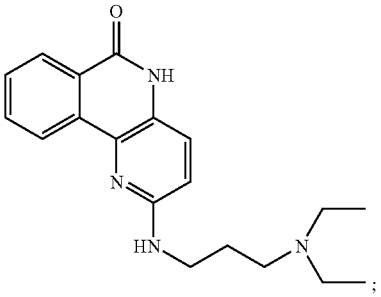
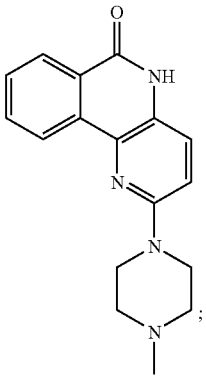
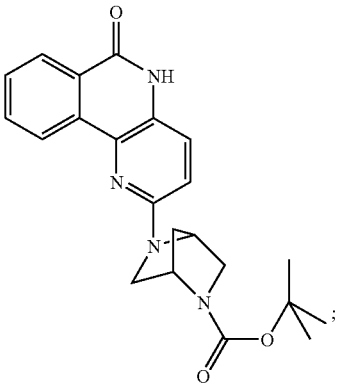

-continued
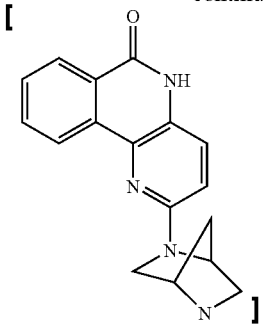
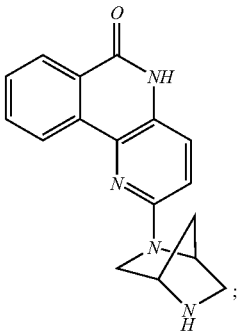
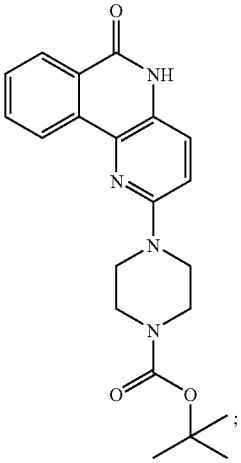
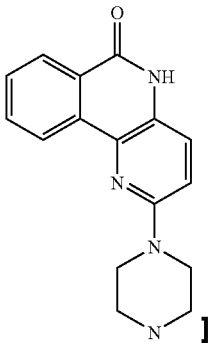
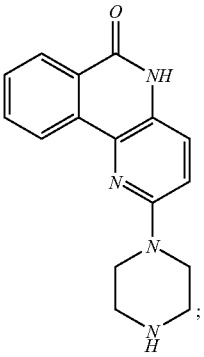
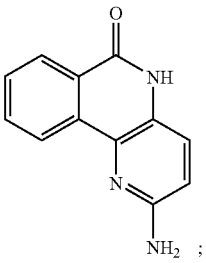
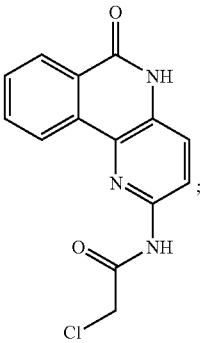
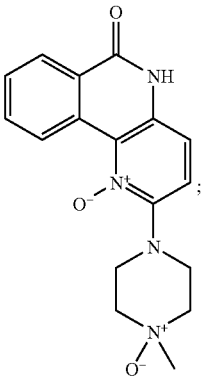
-continued
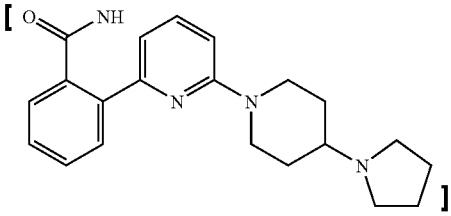
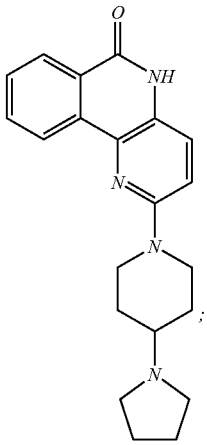
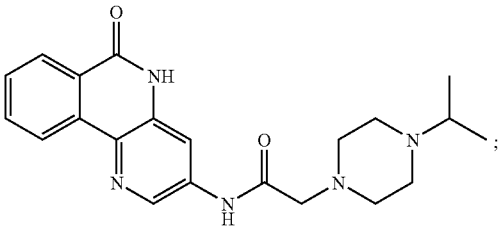
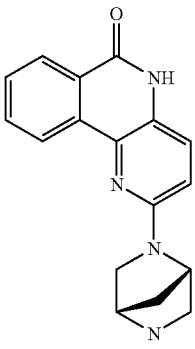
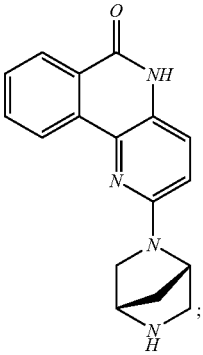
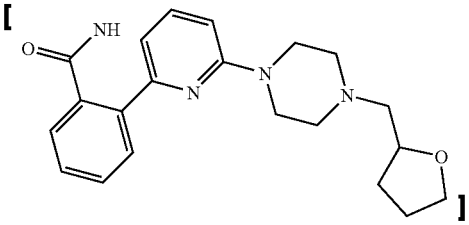

-continued
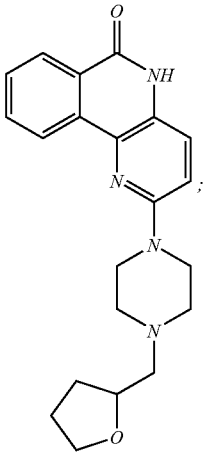
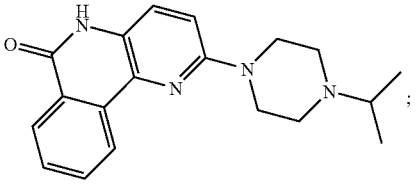
[
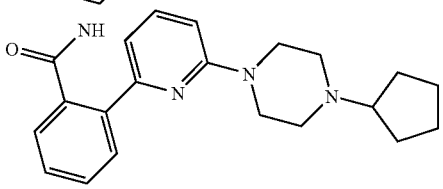
]
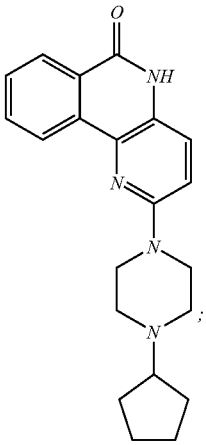
amd
-continued
[
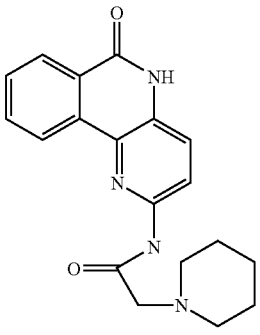
]
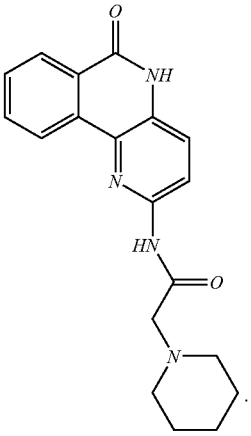
2. A compound selected from the group consisting of:
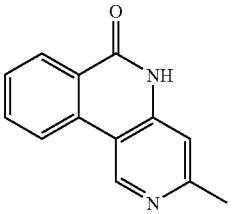
and
[
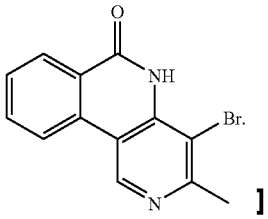
]
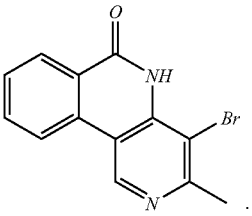
* * * * *